US012655471B2

(12) United States Patent
Sims et al.

(10) Patent No.: US 12,655,471 B2
(45) Date of Patent: Jun. 16, 2026

(54) RNA PRINTING AND SEQUENCING DEVICES, METHODS, AND SYSTEMS

(71) Applicant: The Trustees of Columbia University in the City of New York, New York, NY (US)

(72) Inventors: Peter A. Sims, Ardsley, NY (US); Sayantan Bose, Collegeville, PA (US); Jinzhou Yuan, Edgewater, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 1214 days.

(21) Appl. No.: 17/480,839

(22) Filed: Sep. 21, 2021

(65) Prior Publication Data

US 2022/0064717 A1     Mar. 3, 2022

Related U.S. Application Data

(63) Continuation of application No. 15/576,925, filed as application No. PCT/US2016/034270 on May 26, 2016, now abandoned.

(60) Provisional application No. 62/166,565, filed on May 26, 2015.

(51) Int. Cl.
C12Q 1/6834          (2018.01)
(52) U.S. Cl.
CPC ................................. C12Q 1/6834 (2013.01)
(58) Field of Classification Search
None
See application file for complete search history.

(56) References Cited

U.S. PATENT DOCUMENTS

| | | | |
|---|---|---|---|
| 8,835,358 B2 | 9/2014 | Fodor et al. | |
| 9,174,216 B2 | 11/2015 | Handique et al. | |
| 9,290,808 B2 | 3/2016 | Fodor et al. | |
| 9,290,809 B2 | 3/2016 | Fodor et al. | |
| 9,315,857 B2 | 4/2016 | Fu et al. | |
| 9,567,631 B2* | 2/2017 | Hindson | .............. C12Q 1/6806 |
| 9,708,659 B2 | 7/2017 | Fodor et al. | |
| 9,816,137 B2 | 11/2017 | Fodor et al. | |
| 9,845,502 B2 | 12/2017 | Fodor et al. | |

(Continued)

FOREIGN PATENT DOCUMENTS

| | | |
|---|---|---|
| WO | WO 00/65094 | 11/2000 |
| WO | WO 2010/138960 | 12/2010 |

(Continued)

OTHER PUBLICATIONS

Bose et al. Genome Biology (published Jun. 6, 2015) 16:120, p. 1-16 (Year: 2015).*

(Continued)

*Primary Examiner* — Carla J Myers
(74) *Attorney, Agent, or Firm* — Casimir Jones, S.C.; Jason R. Bond

(57)     ABSTRACT

Many important biological questions demand single-cell transcriptomics on a large scale. Hence, new tools are urgently needed for efficient, inexpensive manipulation of RNA from individual cells. Described herein are devices, systems, and methods for trapping single-cell lysates in sealed, microwells capable of printing RNA on glass or capturing RNA on beads.

12 Claims, 25 Drawing Sheets
(18 of 25 Drawing Sheet(s) Filed in Color)

Specification includes a Sequence Listing.

Bead 1

Optical code:     1     1     0     0     1     0     1     1

Sequence code:   110010110000 = ACAGACGTCTATG

Bead 2

(56) References Cited

U.S. PATENT DOCUMENTS

| | | |
|---|---|---|
| 10,155,981 B2 | 12/2018 | Brenner et al. |
| 10,227,648 B2 | 3/2019 | Hindson et al. |
| 10,240,197 B1 | 3/2019 | Brenner et al. |
| 10,273,541 B2 | 4/2019 | Hindson et al. |
| 10,280,459 B1 | 5/2019 | Brenner et al. |
| 2003/0108867 A1 | 6/2003 | Chee et al. |
| 2006/0177833 A1 | 8/2006 | Brenner et al. |
| 2011/0021102 A1 | 1/2011 | Inoue et al. |
| 2012/0088691 A1 | 4/2012 | Chen et al. |
| 2012/0142014 A1 | 6/2012 | Cai |
| 2014/0031243 A1 | 1/2014 | Cai et al. |
| 2014/0073520 A1 | 3/2014 | Cai et al. |
| 2014/0170645 A1 | 6/2014 | Jovanovich et al. |
| 2014/0206554 A1 | 7/2014 | Hindson et al. |
| 2015/0329891 A1 | 11/2015 | Tan et al. |
| 2016/0244825 A1 | 8/2016 | Vigneault et al. |
| 2017/0081705 A1 | 3/2017 | Davies et al. |
| 2017/0337459 A1 | 11/2017 | Fodor et al. |
| 2018/0216160 A1 | 8/2018 | Abate et al. |
| 2019/0046307 A1 | 2/2019 | Schulter et al. |
| 2019/0064168 A1 | 2/2019 | Handique et al. |
| 2019/0085324 A1 | 3/2019 | Regev et al. |
| 2019/0085412 A1 | 3/2019 | Fan et al. |
| 2019/0127782 A1 | 5/2019 | Regev et al. |
| 2019/0345488 A1 | 11/2019 | Soumillon et al. |

FOREIGN PATENT DOCUMENTS

| | | |
|---|---|---|
| WO | WO 2013/188872 | 12/2013 |
| WO | WO 2014/089700 | 6/2014 |
| WO | WO 2014/201273 | 12/2014 |
| WO | WO 2015/031691 | 3/2015 |
| WO | WO 2015/044428 | 4/2015 |
| WO | WO 2015/164212 | 10/2015 |
| WO | WO 2016/040476 | 3/2016 |
| WO | WO 2016/145409 | 9/2016 |
| WO | WO 2016/191533 | 12/2016 |
| WO | WO 2016/207441 | 12/2016 |
| WO | WO 2017/059094 | 4/2017 |
| WO | WO 2017/087873 | 5/2017 |
| WO | WO 2017/112957 | 6/2017 |
| WO | WO 2017/164936 | 9/2017 |
| WO | WO 2019/079399 | 4/2019 |

OTHER PUBLICATIONS

Bose et al., "Scalable microfluidics for single-cell RNA printing and sequencing," Genome Biology, Jun. 6, 2015, vol. 16(120), pp. 1-16.

Cai, "Turning single cells into microarrays by super-resolution barcoding", Briefings In Functional Genomics, Nov. 22, 2012, vol. 12(2), pp. 75-80.

Chen et al., "Spatially resolved, highly multiplexed RNA profiling in single cells," Science, Apr. 24, 2015, vol. 348(6233): aaa6090, pp. 1-36.

Chu et al., "RNA Sequencing: Platform Selection, Experimental Design, and Data Interpretation", Nucleic Acid Therapeutics, Aug. 2012, vol. 22(4), pp. 271-274.

Dey et al., "Integrated genome and transcriptome sequencing of the same cell", Nature Biotechnology, Jan. 19, 2015, vol. 33(3), pp. 285-289.

Fan et al., "Combinatorial labeling of single cell for gene expression cytometry," Science, Feb. 6, 2015, vol. 347(6222), pp. 628, 1258367-1-8.

Farmer, "Systems Biology Faculty Nab Chan Zuckerberg Initiative Grants to Advance Human Cell Atlas", Oct. 16, 2017, Columbia University, Department of Systems Biology, Columbia Systems Biology, https://systemsbiology.columbia.edu/news/systems-biology-faculty-nab-chan-zuckerberg-initiative-grants-to-advance-human-cell-atlas.

Fu et al., "Single Cell Total RNA Sequencing through Isothermal Amplification in Picoliter-Droplet Emulsion", Analytical Chemistry, Oct. 26, 2016, vol. 88(22), pp. 10795-10799.

Gierahn et al., "Seq-Well: A Portable, Low-Cost Platform for High-Throughput Single-Cell RNA-Seq of Low-Input Samples", Nature Methods, Apr. 2017, vol. 14(4), pp. 395-398.

Goodarzi et al., "Revealing Global Regulatory Perturbations across Human Cancers", Molecular Cell, Dec. 11, 2009, vol. 36(5), pp. 900-911.

Habib et al., "Div-Seq: Single-nucleus RNA-Seq reveals dynamics of rare adult newborn neurons", Science, Jul. 28, 2016, vol. 353(6302), pp. 1-8.

Hashimshony et al., "CEL-Seq: single-cell RNA-Seq by multi-plexed linear amplification", Cell Reports, Sep. 27, 2012, vol. 2(3) pp. 666-673.

Hiroaki, "Systems Biology: A Brief Overview," Science, vol. 295, No. 5560, pp. 1662-1664, Mar. 2002 (Abstract).

International Preliminary Report on Patentability for International Application No. PCT/US2016/034270 issued Dec. 7, 2017.

International Search Report and Written Opinion for International Application No. PCT/US2016/034270 issued Oct. 7, 2016.

International Search Report and Written Opinion for International Application No. PCT/US2018/062650 dated Feb. 13, 2019.

Kimmerling et al., "A microfluidic platform enabling single-cell RNA-seq of multigenerational lineages", Nature Communications, Jan. 6, 2016, vol. 7, pp. 1-7.

Kitano, "Systems Biology: A Brief Overview," Science, Mar. 1, 2002, vol. 295(5560), pp. 1662-1664.

Klein et al., "Droplet Barcoding for Single-Cell Transcriptomics Applied to Embryonic Stem Cells", Cell, May 21, 2015, vol. 161(5), pp. 1187-1201.

Kolodziejczyk et al., "The technology and biology of single-cell RNA sequencing," Molecular Cell, May 21, 2015, vol. 58(4), pp. 610-620.

Lan et al., "Single-cell genome sequencing at ultra-high-throughput with microfluidic droplet barcoding", Nature Biotechnology, Jul. 2017, vol. 35(7), pp. 640-646 (Abstract).

Li et al., "Injection Molded Microfludics for Establishing High-Density Single Cell Arrays in an Open Hydrogel Format," Analytical Chemistry, vol. 92, No. 3, pp. 2794-2801, Jan. 2020.

Liu et al., "Emerging imaging and genomic tools for developmental systems biology," Developmental Cell, Mar. 21, 2016, vol. 36(6), pp. 597-610.

McDonald et al., "Poly(dimethylsiloxane) as a Material for Fabricating Microfluidic Devices", Accounts of Chemical Research, Jul. 2002, vol. 35(7), pp. 491-499.

Meade-Kelly, "Divide and conquer: New single cell approach broadens range of cell types that can be studied in the brain", Jul. 29, 2016, Broad Institute, Broadminded Blog, https://www.broadinstitute.org/blog/divide-and-conquer-new-single-cell-approach-broadens-range-cell-types-can-be-studied-brain.

Men et al., "Digital Polymerase Chain Reaction in an Array of Femtoliter Polydimethylsiloxane Microreactors", Analytical Chemistry, Apr. 7, 2012, vol. 84(10), pp. 4262-4266.

U.S. Appl. No. 61/982,001, filed Apr. 21, 2014.

Shiroguchi et al., "Digital RNA sequencing minimizes sequence-dependent bias and amplification noise with optimized single-molecule barcodes", Proceedings of the National Academy of Sciences, Jan. 24, 2012, vol. 109(4), pp. 1347-1352.

Streets et al., "Microfluidic single-cell whole-transcriptome sequencing," Proceedings of the National Academy of Sciences, May 13, 2014, vol. 111(19), pp. 7048-7053.

Sweedler et al., "Single cell analysis", Analytical and Bioanalytical Chemistry, Jan. 2007, vol. 387(1), pp. 1-2.

Van Der Maaten et al., "Visualizing Data using t-SNE", Journal of Machine Learning Research, Nov. 2008, vol. 9, pp. 2579-2605.

White et al., "High-throughput microfluidic single-cell RT-qPCR", Proceedings of the National Academy of Sciences of the United States of America, Jun. 17, 2011, vol. 108(34), pp. 13999-14004.

Wu et al., "Quantitative assessment of single-cell RNA-sequencing methods", Nature Methods, Oct. 20, 2013, vol. 11(1), pp. 41-46.

Yuan et al., "An Automated Microwell Platform for Large-Scale Single Cell RNA-Seq", Scientific Reports, Sep. 27, 2016, vol. 6, pp. 1-10.

(56) References Cited

OTHER PUBLICATIONS

Zilionis et al., "Single-cell barcoding and sequencing using droplet microfluidics", Nature Protocols, Dec. 8, 2016, vol. 12(1), pp. 44-73.

* cited by examiner

Bright Field with
Fluorescent Cell

Fluorescence After
Reverse Transcription

Fluorescence in a Device with
No Cells (Negative Control)

FIG. 3A

Adapter-Linked
Beads

Multi-well Barcoded Adapter
Oligo Plate

Mix

Expand

Multi-well Barcode-Appender
Oligo Plate

Mix

| Bright Field | Fluorescence After Reverse Transcription | Fluorescence After RNase Digestion |

1) Unseal and Wash.
2) On-Chip Reverse Transcription.
3) On-Chip Second-Strand Synthesis On-Chip *In Vitro* Transcription

BLUE ⊥
RED ●

FIG. 8A

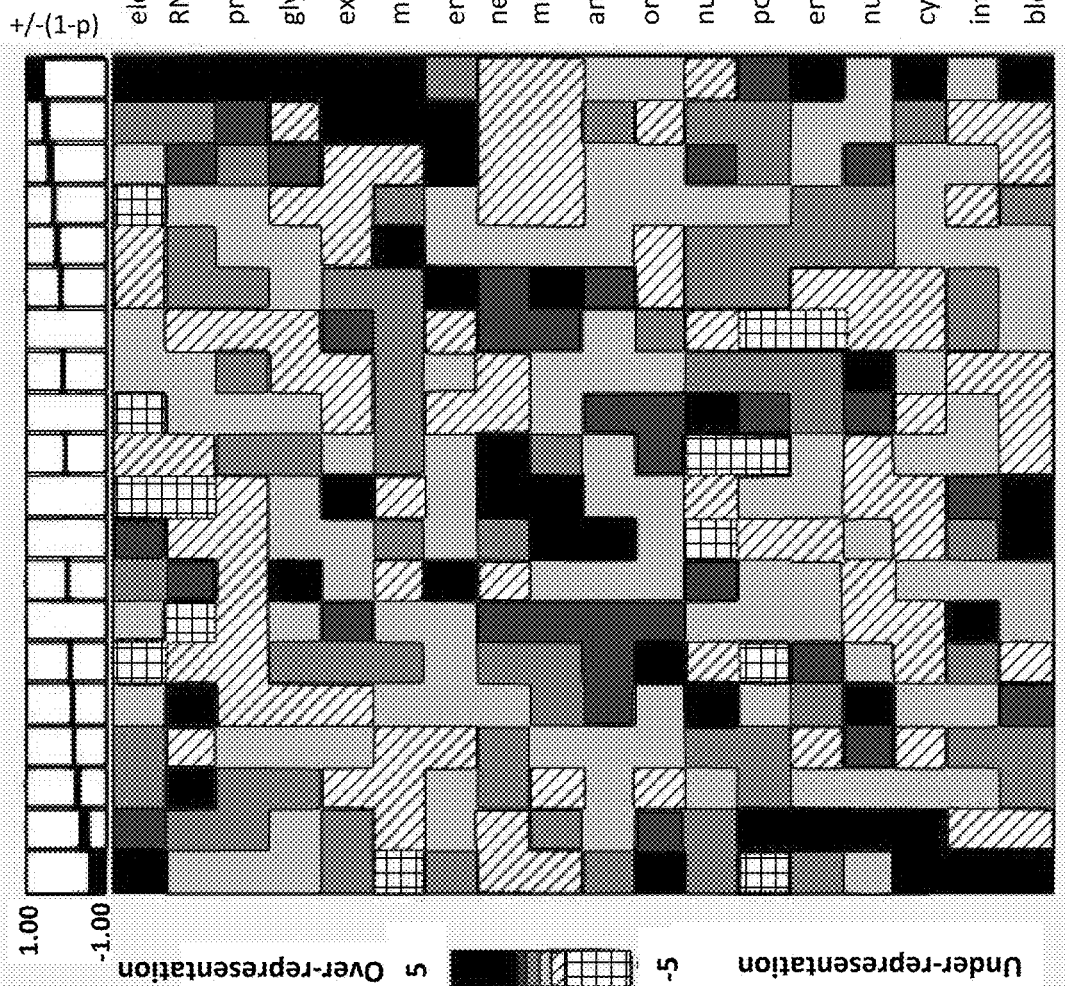

High in U87 Cells

High in MCF10a Cells

+/-(1-p)

electron carrier activity, GO:0009055
RNA splicing, via transesterification reactions, GO:0000375
proteasome complex (sensu Eukaryota), GO:0000502
glycolysis, GO:0006096
extracellular matrix structural constituent, GO:0005201
microtubule-based process, GO:0007017
endosome, GO:0005768
neurotransmitter receptor activity, GO:0030594
monooxygenase activity, GO:0004497
antiporter activity, GO:0015297
organic acid transport, GO:0015849
nucleotidyltransferase activity, GO:0016779
positive regulation of transcription, GO:0045893
endoplasmic reticulum part, GO:0044432
nucleolus, GO:0005730
cytosolic ribosome (sensu Eukaryota), GO:0005830
intermediate filament, GO:0005882
blood vessel development, GO:0001568

1.00
-1.00

Over-representation    5

-5    Under-representation

Adapter-Linked Beads 96-well Barcoded Adapter Oligo Plate

Mix

Expand 96-well Barcode-Appender Oligo Plate

Mix

SEQUENCE LISTING

<160> NUMBER OF SEQ ID NOS: 228

<210> SEQ ID NO 1
<211> LENGTH: 54
<212> TYPE: DNA
<213> ORGANISM: Artificial Sequence
<220> FEATURE:
<223> OTHER INFORMATION: Bead Capture Oligo

<400> SEQUENCE: 1

-continued

```
aggtaaggta atacgactca ctataggggt tcagagttct acagtccgac gatc          54

<210> SEQ ID NO 2
<211> LENGTH: 42
<212> TYPE: DNA
<213> ORGANISM: Artificial Sequence
<220> FEATURE:
<223> OTHER INFORMATION: Reverse Transcription Primer 1
<220> FEATURE:
<221> NAME/KEY: misc_feature
<222> LOCATION: (23)..(30)
<223> OTHER INFORMATION: n is a, c, g, or t
<220> FEATURE:
<221> NAME/KEY: misc_feature
<222> LOCATION: (37)..(42)
<223> OTHER INFORMATION: n is a, c, g, or t

<400> SEQUENCE: 2
gccttggcac ccgagaattc cannnnnnnn cgtgatnnnn nn          42

<210> SEQ ID NO 3
<211> LENGTH: 42
<212> TYPE: DNA
<213> ORGANISM: Artificial Sequence
<220> FEATURE:
<223> OTHER INFORMATION: Reverse Transcription Primer 2
<220> FEATURE:
<221> NAME/KEY: misc_feature
<222> LOCATION: (23)..(30)
<223> OTHER INFORMATION: n is a, c, g, or t
<220> FEATURE:
<221> NAME/KEY: misc_feature
<222> LOCATION: (37)..(42)
<223> OTHER INFORMATION: n is a, c, g, or t

<400> SEQUENCE: 3
gccttggcac ccgagaattc cannnnnnnn acatcgnnnn nn          42

<210> SEQ ID NO 4
<211> LENGTH: 42
<212> TYPE: DNA
<213> ORGANISM: Artificial Sequence
<220> FEATURE:
<223> OTHER INFORMATION: Reverse Transcription Primer 3
<220> FEATURE:
<221> NAME/KEY: misc_feature
<222> LOCATION: (23)..(30)
<223> OTHER INFORMATION: n is a, c, g, or t
<220> FEATURE:
<221> NAME/KEY: misc_feature
<222> LOCATION: (37)..(42)
<223> OTHER INFORMATION: n is a, c, g, or t

<400> SEQUENCE: 4
gccttggcac ccgagaattc cannnnnnnn gcctaannnn nn          42

<210> SEQ ID NO 5
<211> LENGTH: 42
<212> TYPE: DNA
<213> ORGANISM: Artificial Sequence
<220> FEATURE:
<223> OTHER INFORMATION: Reverse Transcription Primer 4
<220> FEATURE:
<221> NAME/KEY: misc_feature
<222> LOCATION: (23)..(30)
<223> OTHER INFORMATION: n is a, c, g, or t
<220> FEATURE:
<221> NAME/KEY: misc_feature
<222> LOCATION: (37)..(42)
<223> OTHER INFORMATION: n is a, c, g, or t

<400> SEQUENCE: 5
```
gccttggcac ccgagaattc cannnnnnnn tggtcannnn nn                          42

<210> SEQ ID NO 6
<211> LENGTH: 42
<212> TYPE: DNA
<213> ORGANISM: Artificial Sequence
<220> FEATURE:
<223> OTHER INFORMATION: Reverse Transcription Primer 5
<220> FEATURE:
<221> NAME/KEY: misc_feature
<222> LOCATION: (23)..(30)
<223> OTHER INFORMATION: n is a, c, g, or t
<220> FEATURE:
<221> NAME/KEY: misc_feature
<222> LOCATION: (37)..(42)
<223> OTHER INFORMATION: n is a, c, g, or t

<400> SEQUENCE: 6
gccttggcac ccgagaattc cannnnnnnn cactgtnnnn nn                          42

<210> SEQ ID NO 7
<211> LENGTH: 50
<212> TYPE: DNA
<213> ORGANISM: Artificial Sequence
<220> FEATURE:
<223> OTHER INFORMATION: RP1

<400> SEQUENCE: 7
aatgatacgg cgaccaccga gatctacacg ttcagagttc tacagtccga                  50

<210> SEQ ID NO 8
<211> LENGTH: 63
<212> TYPE: DNA
<213> ORGANISM: Artificial Sequence
<220> FEATURE:
<223> OTHER INFORMATION: RPI1

<400> SEQUENCE: 8
caagcagaag acggcatacg agatcgtgat gtgactggag ttccttggca cccgagaatt      60
cca                                                                    63

<210> SEQ ID NO 9
<211> LENGTH: 41
<212> TYPE: DNA
<213> ORGANISM: Artificial Sequence
<220> FEATURE:
<223> OTHER INFORMATION: FBC Oligo1

<400> SEQUENCE: 9
caggtcaacc agagagatcg tcggactgta gaactctgaa c                          41

<210> SEQ ID NO 10
<211> LENGTH: 41
<212> TYPE: DNA
<213> ORGANISM: Artificial Sequence
<220> FEATURE:
<223> OTHER INFORMATION: FBC_Oligo2

<400> SEQUENCE: 10
caggtcaaag tacgcgatcg tcggactgta gaactctgaa c                          41

<210> SEQ ID NO 11
<211> LENGTH: 41
<212> TYPE: DNA
<213> ORGANISM: Artificial Sequence
<220> FEATURE:

<223> OTHER INFORMATION: FBC_Oligo3

<400> SEQUENCE: 11
caggtcgttt ggcatgatcg tcggactgta gaactctgaa c                                    41

<210> SEQ ID NO 12
<211> LENGTH: 41
<212> TYPE: DNA
<213> ORGANISM: Artificial Sequence
<220> FEATURE:
<223> OTHER INFORMATION: FBC_Oligo4

<400> SEQUENCE: 12
caggtcaagt gaggtgatcg tcggactgta gaactctgaa c                                    41

<210> SEQ ID NO 13
<211> LENGTH: 41
<212> TYPE: DNA
<213> ORGANISM: Artificial Sequence
<220> FEATURE:
<223> OTHER INFORMATION: FBC_Oligo5

<400> SEQUENCE: 13
caggtcacgt tagctgatcg tcggactgta gaactctgaa c                                    41

<210> SEQ ID NO 14
<211> LENGTH: 41
<212> TYPE: DNA
<213> ORGANISM: Artificial Sequence
<220> FEATURE:
<223> OTHER INFORMATION: FBC_Oligo6

<400> SEQUENCE: 14
caggtcgtgc tagaggatcg tcggactgta gaactctgaa c                                    41

<210> SEQ ID NO 15
<211> LENGTH: 41
<212> TYPE: DNA
<213> ORGANISM: Artificial Sequence
<220> FEATURE:
<223> OTHER INFORMATION: FBC_Oligo7

<400> SEQUENCE: 15
caggtcgtcc tgtgtgatcg tcggactgta gaactctgaa c                                    41

<210> SEQ ID NO 16
<211> LENGTH: 41
<212> TYPE: DNA
<213> ORGANISM: Artificial Sequence
<220> FEATURE:
<223> OTHER INFORMATION: FBC_Oligo8

<400> SEQUENCE: 16
caggtctcta cggcagatcg tcggactgta gaactctgaa c                                    41

<210> SEQ ID NO 17
<211> LENGTH: 41
<212> TYPE: DNA
<213> ORGANISM: Artificial Sequence
<220> FEATURE:
<223> OTHER INFORMATION: FBC_Oligo9

<400> SEQUENCE: 17
caggtcacag ggcttgatcg tcggactgta gaactctgaa c                                    41

<210> SEQ ID NO 18
<211> LENGTH: 41
<212> TYPE: DNA
<213> ORGANISM: Artificial Sequence
<220> FEATURE:
<223> OTHER INFORMATION: FBC_Oligo10

<400> SEQUENCE: 18
caggtcgtgc gttatgatcg tcggactgta gaactctgaa c                    41

<210> SEQ ID NO 19
<211> LENGTH: 41
<212> TYPE: DNA
<213> ORGANISM: Artificial Sequence
<220> FEATURE:
<223> OTHER INFORMATION: FBC_Oligo11

<400> SEQUENCE: 19
caggtcgggt aagtagatcg tcggactgta gaactctgaa c                    41

<210> SEQ ID NO 20
<211> LENGTH: 41
<212> TYPE: DNA
<213> ORGANISM: Artificial Sequence
<220> FEATURE:
<223> OTHER INFORMATION: FBC_Oligo12

<400> SEQUENCE: 20
caggtctccc ttagggatcg tcggactgta gaactctgaa c                    41

<210> SEQ ID NO 21
<211> LENGTH: 41
<212> TYPE: DNA
<213> ORGANISM: Artificial Sequence
<220> FEATURE:
<223> OTHER INFORMATION: FBC_Oligo13

<400> SEQUENCE: 21
caggtccaag ttggtgatcg tcggactgta gaactctgaa c                    41

<210> SEQ ID NO 22
<211> LENGTH: 41
<212> TYPE: DNA
<213> ORGANISM: Artificial Sequence
<220> FEATURE:
<223> OTHER INFORMATION: FBC_Oligo14

<400> SEQUENCE: 22
caggtcttct cactcgatcg tcggactgta gaactctgaa c                    41

<210> SEQ ID NO 23
<211> LENGTH: 41
<212> TYPE: DNA
<213> ORGANISM: Artificial Sequence
<220> FEATURE:
<223> OTHER INFORMATION: FBC_Oligo15

<400> SEQUENCE: 23
caggtctccc actctgatcg tcggactgta gaactctgaa c                    41

<210> SEQ ID NO 24
<211> LENGTH: 41
<212> TYPE: DNA
<213> ORGANISM: Artificial Sequence
<220> FEATURE:
<223> OTHER INFORMATION: FBC_Oligo16

<400> SEQUENCE: 24
caggtccggt ataccgatcg tcggactgta gaactctgaa c                    41

<210> SEQ ID NO 25
<211> LENGTH: 41
<212> TYPE: DNA
<213> ORGANISM: Artificial Sequence
<220> FEATURE:
<223> OTHER INFORMATION: FBC_Oligo17

<400> SEQUENCE: 25
caggtcaggc atgtggatcg tcggactgta gaactctgaa c                    41

<210> SEQ ID NO 26
<211> LENGTH: 41
<212> TYPE: DNA
<213> ORGANISM: Artificial Sequence
<220> FEATURE:
<223> OTHER INFORMATION: FBC_Oligo18

<400> SEQUENCE: 26
caggtcccca gattggatcg tcggactgta gaactctgaa c                    41

<210> SEQ ID NO 27
<211> LENGTH: 41
<212> TYPE: DNA
<213> ORGANISM: Artificial Sequence
<220> FEATURE:
<223> OTHER INFORMATION: FBC_Oligo19

<400> SEQUENCE: 27
caggtcttcc cttgagatcg tcggactgta gaactctgaa c                    41

<210> SEQ ID NO 28
<211> LENGTH: 41
<212> TYPE: DNA
<213> ORGANISM: Artificial Sequence
<220> FEATURE:
<223> OTHER INFORMATION: FBC_Oligo20

<400> SEQUENCE: 28
caggtcgttg tacgagatcg tcggactgta gaactctgaa c                    41

<210> SEQ ID NO 29
<211> LENGTH: 41
<212> TYPE: DNA
<213> ORGANISM: Artificial Sequence
<220> FEATURE:
<223> OTHER INFORMATION: FBC_Oligo21

<400> SEQUENCE: 29
caggtctgct tgcaggatcg tcggactgta gaactctgaa c                    41

<210> SEQ ID NO 30
<211> LENGTH: 41
<212> TYPE: DNA
<213> ORGANISM: Artificial Sequence
<220> FEATURE:
<223> OTHER INFORMATION: FBC_Oligo22

<400> SEQUENCE: 30
caggtcggcc tcattgatcg tcggactgta gaactctgaa c                    41

<210> SEQ ID NO 31
<211> LENGTH: 41

```
<212> TYPE: DNA
<213> ORGANISM: Artificial Sequence
<220> FEATURE:
<223> OTHER INFORMATION: FBC_Oligo23

<400> SEQUENCE: 31
caggtcaaca gcctagatcg tcggactgta gaactctgaa c                   41

<210> SEQ ID NO 32
<211> LENGTH: 41
<212> TYPE: DNA
<213> ORGANISM: Artificial Sequence
<220> FEATURE:
<223> OTHER INFORMATION: FBC_Oligo24

<400> SEQUENCE: 32
caggtcgatg caatggatcg tcggactgta gaactctgaa c                   41

<210> SEQ ID NO 33
<211> LENGTH: 41
<212> TYPE: DNA
<213> ORGANISM: Artificial Sequence
<220> FEATURE:
<223> OTHER INFORMATION: FBC_Oligo25

<400> SEQUENCE: 33
caggtcgaag gaacggatcg tcggactgta gaactctgaa c                   41

<210> SEQ ID NO 34
<211> LENGTH: 41
<212> TYPE: DNA
<213> ORGANISM: Artificial Sequence
<220> FEATURE:
<223> OTHER INFORMATION: FBC_Oligo26

<400> SEQUENCE: 34
caggtccagc cacttgatcg tcggactgta gaactctgaa c                   41

<210> SEQ ID NO 35
<211> LENGTH: 41
<212> TYPE: DNA
<213> ORGANISM: Artificial Sequence
<220> FEATURE:
<223> OTHER INFORMATION: FBC_Oligo27

<400> SEQUENCE: 35
caggtcctct gcttcgatcg tcggactgta gaactctgaa c                   41

<210> SEQ ID NO 36
<211> LENGTH: 41
<212> TYPE: DNA
<213> ORGANISM: Artificial Sequence
<220> FEATURE:
<223> OTHER INFORMATION: FBC_Oligo28

<400> SEQUENCE: 36
caggtcggct tatgagatcg tcggactgta gaactctgaa c                   41

<210> SEQ ID NO 37
<211> LENGTH: 41
<212> TYPE: DNA
<213> ORGANISM: Artificial Sequence
<220> FEATURE:
<223> OTHER INFORMATION: FBC_Oligo29

<400> SEQUENCE: 37
```

-continued

```
caggtcctag tcctcgatcg tcggactgta gaactctgaa c                    41

<210> SEQ ID NO 38
<211> LENGTH: 41
<212> TYPE: DNA
<213> ORGANISM: Artificial Sequence
<220> FEATURE:
<223> OTHER INFORMATION: FBC_Oligo30

<400> SEQUENCE: 38
caggtcctag aggaggatcg tcggactgta gaactctgaa c                    41

<210> SEQ ID NO 39
<211> LENGTH: 41
<212> TYPE: DNA
<213> ORGANISM: Artificial Sequence
<220> FEATURE:
<223> OTHER INFORMATION: FBC_Oligo31

<400> SEQUENCE: 39
caggtcagct ttaccgatcg tcggactgta gaactctgaa c                    41

<210> SEQ ID NO 40
<211> LENGTH: 41
<212> TYPE: DNA
<213> ORGANISM: Artificial Sequence
<220> FEATURE:
<223> OTHER INFORMATION: FBC_Oligo32

<400> SEQUENCE: 40
caggtcgtcc atgaagatcg tcggactgta gaactctgaa c                    41

<210> SEQ ID NO 41
<211> LENGTH: 41
<212> TYPE: DNA
<213> ORGANISM: Artificial Sequence
<220> FEATURE:
<223> OTHER INFORMATION: FBC_Oligo33

<400> SEQUENCE: 41
caggtcctcg aacctgatcg tcggactgta gaactctgaa c                    41

<210> SEQ ID NO 42
<211> LENGTH: 41
<212> TYPE: DNA
<213> ORGANISM: Artificial Sequence
<220> FEATURE:
<223> OTHER INFORMATION: FBC_Oligo34

<400> SEQUENCE: 42
caggtccatt gtacggatcg tcggactgta gaactctgaa c                    41

<210> SEQ ID NO 43
<211> LENGTH: 41
<212> TYPE: DNA
<213> ORGANISM: Artificial Sequence
<220> FEATURE:
<223> OTHER INFORMATION: FBC_Oligo35

<400> SEQUENCE: 43
caggtcttga acgctgatcg tcggactgta gaactctgaa c                    41

<210> SEQ ID NO 44
<211> LENGTH: 41
<212> TYPE: DNA
<213> ORGANISM: Artificial Sequence
```

-continued

```
<220> FEATURE:
<223> OTHER INFORMATION: FBC_Oligo36

<400> SEQUENCE: 44
caggtctacg tcatggatcg tcggactgta gaactctgaa c                        41

<210> SEQ ID NO 45
<211> LENGTH: 41
<212> TYPE: DNA
<213> ORGANISM: Artificial Sequence
<220> FEATURE:
<223> OTHER INFORMATION: FBC_Oligo37

<400> SEQUENCE: 45
caggtcaagc cgttagatcg tcggactgta gaactctgaa c                        41

<210> SEQ ID NO 46
<211> LENGTH: 41
<212> TYPE: DNA
<213> ORGANISM: Artificial Sequence
<220> FEATURE:
<223> OTHER INFORMATION: FBC_Oligo38

<400> SEQUENCE: 46
caggtccgga cgtatgatcg tcggactgta gaactctgaa c                        41

<210> SEQ ID NO 47
<211> LENGTH: 41
<212> TYPE: DNA
<213> ORGANISM: Artificial Sequence
<220> FEATURE:
<223> OTHER INFORMATION: FBC_Oligo39

<400> SEQUENCE: 47
caggtctcgt taccggatcg tcggactgta gaactctgaa c                        41

<210> SEQ ID NO 48
<211> LENGTH: 41
<212> TYPE: DNA
<213> ORGANISM: Artificial Sequence
<220> FEATURE:
<223> OTHER INFORMATION: FBC_Oligo40

<400> SEQUENCE: 48
caggtcatcc cccatgatcg tcggactgta gaactctgaa c                        41

<210> SEQ ID NO 49
<211> LENGTH: 41
<212> TYPE: DNA
<213> ORGANISM: Artificial Sequence
<220> FEATURE:
<223> OTHER INFORMATION: FBC_Oligo41

<400> SEQUENCE: 49
caggtccaga cgattgatcg tcggactgta gaactctgaa c                        41

<210> SEQ ID NO 50
<211> LENGTH: 41
<212> TYPE: DNA
<213> ORGANISM: Artificial Sequence
<220> FEATURE:
<223> OTHER INFORMATION: FBC_Oligo42

<400> SEQUENCE: 50
caggtcatcg atcccgatcg tcggactgta gaactctgaa c                        41
```

<210> SEQ ID NO 51
<211> LENGTH: 41
<212> TYPE: DNA
<213> ORGANISM: Artificial Sequence
<220> FEATURE:
<223> OTHER INFORMATION: FBC_Oligo43

<400> SEQUENCE: 51
caggtccctg aggatgatcg tcggactgta gaactctgaa c                     41

<210> SEQ ID NO 52
<211> LENGTH: 41
<212> TYPE: DNA
<213> ORGANISM: Artificial Sequence
<220> FEATURE:
<223> OTHER INFORMATION: FBC_Oligo44

<400> SEQUENCE: 52
caggtcagct ctttggatcg tcggactgta gaactctgaa c                     41

<210> SEQ ID NO 53
<211> LENGTH: 41
<212> TYPE: DNA
<213> ORGANISM: Artificial Sequence
<220> FEATURE:
<223> OTHER INFORMATION: FBC_Oligo45

<400> SEQUENCE: 53
caggtcggaa tacgggatcg tcggactgta gaactctgaa c                     41

<210> SEQ ID NO 54
<211> LENGTH: 41
<212> TYPE: DNA
<213> ORGANISM: Artificial Sequence
<220> FEATURE:
<223> OTHER INFORMATION: FBC_Oligo46

<400> SEQUENCE: 54
caggtcctat cctgggatcg tcggactgta gaactctgaa c                     41

<210> SEQ ID NO 55
<211> LENGTH: 41
<212> TYPE: DNA
<213> ORGANISM: Artificial Sequence
<220> FEATURE:
<223> OTHER INFORMATION: FBC_Oligo47

<400> SEQUENCE: 55
caggtcggtt gtagtgatcg tcggactgta gaactctgaa c                     41

<210> SEQ ID NO 56
<211> LENGTH: 41
<212> TYPE: DNA
<213> ORGANISM: Artificial Sequence
<220> FEATURE:
<223> OTHER INFORMATION: FBC_Oligo48

<400> SEQUENCE: 56
caggtcgaac gtagcgatcg tcggactgta gaactctgaa c                     41

<210> SEQ ID NO 57
<211> LENGTH: 40
<212> TYPE: DNA
<213> ORGANISM: Artificial Sequence
<220> FEATURE:
<223> OTHER INFORMATION: FBC_Oligo49

```
<400> SEQUENCE: 57
caggtcgtct atcggatcgt cggactgtag aactctgaac                              40

<210> SEQ ID NO 58
<211> LENGTH: 40
<212> TYPE: DNA
<213> ORGANISM: Artificial Sequence
<220> FEATURE:
<223> OTHER INFORMATION: FBC_Oligo50

<400> SEQUENCE: 58
caggtctacg agtggatcgt cggactgtag aactctgaac                              40

<210> SEQ ID NO 59
<211> LENGTH: 40
<212> TYPE: DNA
<213> ORGANISM: Artificial Sequence
<220> FEATURE:
<223> OTHER INFORMATION: FBC_Oligo51

<400> SEQUENCE: 59
caggtctcat gtcggatcgt cggactgtag aactctgaac                              40

<210> SEQ ID NO 60
<211> LENGTH: 40
<212> TYPE: DNA
<213> ORGANISM: Artificial Sequence
<220> FEATURE:
<223> OTHER INFORMATION: FBC_Oligo52

<400> SEQUENCE: 60
caggtcaaac acccgatcgt cggactgtag aactctgaac                              40

<210> SEQ ID NO 61
<211> LENGTH: 40
<212> TYPE: DNA
<213> ORGANISM: Artificial Sequence
<220> FEATURE:
<223> OTHER INFORMATION: FBC_Oligo53

<400> SEQUENCE: 61
caggtcacta gtccgatcgt cggactgtag aactctgaac                              40

<210> SEQ ID NO 62
<211> LENGTH: 40
<212> TYPE: DNA
<213> ORGANISM: Artificial Sequence
<220> FEATURE:
<223> OTHER INFORMATION: FBC_Oligo54

<400> SEQUENCE: 62
caggtccgag gaatgatcgt cggactgtag aactctgaac                              40

<210> SEQ ID NO 63
<211> LENGTH: 40
<212> TYPE: DNA
<213> ORGANISM: Artificial Sequence
<220> FEATURE:
<223> OTHER INFORMATION: FBC_Oligo55

<400> SEQUENCE: 63
caggtcacaa tggcgatcgt cggactgtag aactctgaac                              40

<210> SEQ ID NO 64
```

```
<211> LENGTH: 40
<212> TYPE: DNA
<213> ORGANISM: Artificial Sequence
<220> FEATURE:
<223> OTHER INFORMATION: FBC_Oligo56

<400> SEQUENCE: 64
caggtctagg tctcgatcgt cggactgtag aactctgaac                              40

<210> SEQ ID NO 65
<211> LENGTH: 40
<212> TYPE: DNA
<213> ORGANISM: Artificial Sequence
<220> FEATURE:
<223> OTHER INFORMATION: FBC_Oligo57

<400> SEQUENCE: 65
caggtctctg tgaggatcgt cggactgtag aactctgaac                              40

<210> SEQ ID NO 66
<211> LENGTH: 40
<212> TYPE: DNA
<213> ORGANISM: Artificial Sequence
<220> FEATURE:
<223> OTHER INFORMATION: FBC_Oligo58

<400> SEQUENCE: 66
caggtcggga ttgagatcgt cggactgtag aactctgaac                              40

<210> SEQ ID NO 67
<211> LENGTH: 40
<212> TYPE: DNA
<213> ORGANISM: Artificial Sequence
<220> FEATURE:
<223> OTHER INFORMATION: FBC_Oligo59

<400> SEQUENCE: 67
caggtcaact ctgggatcgt cggactgtag aactctgaac                              40

<210> SEQ ID NO 68
<211> LENGTH: 40
<212> TYPE: DNA
<213> ORGANISM: Artificial Sequence
<220> FEATURE:
<223> OTHER INFORMATION: FBC_Oligo60

<400> SEQUENCE: 68
caggtcaaac gcgtgatcgt cggactgtag aactctgaac                              40

<210> SEQ ID NO 69
<211> LENGTH: 40
<212> TYPE: DNA
<213> ORGANISM: Artificial Sequence
<220> FEATURE:
<223> OTHER INFORMATION: FBC_Oligo61

<400> SEQUENCE: 69
caggtctcct acgagatcgt cggactgtag aactctgaac                              40

<210> SEQ ID NO 70
<211> LENGTH: 40
<212> TYPE: DNA
<213> ORGANISM: Artificial Sequence
<220> FEATURE:
<223> OTHER INFORMATION: FBC_Oligo62

<400> SEQUENCE: 70
```

-continued

```
caggtctagc aggtgatcgt cggactgtag aactctgaac                    40

<210> SEQ ID NO 71
<211> LENGTH: 40
<212> TYPE: DNA
<213> ORGANISM: Artificial Sequence
<220> FEATURE:
<223> OTHER INFORMATION: FBC_Oligo63

<400> SEQUENCE: 71
caggtccctg cattgatcgt cggactgtag aactctgaac                    40

<210> SEQ ID NO 72
<211> LENGTH: 40
<212> TYPE: DNA
<213> ORGANISM: Artificial Sequence
<220> FEATURE:
<223> OTHER INFORMATION: FBC_Oligo64

<400> SEQUENCE: 72
caggtcgtga tgcagatcgt cggactgtag aactctgaac                    40

<210> SEQ ID NO 73
<211> LENGTH: 40
<212> TYPE: DNA
<213> ORGANISM: Artificial Sequence
<220> FEATURE:
<223> OTHER INFORMATION: FBC_Oligo65

<400> SEQUENCE: 73
caggtccgat tcaggatcgt cggactgtag aactctgaac                    40

<210> SEQ ID NO 74
<211> LENGTH: 40
<212> TYPE: DNA
<213> ORGANISM: Artificial Sequence
<220> FEATURE:
<223> OTHER INFORMATION: FBC_Oligo66

<400> SEQUENCE: 74
caggtcagga tgacgatcgt cggactgtag aactctgaac                    40

<210> SEQ ID NO 75
<211> LENGTH: 40
<212> TYPE: DNA
<213> ORGANISM: Artificial Sequence
<220> FEATURE:
<223> OTHER INFORMATION: FBC_Oligo67

<400> SEQUENCE: 75
caggtcaggc catagatcgt cggactgtag aactctgaac                    40

<210> SEQ ID NO 76
<211> LENGTH: 40
<212> TYPE: DNA
<213> ORGANISM: Artificial Sequence
<220> FEATURE:
<223> OTHER INFORMATION: FBC_Oligo68

<400> SEQUENCE: 76
caggtcgctt gcttgatcgt cggactgtag aactctgaac                    40

<210> SEQ ID NO 77
<211> LENGTH: 40
<212> TYPE: DNA
```

-continued

<213> ORGANISM: Artificial Sequence
<220> FEATURE:
<223> OTHER INFORMATION: FBC_Oligo69

<400> SEQUENCE: 77
caggtctccc aagtgatcgt cggactgtag aactctgaac                          40

<210> SEQ ID NO 78
<211> LENGTH: 40
<212> TYPE: DNA
<213> ORGANISM: Artificial Sequence
<220> FEATURE:
<223> OTHER INFORMATION: FBC_Oligo70

<400> SEQUENCE: 78
caggtctcaa ggcagatcgt cggactgtag aactctgaac                          40

<210> SEQ ID NO 79
<211> LENGTH: 40
<212> TYPE: DNA
<213> ORGANISM: Artificial Sequence
<220> FEATURE:
<223> OTHER INFORMATION: FBC_Oligo71

<400> SEQUENCE: 79
caggtcacga ggtagatcgt cggactgtag aactctgaac                          40

<210> SEQ ID NO 80
<211> LENGTH: 40
<212> TYPE: DNA
<213> ORGANISM: Artificial Sequence
<220> FEATURE:
<223> OTHER INFORMATION: FBC_Oligo72

<400> SEQUENCE: 80
caggtcggaa cgaagatcgt cggactgtag aactctgaac                          40

<210> SEQ ID NO 81
<211> LENGTH: 40
<212> TYPE: DNA
<213> ORGANISM: Artificial Sequence
<220> FEATURE:
<223> OTHER INFORMATION: FBC_Oligo73

<400> SEQUENCE: 81
caggtcaatc ccaggatcgt cggactgtag aactctgaac                          40

<210> SEQ ID NO 82
<211> LENGTH: 40
<212> TYPE: DNA
<213> ORGANISM: Artificial Sequence
<220> FEATURE:
<223> OTHER INFORMATION: FBC_Oligo74

<400> SEQUENCE: 82
caggtccgat aagggatcgt cggactgtag aactctgaac                          40

<210> SEQ ID NO 83
<211> LENGTH: 40
<212> TYPE: DNA
<213> ORGANISM: Artificial Sequence
<220> FEATURE:
<223> OTHER INFORMATION: FBC_Oligo75

<400> SEQUENCE: 83
caggtctatc gcgagatcgt cggactgtag aactctgaac                          40

-continued

```
<210> SEQ ID NO 84
<211> LENGTH: 40
<212> TYPE: DNA
<213> ORGANISM: Artificial Sequence
<220> FEATURE:
<223> OTHER INFORMATION: FBC_Oligo76

<400> SEQUENCE: 84
caggtccgca taacgatcgt cggactgtag aactctgaac                              40

<210> SEQ ID NO 85
<211> LENGTH: 40
<212> TYPE: DNA
<213> ORGANISM: Artificial Sequence
<220> FEATURE:
<223> OTHER INFORMATION: FBC_Oligo77

<400> SEQUENCE: 85
caggtcgtgc agttgatcgt cggactgtag aactctgaac                              40

<210> SEQ ID NO 86
<211> LENGTH: 40
<212> TYPE: DNA
<213> ORGANISM: Artificial Sequence
<220> FEATURE:
<223> OTHER INFORMATION: FBC_Oligo78

<400> SEQUENCE: 86
caggtcagaa cgctgatcgt cggactgtag aactctgaac                              40

<210> SEQ ID NO 87
<211> LENGTH: 40
<212> TYPE: DNA
<213> ORGANISM: Artificial Sequence
<220> FEATURE:
<223> OTHER INFORMATION: FBC_Oligo79

<400> SEQUENCE: 87
caggtctaga ggtcgatcgt cggactgtag aactctgaac                              40

<210> SEQ ID NO 88
<211> LENGTH: 40
<212> TYPE: DNA
<213> ORGANISM: Artificial Sequence
<220> FEATURE:
<223> OTHER INFORMATION: FBC_Oligo80

<400> SEQUENCE: 88
caggtcctgt gatggatcgt cggactgtag aactctgaac                              40

<210> SEQ ID NO 89
<211> LENGTH: 40
<212> TYPE: DNA
<213> ORGANISM: Artificial Sequence
<220> FEATURE:
<223> OTHER INFORMATION: FBC_Oligo81

<400> SEQUENCE: 89
caggtctaga gccagatcgt cggactgtag aactctgaac                              40

<210> SEQ ID NO 90
<211> LENGTH: 40
<212> TYPE: DNA
<213> ORGANISM: Artificial Sequence
<220> FEATURE:
```

-continued

<223> OTHER INFORMATION: FBC_Oligo82

<400> SEQUENCE: 90
caggtccttg atgcgatcgt cggactgtag aactctgaac                                    40

<210> SEQ ID NO 91
<211> LENGTH: 40
<212> TYPE: DNA
<213> ORGANISM: Artificial Sequence
<220> FEATURE:
<223> OTHER INFORMATION: FBC_Oligo83

<400> SEQUENCE: 91
caggtcttcg tgtcgatcgt cggactgtag aactctgaac                                    40

<210> SEQ ID NO 92
<211> LENGTH: 40
<212> TYPE: DNA
<213> ORGANISM: Artificial Sequence
<220> FEATURE:
<223> OTHER INFORMATION: FBC_Oligo84

<400> SEQUENCE: 92
caggtctatc tgcggatcgt cggactgtag aactctgaac                                    40

<210> SEQ ID NO 93
<211> LENGTH: 40
<212> TYPE: DNA
<213> ORGANISM: Artificial Sequence
<220> FEATURE:
<223> OTHER INFORMATION: FBC_Oligo85

<400> SEQUENCE: 93
caggtctggt aggagatcgt cggactgtag aactctgaac                                    40

<210> SEQ ID NO 94
<211> LENGTH: 40
<212> TYPE: DNA
<213> ORGANISM: Artificial Sequence
<220> FEATURE:
<223> OTHER INFORMATION: FBC_Oligo86

<400> SEQUENCE: 94
caggtcccta gacagatcgt cggactgtag aactctgaac                                    40

<210> SEQ ID NO 95
<211> LENGTH: 40
<212> TYPE: DNA
<213> ORGANISM: Artificial Sequence
<220> FEATURE:
<223> OTHER INFORMATION: FBC_Oligo87

<400> SEQUENCE: 95
caggtcagtc aacggatcgt cggactgtag aactctgaac                                    40

<210> SEQ ID NO 96
<211> LENGTH: 40
<212> TYPE: DNA
<213> ORGANISM: Artificial Sequence
<220> FEATURE:
<223> OTHER INFORMATION: FBC_Oligo88

<400> SEQUENCE: 96
caggtcaagg gtgagatcgt cggactgtag aactctgaac                                    40

```
<210> SEQ ID NO 97
<211> LENGTH: 40
<212> TYPE: DNA
<213> ORGANISM: Artificial Sequence
<220> FEATURE:
<223> OTHER INFORMATION: FBC_Oligo89

<400> SEQUENCE: 97
caggtccttc acacgatcgt cggactgtag aactctgaac                              40

<210> SEQ ID NO 98
<211> LENGTH: 40
<212> TYPE: DNA
<213> ORGANISM: Artificial Sequence
<220> FEATURE:
<223> OTHER INFORMATION: FBC_Oligo90

<400> SEQUENCE: 98
caggtcaggt tgctgatcgt cggactgtag aactctgaac                              40

<210> SEQ ID NO 99
<211> LENGTH: 40
<212> TYPE: DNA
<213> ORGANISM: Artificial Sequence
<220> FEATURE:
<223> OTHER INFORMATION: FBC_Oligo91

<400> SEQUENCE: 99
caggtcaccc gaaagatcgt cggactgtag aactctgaac                              40

<210> SEQ ID NO 100
<211> LENGTH: 40
<212> TYPE: DNA
<213> ORGANISM: Artificial Sequence
<220> FEATURE:
<223> OTHER INFORMATION: FBC_Oligo92

<400> SEQUENCE: 100
caggtcgaaa aggggatcgt cggactgtag aactctgaac                              40

<210> SEQ ID NO 101
<211> LENGTH: 40
<212> TYPE: DNA
<213> ORGANISM: Artificial Sequence
<220> FEATURE:
<223> OTHER INFORMATION: FBC_Oligo93

<400> SEQUENCE: 101
caggtcactt cccagatcgt cggactgtag aactctgaac                              40

<210> SEQ ID NO 102
<211> LENGTH: 40
<212> TYPE: DNA
<213> ORGANISM: Artificial Sequence
<220> FEATURE:
<223> OTHER INFORMATION: FBC_Oligo94

<400> SEQUENCE: 102
caggtctgct gcatgatcgt cggactgtag aactctgaac                              40

<210> SEQ ID NO 103
<211> LENGTH: 40
<212> TYPE: DNA
<213> ORGANISM: Artificial Sequence
<220> FEATURE:
<223> OTHER INFORMATION: FBC_Oligo95
```

```
<400> SEQUENCE: 103
caggtcattc ctgggatcgt cggactgtag aactctgaac                              40

<210> SEQ ID NO 104
<211> LENGTH: 40
<212> TYPE: DNA
<213> ORGANISM: Artificial Sequence
<220> FEATURE:
<223> OTHER INFORMATION: FBC_Oligo96

<400> SEQUENCE: 104
caggtccaga actcgatcgt cggactgtag aactctgaac                              40

<210> SEQ ID NO 105
<211> LENGTH: 68
<212> TYPE: DNA
<213> ORGANISM: Artificial Sequence
<220> FEATURE:
<223> OTHER INFORMATION: SBC_Oligo1

<400> SEQUENCE: 105
aaaaaaaaaa aaaaaaaaaa aaaaaggtga tacaggtcaa aaaaaaagat cgtcggactg        60
tagaactc                                                                 68

<210> SEQ ID NO 106
<211> LENGTH: 68
<212> TYPE: DNA
<213> ORGANISM: Artificial Sequence
<220> FEATURE:
<223> OTHER INFORMATION: SBC_Oligo2

<400> SEQUENCE: 106
aaaaaaaaaa aaaaaaaaaa aaaatgaat gccaggtcaa aaaaaaagat cgtcggactg         60
tagaactc                                                                 68

<210> SEQ ID NO 107
<211> LENGTH: 68
<212> TYPE: DNA
<213> ORGANISM: Artificial Sequence
<220> FEATURE:
<223> OTHER INFORMATION: SBC_Oligo3

<400> SEQUENCE: 107
aaaaaaaaaa aaaaaaaaaa aaaatgcca acaggtcaa aaaaaaagat cgtcggactg          60
tagaactc                                                                 68

<210> SEQ ID NO 108
<211> LENGTH: 68
<212> TYPE: DNA
<213> ORGANISM: Artificial Sequence
<220> FEATURE:
<223> OTHER INFORMATION: SBC_Oligo4

<400> SEQUENCE: 108
aaaaaaaaaa aaaaaaaaaa aaaaacaga agcaggtcaa aaaaaaagat cgtcggactg         60
tagaactc                                                                 68

<210> SEQ ID NO 109
<211> LENGTH: 68
<212> TYPE: DNA
<213> ORGANISM: Artificial Sequence
<220> FEATURE:
<223> OTHER INFORMATION: SBC_Oligo5
```

-continued

```
<400> SEQUENCE: 109
aaaaaaaaaa aaaaaaaaaa aaaaacactg gacaggtcaa aaaaaaagat cgtcggactg     60
tagaactc                                                              68

<210> SEQ ID NO 110
<211> LENGTH: 68
<212> TYPE: DNA
<213> ORGANISM: Artificial Sequence
<220> FEATURE:
<223> OTHER INFORMATION: SBC_Oligo6

<400> SEQUENCE: 110
aaaaaaaaaa aaaaaaaaaa aaaaacgatg atcaggtcaa aaaaaaagat cgtcggactg     60
tagaactc                                                              68

<210> SEQ ID NO 111
<211> LENGTH: 68
<212> TYPE: DNA
<213> ORGANISM: Artificial Sequence
<220> FEATURE:
<223> OTHER INFORMATION: SBC_Oligo7

<400> SEQUENCE: 111
aaaaaaaaaa aaaaaaaaaa aaaaagtgtc cacaggtcaa aaaaaaagat cgtcggactg     60
tagaactc                                                              68

<210> SEQ ID NO 112
<211> LENGTH: 68
<212> TYPE: DNA
<213> ORGANISM: Artificial Sequence
<220> FEATURE:
<223> OTHER INFORMATION: SBC_Oligo8

<400> SEQUENCE: 112
aaaaaaaaaa aaaaaaaaaa aaaaatcctc ttcaggtcaa aaaaaaagat cgtcggactg     60
tagaactc                                                              68

<210> SEQ ID NO 113
<211> LENGTH: 68
<212> TYPE: DNA
<213> ORGANISM: Artificial Sequence
<220> FEATURE:
<223> OTHER INFORMATION: SBC_Oligo9

<400> SEQUENCE: 113
aaaaaaaaaa aaaaaaaaaa aaaaagtgca gtcaggtcaa aaaaaaagat cgtcggactg     60
tagaactc                                                              68

<210> SEQ ID NO 114
<211> LENGTH: 68
<212> TYPE: DNA
<213> ORGANISM: Artificial Sequence
<220> FEATURE:
<223> OTHER INFORMATION: SBC_Oligo10

<400> SEQUENCE: 114
aaaaaaaaaa aaaaaaaaaa aaaaaaggta gacaggtcaa aaaaaaagat cgtcggactg     60
tagaactc                                                              68

<210> SEQ ID NO 115
```

```
<211> LENGTH: 54
<212> TYPE: DNA
<213> ORGANISM: Artificial Sequence
<220> FEATURE:
<223> OTHER INFORMATION: Bead Capture Oligo

<400> SEQUENCE: 115
aggtaaggta atacgactca ctataggggt tcagagttct acagtccgac gatc          54

<210> SEQ ID NO 116
<211> LENGTH: 42
<212> TYPE: DNA
<213> ORGANISM: Artificial Sequence
<220> FEATURE:
<223> OTHER INFORMATION: RT1
<220> FEATURE:
<221> NAME/KEY: misc_feature
<222> LOCATION: (23)..(30)
<223> OTHER INFORMATION: n is a, c, g, or t
<220> FEATURE:
<221> NAME/KEY: misc_feature
<222> LOCATION: (37)..(42)
<223> OTHER INFORMATION: n is a, c, g, or t

<400> SEQUENCE: 116
gccttggcac ccgagaattc cannnnnnnn cgtcatnnnn nn          42

<210> SEQ ID NO 117
<211> LENGTH: 42
<212> TYPE: DNA
<213> ORGANISM: Artificial Sequence
<220> FEATURE:
<223> OTHER INFORMATION: RT2
<220> FEATURE:
<221> NAME/KEY: misc_feature
<222> LOCATION: (23)..(30)
<223> OTHER INFORMATION: n is a, c, g, or t
<220> FEATURE:
<221> NAME/KEY: misc_feature
<222> LOCATION: (37)..(42)
<223> OTHER INFORMATION: n is a, c, g, or t

<400> SEQUENCE: 117
gccttggcac ccgagaattc cannnnnnnn tacccannnn nn          42

<210> SEQ ID NO 118
<211> LENGTH: 42
<212> TYPE: DNA
<213> ORGANISM: Artificial Sequence
<220> FEATURE:
<223> OTHER INFORMATION: RT3
<220> FEATURE:
<221> NAME/KEY: misc_feature
<222> LOCATION: (23)..(30)
<223> OTHER INFORMATION: n is a, c, g, or t
<220> FEATURE:
<221> NAME/KEY: misc_feature
<222> LOCATION: (37)..(42)
<223> OTHER INFORMATION: n is a, c, g, or t

<400> SEQUENCE: 118
gccttggcac ccgagaattc cannnnnnnn gccattnnnn nn          42

<210> SEQ ID NO 119
<211> LENGTH: 42
<212> TYPE: DNA
<213> ORGANISM: Artificial Sequence
<220> FEATURE:
<223> OTHER INFORMATION: RT4
<220> FEATURE:
<221> NAME/KEY: misc_feature
```

```
<222> LOCATION: (23)..(30)
<223> OTHER INFORMATION: n is a, c, g, or t
<220> FEATURE:
<221> NAME/KEY: misc_feature
<222> LOCATION: (37)..(42)
<223> OTHER INFORMATION: n is a, c, g, or t

<400> SEQUENCE: 119
gccttggcac ccgagaattc cannnnnnnn gagtacnnnn nn                    42

<210> SEQ ID NO 120
<211> LENGTH: 42
<212> TYPE: DNA
<213> ORGANISM: Artificial Sequence
<220> FEATURE:
<223> OTHER INFORMATION: RT5
<220> FEATURE:
<221> NAME/KEY: misc_feature
<222> LOCATION: (23)..(30)
<223> OTHER INFORMATION: n is a, c, g, or t
<220> FEATURE:
<221> NAME/KEY: misc_feature
<222> LOCATION: (37)..(42)
<223> OTHER INFORMATION: n is a, c, g, or t

<400> SEQUENCE: 120
gccttggcac ccgagaattc cannnnnnnn agagtcnnnn nn                    42

<210> SEQ ID NO 121
<211> LENGTH: 50
<212> TYPE: DNA
<213> ORGANISM: Artificial Sequence
<220> FEATURE:
<223> OTHER INFORMATION: RP1

<400> SEQUENCE: 121
aatgatacgg cgaccaccga gatctacacg ttcagagttc tacagtccga           50

<210> SEQ ID NO 122
<211> LENGTH: 63
<212> TYPE: DNA
<213> ORGANISM: Artificial Sequence
<220> FEATURE:
<223> OTHER INFORMATION: RPI2

<400> SEQUENCE: 122
caagcagaag acggcatacg agatacatcg gtgactggag ttccttggca cccgagaatt  60
cca                                                              63

<210> SEQ ID NO 123
<211> LENGTH: 41
<212> TYPE: DNA
<213> ORGANISM: Artificial Sequence
<220> FEATURE:
<223> OTHER INFORMATION: FBC_Oligo1

<400> SEQUENCE: 123
caggtcctga tcgatgatcg tcggactgta gaactctgaa c                    41

<210> SEQ ID NO 124
<211> LENGTH: 41
<212> TYPE: DNA
<213> ORGANISM: Artificial Sequence
<220> FEATURE:
<223> OTHER INFORMATION: FBC_Oligo2

<400> SEQUENCE: 124
```
caggtcgtgt agacagatcg tcggactgta gaactctgaa c                          41

<210> SEQ ID NO 125
<211> LENGTH: 41
<212> TYPE: DNA
<213> ORGANISM: Artificial Sequence
<220> FEATURE:
<223> OTHER INFORMATION: FBC_Oligo3

<400> SEQUENCE: 125
caggtccatt gttccgatcg tcggactgta gaactctgaa c                          41

<210> SEQ ID NO 126
<211> LENGTH: 41
<212> TYPE: DNA
<213> ORGANISM: Artificial Sequence
<220> FEATURE:
<223> OTHER INFORMATION: FBC_Oligo4

<400> SEQUENCE: 126
caggtccttg actacgatcg tcggactgta gaactctgaa c                          41

<210> SEQ ID NO 127
<211> LENGTH: 41
<212> TYPE: DNA
<213> ORGANISM: Artificial Sequence
<220> FEATURE:
<223> OTHER INFORMATION: FBC_Oligo5

<400> SEQUENCE: 127
caggtcaccg tttcggatcg tcggactgta gaactctgaa c                          41

<210> SEQ ID NO 128
<211> LENGTH: 41
<212> TYPE: DNA
<213> ORGANISM: Artificial Sequence
<220> FEATURE:
<223> OTHER INFORMATION: FBC_Oligo6

<400> SEQUENCE: 128
caggtcaagg accgtgatcg tcggactgta gaactctgaa c                          41

<210> SEQ ID NO 129
<211> LENGTH: 41
<212> TYPE: DNA
<213> ORGANISM: Artificial Sequence
<220> FEATURE:
<223> OTHER INFORMATION: FBC_Oligo7

<400> SEQUENCE: 129
caggtctcac tatgcgatcg tcggactgta gaactctgaa c                          41

<210> SEQ ID NO 130
<211> LENGTH: 41
<212> TYPE: DNA
<213> ORGANISM: Artificial Sequence
<220> FEATURE:
<223> OTHER INFORMATION: FBC_Oligo8

<400> SEQUENCE: 130
caggtcctgc aatgggatcg tcggactgta gaactctgaa c                          41

<210> SEQ ID NO 131
<211> LENGTH: 41
<212> TYPE: DNA
<213> ORGANISM: Artificial Sequence
<220> FEATURE:
<223> OTHER INFORMATION: FBC_Oligo9

<400> SEQUENCE: 131
caggtctgag tcgtcgatcg tcggactgta gaactctgaa c                    41

<210> SEQ ID NO 132
<211> LENGTH: 41
<212> TYPE: DNA
<213> ORGANISM: Artificial Sequence
<220> FEATURE:
<223> OTHER INFORMATION: FBC_Oligo10

<400> SEQUENCE: 132
caggtcctca cactagatcg tcggactgta gaactctgaa c                    41

<210> SEQ ID NO 133
<211> LENGTH: 41
<212> TYPE: DNA
<213> ORGANISM: Artificial Sequence
<220> FEATURE:
<223> OTHER INFORMATION: FBC_Oligo11

<400> SEQUENCE: 133
caggtcttac cccctgatcg tcggactgta gaactctgaa c                    41

<210> SEQ ID NO 134
<211> LENGTH: 41
<212> TYPE: DNA
<213> ORGANISM: Artificial Sequence
<220> FEATURE:
<223> OTHER INFORMATION: FBC_Oligo12

<400> SEQUENCE: 134
caggtcccaa gtagagatcg tcggactgta gaactctgaa c                    41

<210> SEQ ID NO 135
<211> LENGTH: 41
<212> TYPE: DNA
<213> ORGANISM: Artificial Sequence
<220> FEATURE:
<223> OTHER INFORMATION: FBC_Oligo13

<400> SEQUENCE: 135
caggtcatag cgcacgatcg tcggactgta gaactctgaa c                    41

<210> SEQ ID NO 136
<211> LENGTH: 41
<212> TYPE: DNA
<213> ORGANISM: Artificial Sequence
<220> FEATURE:
<223> OTHER INFORMATION: FBC_Oligo14

<400> SEQUENCE: 136
caggtctgac gtacggatcg tcggactgta gaactctgaa c                    41

<210> SEQ ID NO 137
<211> LENGTH: 41
<212> TYPE: DNA
<213> ORGANISM: Artificial Sequence
<220> FEATURE:
<223> OTHER INFORMATION: FBC_Oligo15

<400> SEQUENCE: 137
caggtcgtag agttggatcg tcggactgta gaactctgaa c                    41

-continued

<210> SEQ ID NO 138
<211> LENGTH: 41
<212> TYPE: DNA
<213> ORGANISM: Artificial Sequence
<220> FEATURE:
<223> OTHER INFORMATION: FBC_Oligo16

<400> SEQUENCE: 138
caggtctttc tggcggatcg tcggactgta gaactctgaa c                          41

<210> SEQ ID NO 139
<211> LENGTH: 41
<212> TYPE: DNA
<213> ORGANISM: Artificial Sequence
<220> FEATURE:
<223> OTHER INFORMATION: FBC_Oligo17

<400> SEQUENCE: 139
caggtcggaa tgtgtgatcg tcggactgta gaactctgaa c                          41

<210> SEQ ID NO 140
<211> LENGTH: 41
<212> TYPE: DNA
<213> ORGANISM: Artificial Sequence
<220> FEATURE:
<223> OTHER INFORMATION: FBC_Oligo18

<400> SEQUENCE: 140
caggtcctat ggaaggatcg tcggactgta gaactctgaa c                          41

<210> SEQ ID NO 141
<211> LENGTH: 41
<212> TYPE: DNA
<213> ORGANISM: Artificial Sequence
<220> FEATURE:
<223> OTHER INFORMATION: FBC_Oligo19

<400> SEQUENCE: 141
caggtcaagt ccatggatcg tcggactgta gaactctgaa c                          41

<210> SEQ ID NO 142
<211> LENGTH: 41
<212> TYPE: DNA
<213> ORGANISM: Artificial Sequence
<220> FEATURE:
<223> OTHER INFORMATION: FBC_Oligo20

<400> SEQUENCE: 142
caggtcagta cttgggatcg tcggactgta gaactctgaa c                          41

<210> SEQ ID NO 143
<211> LENGTH: 41
<212> TYPE: DNA
<213> ORGANISM: Artificial Sequence
<220> FEATURE:
<223> OTHER INFORMATION: FBC_Oligo21

<400> SEQUENCE: 143
caggtcacag gactagatcg tcggactgta gaactctgaa c                          41

<210> SEQ ID NO 144
<211> LENGTH: 41
<212> TYPE: DNA
<213> ORGANISM: Artificial Sequence
<220> FEATURE:
<223> OTHER INFORMATION: FBC_Oligo22

-continued

```
<400> SEQUENCE: 144
caggtcacca ggtaagatcg tcggactgta gaactctgaa c                        41

<210> SEQ ID NO 145
<211> LENGTH: 41
<212> TYPE: DNA
<213> ORGANISM: Artificial Sequence
<220> FEATURE:
<223> OTHER INFORMATION: FBC_Oligo23

<400> SEQUENCE: 145
caggtcgcat gaaccgatcg tcggactgta gaactctgaa c                        41

<210> SEQ ID NO 146
<211> LENGTH: 41
<212> TYPE: DNA
<213> ORGANISM: Artificial Sequence
<220> FEATURE:
<223> OTHER INFORMATION: FBC_Oligo24

<400> SEQUENCE: 146
caggtcgttg gtgttgatcg tcggactgta gaactctgaa c                        41

<210> SEQ ID NO 147
<211> LENGTH: 41
<212> TYPE: DNA
<213> ORGANISM: Artificial Sequence
<220> FEATURE:
<223> OTHER INFORMATION: FBC_Oligo25

<400> SEQUENCE: 147
caggtccctt cagacgatcg tcggactgta gaactctgaa c                        41

<210> SEQ ID NO 148
<211> LENGTH: 41
<212> TYPE: DNA
<213> ORGANISM: Artificial Sequence
<220> FEATURE:
<223> OTHER INFORMATION: FBC_Oligo26

<400> SEQUENCE: 148
caggtccctc ttggtgatcg tcggactgta gaactctgaa c                        41

<210> SEQ ID NO 149
<211> LENGTH: 41
<212> TYPE: DNA
<213> ORGANISM: Artificial Sequence
<220> FEATURE:
<223> OTHER INFORMATION: FBC_Oligo27

<400> SEQUENCE: 149
caggtcggga aagttgatcg tcggactgta gaactctgaa c                        41

<210> SEQ ID NO 150
<211> LENGTH: 41
<212> TYPE: DNA
<213> ORGANISM: Artificial Sequence
<220> FEATURE:
<223> OTHER INFORMATION: FBC_Oligo28

<400> SEQUENCE: 150
caggtcagcc agagtgatcg tcggactgta gaactctgaa c                        41

<210> SEQ ID NO 151
```

-continued

```
<211> LENGTH: 41
<212> TYPE: DNA
<213> ORGANISM: Artificial Sequence
<220> FEATURE:
<223> OTHER INFORMATION: FBC_Oligo29

<400> SEQUENCE: 151
caggtctcgc atctggatcg tcggactgta gaactctgaa c                          41

<210> SEQ ID NO 152
<211> LENGTH: 41
<212> TYPE: DNA
<213> ORGANISM: Artificial Sequence
<220> FEATURE:
<223> OTHER INFORMATION: FBC_Oligo30

<400> SEQUENCE: 152
caggtcgata cggcagatcg tcggactgta gaactctgaa c                          41

<210> SEQ ID NO 153
<211> LENGTH: 41
<212> TYPE: DNA
<213> ORGANISM: Artificial Sequence
<220> FEATURE:
<223> OTHER INFORMATION: FBC_Oligo31

<400> SEQUENCE: 153
caggtctcgg ccaaagatcg tcggactgta gaactctgaa c                          41

<210> SEQ ID NO 154
<211> LENGTH: 41
<212> TYPE: DNA
<213> ORGANISM: Artificial Sequence
<220> FEATURE:
<223> OTHER INFORMATION: FBC_Oligo32

<400> SEQUENCE: 154
caggtcagat ttcgcgatcg tcggactgta gaactctgaa c                          41

<210> SEQ ID NO 155
<211> LENGTH: 41
<212> TYPE: DNA
<213> ORGANISM: Artificial Sequence
<220> FEATURE:
<223> OTHER INFORMATION: FBC_Oligo33

<400> SEQUENCE: 155
caggtcgacc ctcaagatcg tcggactgta gaactctgaa c                          41

<210> SEQ ID NO 156
<211> LENGTH: 41
<212> TYPE: DNA
<213> ORGANISM: Artificial Sequence
<220> FEATURE:
<223> OTHER INFORMATION: FBC_Oligo34

<400> SEQUENCE: 156
caggtcagtc cactcgatcg tcggactgta gaactctgaa c                          41

<210> SEQ ID NO 157
<211> LENGTH: 41
<212> TYPE: DNA
<213> ORGANISM: Artificial Sequence
<220> FEATURE:
<223> OTHER INFORMATION: FBC_Oligo35

<400> SEQUENCE: 157
```
caggtccaaa cgatcgatcg tcggactgta gaactctgaa c                              41

<210> SEQ ID NO 158
<211> LENGTH: 41
<212> TYPE: DNA
<213> ORGANISM: Artificial Sequence
<220> FEATURE:
<223> OTHER INFORMATION: FBC_Oligo36

<400> SEQUENCE: 158
caggtcgcct aataggatcg tcggactgta gaactctgaa c                              41

<210> SEQ ID NO 159
<211> LENGTH: 41
<212> TYPE: DNA
<213> ORGANISM: Artificial Sequence
<220> FEATURE:
<223> OTHER INFORMATION: FBC_Oligo37

<400> SEQUENCE: 159
caggtcggct acatcgatcg tcggactgta gaactctgaa c                              41

<210> SEQ ID NO 160
<211> LENGTH: 41
<212> TYPE: DNA
<213> ORGANISM: Artificial Sequence
<220> FEATURE:
<223> OTHER INFORMATION: FBC_Oligo38

<400> SEQUENCE: 160
caggtctatg agcaggatcg tcggactgta gaactctgaa c                              41

<210> SEQ ID NO 161
<211> LENGTH: 41
<212> TYPE: DNA
<213> ORGANISM: Artificial Sequence
<220> FEATURE:
<223> OTHER INFORMATION: FBC_Oligo39

<400> SEQUENCE: 161
caggtcggta gtaacgatcg tcggactgta gaactctgaa c                              41

<210> SEQ ID NO 162
<211> LENGTH: 41
<212> TYPE: DNA
<213> ORGANISM: Artificial Sequence
<220> FEATURE:
<223> OTHER INFORMATION: FBC_Oligo40

<400> SEQUENCE: 162
caggtccgcg tatatgatcg tcggactgta gaactctgaa c                              41

<210> SEQ ID NO 163
<211> LENGTH: 41
<212> TYPE: DNA
<213> ORGANISM: Artificial Sequence
<220> FEATURE:
<223> OTHER INFORMATION: FBC_Oligo41

<400> SEQUENCE: 163
caggtctact ggagcgatcg tcggactgta gaactctgaa c                              41

<210> SEQ ID NO 164
<211> LENGTH: 41
<212> TYPE: DNA

-continued

```
<213> ORGANISM: Artificial Sequence
<220> FEATURE:
<223> OTHER INFORMATION: FBC_Oligo42

<400> SEQUENCE: 164
caggtcaggg aatcagatcg tcggactgta gaactctgaa c                          41

<210> SEQ ID NO 165
<211> LENGTH: 41
<212> TYPE: DNA
<213> ORGANISM: Artificial Sequence
<220> FEATURE:
<223> OTHER INFORMATION: FBC_Oligo43

<400> SEQUENCE: 165
caggtcatcc gagatgatcg tcggactgta gaactctgaa c                          41

<210> SEQ ID NO 166
<211> LENGTH: 41
<212> TYPE: DNA
<213> ORGANISM: Artificial Sequence
<220> FEATURE:
<223> OTHER INFORMATION: FBC_Oligo44

<400> SEQUENCE: 166
caggtctccc aagcagatcg tcggactgta gaactctgaa c                          41

<210> SEQ ID NO 167
<211> LENGTH: 41
<212> TYPE: DNA
<213> ORGANISM: Artificial Sequence
<220> FEATURE:
<223> OTHER INFORMATION: FBC_Oligo45

<400> SEQUENCE: 167
caggtcgagc cgtttgatcg tcggactgta gaactctgaa c                          41

<210> SEQ ID NO 168
<211> LENGTH: 41
<212> TYPE: DNA
<213> ORGANISM: Artificial Sequence
<220> FEATURE:
<223> OTHER INFORMATION: FBC_Oligo46

<400> SEQUENCE: 168
caggtctgct cttacgatcg tcggactgta gaactctgaa c                          41

<210> SEQ ID NO 169
<211> LENGTH: 41
<212> TYPE: DNA
<213> ORGANISM: Artificial Sequence
<220> FEATURE:
<223> OTHER INFORMATION: FBC_Oligo47

<400> SEQUENCE: 169
caggtcacga ctaccgatcg tcggactgta gaactctgaa c                          41

<210> SEQ ID NO 170
<211> LENGTH: 41
<212> TYPE: DNA
<213> ORGANISM: Artificial Sequence
<220> FEATURE:
<223> OTHER INFORMATION: FBC_Oligo48

<400> SEQUENCE: 170
caggtccaag cagctgatcg tcggactgta gaactctgaa c                          41
```

<210> SEQ ID NO 171
<211> LENGTH: 40
<212> TYPE: DNA
<213> ORGANISM: Artificial Sequence
<220> FEATURE:
<223> OTHER INFORMATION: FBC_Oligo49

<400> SEQUENCE: 171
caggtcgtat tcgcgatcgt cggactgtag aactctgaac                                              40

<210> SEQ ID NO 172
<211> LENGTH: 40
<212> TYPE: DNA
<213> ORGANISM: Artificial Sequence
<220> FEATURE:
<223> OTHER INFORMATION: FBC_Oligo50

<400> SEQUENCE: 172
caggtcgctc tgaagatcgt cggactgtag aactctgaac                                              40

<210> SEQ ID NO 173
<211> LENGTH: 40
<212> TYPE: DNA
<213> ORGANISM: Artificial Sequence
<220> FEATURE:
<223> OTHER INFORMATION: FBC_Oligo51

<400> SEQUENCE: 173
caggtcacgt agtggatcgt cggactgtag aactctgaac                                              40

<210> SEQ ID NO 174
<211> LENGTH: 40
<212> TYPE: DNA
<213> ORGANISM: Artificial Sequence
<220> FEATURE:
<223> OTHER INFORMATION: FBC_Oligo52

<400> SEQUENCE: 174
caggtcattg ggtcgatcgt cggactgtag aactctgaac                                              40

<210> SEQ ID NO 175
<211> LENGTH: 40
<212> TYPE: DNA
<213> ORGANISM: Artificial Sequence
<220> FEATURE:
<223> OTHER INFORMATION: FBC_Oligo53

<400> SEQUENCE: 175
caggtcaaca gcacgatcgt cggactgtag aactctgaac                                              40

<210> SEQ ID NO 176
<211> LENGTH: 40
<212> TYPE: DNA
<213> ORGANISM: Artificial Sequence
<220> FEATURE:
<223> OTHER INFORMATION: FBC_Oligo54

<400> SEQUENCE: 176
caggtctcag agacgatcgt cggactgtag aactctgaac                                              40

<210> SEQ ID NO 177
<211> LENGTH: 40
<212> TYPE: DNA
<213> ORGANISM: Artificial Sequence
<220> FEATURE:

-continued

<223> OTHER INFORMATION: FBC_Oligo55

<400> SEQUENCE: 177
caggtcgtgt gctagatcgt cggactgtag aactctgaac                                40

<210> SEQ ID NO 178
<211> LENGTH: 40
<212> TYPE: DNA
<213> ORGANISM: Artificial Sequence
<220> FEATURE:
<223> OTHER INFORMATION: FBC_Oligo56

<400> SEQUENCE: 178
caggtcgcag ttgagatcgt cggactgtag aactctgaac                                40

<210> SEQ ID NO 179
<211> LENGTH: 40
<212> TYPE: DNA
<213> ORGANISM: Artificial Sequence
<220> FEATURE:
<223> OTHER INFORMATION: FBC_Oligo57

<400> SEQUENCE: 179
caggtcttaa cggggatcgt cggactgtag aactctgaac                                40

<210> SEQ ID NO 180
<211> LENGTH: 40
<212> TYPE: DNA
<213> ORGANISM: Artificial Sequence
<220> FEATURE:
<223> OTHER INFORMATION: FBC_Oligo58

<400> SEQUENCE: 180
caggtcgctc gattgatcgt cggactgtag aactctgaac                                40

<210> SEQ ID NO 181
<211> LENGTH: 40
<212> TYPE: DNA
<213> ORGANISM: Artificial Sequence
<220> FEATURE:
<223> OTHER INFORMATION: FBC_Oligo59

<400> SEQUENCE: 181
caggtcacac ctgtgatcgt cggactgtag aactctgaac                                40

<210> SEQ ID NO 182
<211> LENGTH: 40
<212> TYPE: DNA
<213> ORGANISM: Artificial Sequence
<220> FEATURE:
<223> OTHER INFORMATION: FBC_Oligo60

<400> SEQUENCE: 182
caggtcagac ggttgatcgt cggactgtag aactctgaac                                40

<210> SEQ ID NO 183
<211> LENGTH: 40
<212> TYPE: DNA
<213> ORGANISM: Artificial Sequence
<220> FEATURE:
<223> OTHER INFORMATION: FBC_Oligo61

<400> SEQUENCE: 183
caggtcgcaa accagatcgt cggactgtag aactctgaac                                40

-continued

```
<210> SEQ ID NO 184
<211> LENGTH: 40
<212> TYPE: DNA
<213> ORGANISM: Artificial Sequence
<220> FEATURE:
<223> OTHER INFORMATION: FBC_Oligo62

<400> SEQUENCE: 184
caggtcgagt atgggatcgt cggactgtag aactctgaac                              40

<210> SEQ ID NO 185
<211> LENGTH: 40
<212> TYPE: DNA
<213> ORGANISM: Artificial Sequence
<220> FEATURE:
<223> OTHER INFORMATION: FBC_Oligo63

<400> SEQUENCE: 185
caggtcggtc tttcgatcgt cggactgtag aactctgaac                              40

<210> SEQ ID NO 186
<211> LENGTH: 40
<212> TYPE: DNA
<213> ORGANISM: Artificial Sequence
<220> FEATURE:
<223> OTHER INFORMATION: FBC_Oligo64

<400> SEQUENCE: 186
caggtccatc tgctgatcgt cggactgtag aactctgaac                              40

<210> SEQ ID NO 187
<211> LENGTH: 40
<212> TYPE: DNA
<213> ORGANISM: Artificial Sequence
<220> FEATURE:
<223> OTHER INFORMATION: FBC_Oligo65

<400> SEQUENCE: 187
caggtcttcg caaggatcgt cggactgtag aactctgaac                              40

<210> SEQ ID NO 188
<211> LENGTH: 40
<212> TYPE: DNA
<213> ORGANISM: Artificial Sequence
<220> FEATURE:
<223> OTHER INFORMATION: FBC_Oligo66

<400> SEQUENCE: 188
caggtcttgt gacggatcgt cggactgtag aactctgaac                              40

<210> SEQ ID NO 189
<211> LENGTH: 40
<212> TYPE: DNA
<213> ORGANISM: Artificial Sequence
<220> FEATURE:
<223> OTHER INFORMATION: FBC_Oligo67

<400> SEQUENCE: 189
caggtctgca tgacgatcgt cggactgtag aactctgaac                              40

<210> SEQ ID NO 190
<211> LENGTH: 40
<212> TYPE: DNA
<213> ORGANISM: Artificial Sequence
<220> FEATURE:
<223> OTHER INFORMATION: FBC_Oligo68
```

-continued

```
<400> SEQUENCE: 190
caggtccaac gtgagatcgt cggactgtag aactctgaac                            40

<210> SEQ ID NO 191
<211> LENGTH: 40
<212> TYPE: DNA
<213> ORGANISM: Artificial Sequence
<220> FEATURE:
<223> OTHER INFORMATION: FBC_Oligo69

<400> SEQUENCE: 191
caggtctagg cttcgatcgt cggactgtag aactctgaac                            40

<210> SEQ ID NO 192
<211> LENGTH: 40
<212> TYPE: DNA
<213> ORGANISM: Artificial Sequence
<220> FEATURE:
<223> OTHER INFORMATION: FBC_Oligo70

<400> SEQUENCE: 192
caggtctggt aggagatcgt cggactgtag aactctgaac                            40

<210> SEQ ID NO 193
<211> LENGTH: 40
<212> TYPE: DNA
<213> ORGANISM: Artificial Sequence
<220> FEATURE:
<223> OTHER INFORMATION: FBC_Oligo71

<400> SEQUENCE: 193
caggtctgca gcttgatcgt cggactgtag aactctgaac                            40

<210> SEQ ID NO 194
<211> LENGTH: 40
<212> TYPE: DNA
<213> ORGANISM: Artificial Sequence
<220> FEATURE:
<223> OTHER INFORMATION: FBC_Oligo72

<400> SEQUENCE: 194
caggtcctgt acctgatcgt cggactgtag aactctgaac                            40

<210> SEQ ID NO 195
<211> LENGTH: 40
<212> TYPE: DNA
<213> ORGANISM: Artificial Sequence
<220> FEATURE:
<223> OTHER INFORMATION: FBC_Oligo73

<400> SEQUENCE: 195
caggtccgca atgagatcgt cggactgtag aactctgaac                            40

<210> SEQ ID NO 196
<211> LENGTH: 40
<212> TYPE: DNA
<213> ORGANISM: Artificial Sequence
<220> FEATURE:
<223> OTHER INFORMATION: FBC_Oligo74

<400> SEQUENCE: 196
caggtcgatc caaggatcgt cggactgtag aactctgaac                            40

<210> SEQ ID NO 197
<211> LENGTH: 40
```

```
<212> TYPE: DNA
<213> ORGANISM: Artificial Sequence
<220> FEATURE:
<223> OTHER INFORMATION: FBC_Oligo75

<400> SEQUENCE: 197
caggtccact tacggatcgt cggactgtag aactctgaac                                    40

<210> SEQ ID NO 198
<211> LENGTH: 40
<212> TYPE: DNA
<213> ORGANISM: Artificial Sequence
<220> FEATURE:
<223> OTHER INFORMATION: FBC_Oligo76

<400> SEQUENCE: 198
caggtcaact aggcgatcgt cggactgtag aactctgaac                                    40

<210> SEQ ID NO 199
<211> LENGTH: 40
<212> TYPE: DNA
<213> ORGANISM: Artificial Sequence
<220> FEATURE:
<223> OTHER INFORMATION: FBC_Oligo77

<400> SEQUENCE: 199
caggtcacta gcgtgatcgt cggactgtag aactctgaac                                    40

<210> SEQ ID NO 200
<211> LENGTH: 40
<212> TYPE: DNA
<213> ORGANISM: Artificial Sequence
<220> FEATURE:
<223> OTHER INFORMATION: FBC_Oligo78

<400> SEQUENCE: 200
caggtccgtt cgttgatcgt cggactgtag aactctgaac                                    40

<210> SEQ ID NO 201
<211> LENGTH: 40
<212> TYPE: DNA
<213> ORGANISM: Artificial Sequence
<220> FEATURE:
<223> OTHER INFORMATION: FBC_Oligo79

<400> SEQUENCE: 201
caggtcagtc acgagatcgt cggactgtag aactctgaac                                    40

<210> SEQ ID NO 202
<211> LENGTH: 40
<212> TYPE: DNA
<213> ORGANISM: Artificial Sequence
<220> FEATURE:
<223> OTHER INFORMATION: FBC_Oligo80

<400> SEQUENCE: 202
caggtccctg taacgatcgt cggactgtag aactctgaac                                    40

<210> SEQ ID NO 203
<211> LENGTH: 40
<212> TYPE: DNA
<213> ORGANISM: Artificial Sequence
<220> FEATURE:
<223> OTHER INFORMATION: FBC_Oligo81

<400> SEQUENCE: 203
```

-continued caggtcgtcc tcttgatcgt cggactgtag aactctgaac                                                    40

<210> SEQ ID NO 204
<211> LENGTH: 40
<212> TYPE: DNA
<213> ORGANISM: Artificial Sequence
<220> FEATURE:
<223> OTHER INFORMATION: FBC_Oligo82

<400> SEQUENCE: 204
caggtccagc gaatgatcgt cggactgtag aactctgaac                                                    40

<210> SEQ ID NO 205
<211> LENGTH: 40
<212> TYPE: DNA
<213> ORGANISM: Artificial Sequence
<220> FEATURE:
<223> OTHER INFORMATION: FBC_Oligo83

<400> SEQUENCE: 205
caggtcatgg ttgggatcgt cggactgtag aactctgaac                                                    40

<210> SEQ ID NO 206
<211> LENGTH: 40
<212> TYPE: DNA
<213> ORGANISM: Artificial Sequence
<220> FEATURE:
<223> OTHER INFORMATION: FBC_Oligo84

<400> SEQUENCE: 206
caggtcgagg ttctgatcgt cggactgtag aactctgaac                                                    40

<210> SEQ ID NO 207
<211> LENGTH: 40
<212> TYPE: DNA
<213> ORGANISM: Artificial Sequence
<220> FEATURE:
<223> OTHER INFORMATION: FBC_Oligo85

<400> SEQUENCE: 207
caggtctacc tcgagatcgt cggactgtag aactctgaac                                                    40

<210> SEQ ID NO 208
<211> LENGTH: 40
<212> TYPE: DNA
<213> ORGANISM: Artificial Sequence
<220> FEATURE:
<223> OTHER INFORMATION: FBC_Oligo86

<400> SEQUENCE: 208
caggtcttct gtgcgatcgt cggactgtag aactctgaac                                                    40

<210> SEQ ID NO 209
<211> LENGTH: 40
<212> TYPE: DNA
<213> ORGANISM: Artificial Sequence
<220> FEATURE:
<223> OTHER INFORMATION: FBC_Oligo87

<400> SEQUENCE: 209
caggtcgaca actggatcgt cggactgtag aactctgaac                                                    40

<210> SEQ ID NO 210
<211> LENGTH: 40
<212> TYPE: DNA
<213> ORGANISM: Artificial Sequence

```
<220> FEATURE:
<223> OTHER INFORMATION: FBC_Oligo88

<400> SEQUENCE: 210
caggtccgac aacagatcgt cggactgtag aactctgaac                                        40

<210> SEQ ID NO 211
<211> LENGTH: 40
<212> TYPE: DNA
<213> ORGANISM: Artificial Sequence
<220> FEATURE:
<223> OTHER INFORMATION: FBC_Oligo89

<400> SEQUENCE: 211
caggtctcga taccgatcgt cggactgtag aactctgaac                                        40

<210> SEQ ID NO 212
<211> LENGTH: 40
<212> TYPE: DNA
<213> ORGANISM: Artificial Sequence
<220> FEATURE:
<223> OTHER INFORMATION: FBC_Oligo90

<400> SEQUENCE: 212
caggtcccat actcgatcgt cggactgtag aactctgaac                                        40

<210> SEQ ID NO 213
<211> LENGTH: 40
<212> TYPE: DNA
<213> ORGANISM: Artificial Sequence
<220> FEATURE:
<223> OTHER INFORMATION: FBC_Oligo91

<400> SEQUENCE: 213
caggtcattc gcaggatcgt cggactgtag aactctgaac                                        40

<210> SEQ ID NO 214
<211> LENGTH: 40
<212> TYPE: DNA
<213> ORGANISM: Artificial Sequence
<220> FEATURE:
<223> OTHER INFORMATION: FBC_Oligo92

<400> SEQUENCE: 214
caggtcacca tagggatcgt cggactgtag aactctgaac                                        40

<210> SEQ ID NO 215
<211> LENGTH: 40
<212> TYPE: DNA
<213> ORGANISM: Artificial Sequence
<220> FEATURE:
<223> OTHER INFORMATION: FBC_Oligo93

<400> SEQUENCE: 215
caggtccgat caaggatcgt cggactgtag aactctgaac                                        40

<210> SEQ ID NO 216
<211> LENGTH: 40
<212> TYPE: DNA
<213> ORGANISM: Artificial Sequence
<220> FEATURE:
<223> OTHER INFORMATION: FBC_Oligo94

<400> SEQUENCE: 216
caggtcacct tgctgatcgt cggactgtag aactctgaac                                        40
```

<210> SEQ ID NO 217
<211> LENGTH: 40
<212> TYPE: DNA
<213> ORGANISM: Artificial Sequence
<220> FEATURE:
<223> OTHER INFORMATION: FBC_Oligo95

<400> SEQUENCE: 217
caggtcgact cagtgatcgt cggactgtag aactctgaac                              40

<210> SEQ ID NO 218
<211> LENGTH: 40
<212> TYPE: DNA
<213> ORGANISM: Artificial Sequence
<220> FEATURE:
<223> OTHER INFORMATION: FBC_Oligo96

<400> SEQUENCE: 218
caggtcgtca atccgatcgt cggactgtag aactctgaac                              40

<210> SEQ ID NO 219
<211> LENGTH: 68
<212> TYPE: DNA
<213> ORGANISM: Artificial Sequence
<220> FEATURE:
<223> OTHER INFORMATION: SBC_Oligo1

<400> SEQUENCE: 219
aaaaaaaaaa aaaaaaaaaa aaaaggtga tacaggtcaa aaaaaaagat cgtcggactg        60
tagaactc                                                                68

<210> SEQ ID NO 220
<211> LENGTH: 68
<212> TYPE: DNA
<213> ORGANISM: Artificial Sequence
<220> FEATURE:
<223> OTHER INFORMATION: SBC_Oligo2

<400> SEQUENCE: 220
aaaaaaaaaa aaaaaaaaaa aaaaatgaat gccaggtcaa aaaaaaagat cgtcggactg        60
tagaactc                                                                68

<210> SEQ ID NO 221
<211> LENGTH: 68
<212> TYPE: DNA
<213> ORGANISM: Artificial Sequence
<220> FEATURE:
<223> OTHER INFORMATION: SBC_Oligo3

<400> SEQUENCE: 221
aaaaaaaaaa aaaaaaaaaa aaaaatgcca acaggtcaa aaaaaaagat cgtcggactg         60
tagaactc                                                                68

<210> SEQ ID NO 222
<211> LENGTH: 68
<212> TYPE: DNA
<213> ORGANISM: Artificial Sequence
<220> FEATURE:
<223> OTHER INFORMATION: SBC_Oligo4

<400> SEQUENCE: 222
aaaaaaaaaa aaaaaaaaaa aaaaacaga agcaggtcaa aaaaaaagat cgtcggactg         60
tagaactc                                                                68

```
<210> SEQ ID NO 223
<211> LENGTH: 68
<212> TYPE: DNA
<213> ORGANISM: Artificial Sequence
<220> FEATURE:
<223> OTHER INFORMATION: SBC_Oligo5

<400> SEQUENCE: 223
aaaaaaaaaa aaaaaaaaaa aaaaacactg gacaggtcaa aaaaaaagat cgtcggactg      60
tagaactc                                                              68

<210> SEQ ID NO 224
<211> LENGTH: 68
<212> TYPE: DNA
<213> ORGANISM: Artificial Sequence
<220> FEATURE:
<223> OTHER INFORMATION: SBC_Oligo6

<400> SEQUENCE: 224
aaaaaaaaaa aaaaaaaaaa aaaaacgatg atcaggtcaa aaaaaaagat cgtcggactg      60
tagaactc                                                              68

<210> SEQ ID NO 225
<211> LENGTH: 68
<212> TYPE: DNA
<213> ORGANISM: Artificial Sequence
<220> FEATURE:
<223> OTHER INFORMATION: SBC_Oligo7

<400> SEQUENCE: 225
aaaaaaaaaa aaaaaaaaaa aaaaagtgtc cacaggtcaa aaaaaaagat cgtcggactg      60
tagaactc                                                              68

<210> SEQ ID NO 226
<211> LENGTH: 68
<212> TYPE: DNA
<213> ORGANISM: Artificial Sequence
<220> FEATURE:
<223> OTHER INFORMATION: SBC_Oligo8

<400> SEQUENCE: 226
aaaaaaaaaa aaaaaaaaaa aaaaatcctc ttcaggtcaa aaaaaaagat cgtcggactg      60
tagaactc                                                              68

<210> SEQ ID NO 227
<211> LENGTH: 68
<212> TYPE: DNA
<213> ORGANISM: Artificial Sequence
<220> FEATURE:
<223> OTHER INFORMATION: SBC_Oligo9

<400> SEQUENCE: 227
aaaaaaaaaa aaaaaaaaaa aaaaagtgca gtcaggtcaa aaaaaaagat cgtcggactg      60
tagaactc                                                              68

<210> SEQ ID NO 228
<211> LENGTH: 68
<212> TYPE: DNA
<213> ORGANISM: Artificial Sequence
<220> FEATURE:
<223> OTHER INFORMATION: SBC_Oligo10
```

-continued

<400> SEQUENCE: 228
aaaaaaaaaa aaaaaaaaaa aaaaaaggta gacaggtcaa aaaaaaagat cgtcggactg          60
tagaactc                                                                   68

RNA PRINTING AND SEQUENCING DEVICES, METHODS, AND SYSTEMS

CROSS REFERENCE TO RELATED APPLICATIONS

This application is a continuation of U.S. patent application Ser. No. 15/576,925, filed Nov. 27, 2017 (now abandoned), which is a 371 of International Patent Application No. PCT/US2016/034270, filed May 26, 2016, which claims priority to U.S. Application Ser. No. 62/166,565, filed May 26, 2015, each of which is herein incorporated by reference in its entirety.

STATEMENT OF GOVERNMENTAL INTEREST

This invention was made with government support under EB016071, EB016980, CA202827, and CA019333 awarded by the National Institutes of Health. The government has certain rights in the invention.

BACKGROUND

Single cell analysis is important for understanding how cells respond to drugs and other perturbations because phenotypic responses are asynchronous and cells are often both genetically and epigenetically heterogeneous. In the absence of artificial or external perturbations, the natural processes of cellular differentiation during development and malignant transformation in cancer also occur asynchronously and give rise to phenotypic heterogeneity. While single cell RNA-Seq is emerging as a high-dimensional and increasingly scalable tool for assessing phenotypic heterogeneity, many aspects of cellular phenotype cannot be inferred from the transcriptome alone. However, high-content imaging by microscopy could greatly expand the space of observables in a single cell analysis, particularly if it can be integrated with single cell RNA-Seq. High-content imaging assays using optical microscopy provide access to numerous phenotypic observables for cellular metabolism, protein localization, protein synthesis, cell cycle states, and cell signaling all with single cell resolution. However, existing tools for merging single cell imaging and sequencing are expensive, low-throughput, and incompatible with short-term cell culture and stimulation. The instant disclosure addresses this issue by combining a highly scalable microfluidic platform for single cell RNA-Seq and imaging with associated methodologies that allow for the association of sequence barcodes for inexpensive pooled library preparation with optical barcodes in devices described herein.

SUMMARY

The disclosure allows for devices, systems, and methods relating to genome-wide profiling of RNA from hundreds to thousands of individual cells in parallel for only a few cents per cell. The devices, systems, and methods described herein address the scalability problem of parallel preparation of low-input single cell libraries for RNA sequencing. Devices, systems, and methods described herein allow for parallel RNA profiling of individual cells in a device that is compatible with short term cell culture, drug stimulation experiments, and high-content fluorescence imaging. In an aspect, this is because the cells are physically segregated into microwells but still in sufficiently close proximity to communicate via diffusible factors.

In an aspect, the disclosure provides for a device or system comprising

- (a) one or more mRNA capture beads;
- (b) one or more cell-identifying optical barcodes;
- (c) a plurality of chambers, microchambers, or microwells comprising one or more mRNA capture beads and/or one or more cell-identifying optical barcodes; and
- (d) wherein the plurality of chambers, microchambers, or microwells comprising one or more mRNA capture beads and/or one or more cell-identifying optical barcodes are configured for reversible sealing.

In an aspect, the disclosure provides for a method of drug discovery, drug profiling, and/or drug testing comprising

- (a) combining one or more mRNA capture beads with one or more cell-identifying optical barcodes;
- (b) adding one or more mRNA capture beads with one or more cell-identifying optical barcodes to a plurality of chambers, microchambers, or microwells;
- (c) wherein the plurality of chambers, microchambers, or microwells including one or more mRNA capture beads and one or more cell-identifying barcodes are configured for reversible sealing; and
- (d) adding one or more drugs to the plurality of chambers, microchambers, or microwells configured for reversible sealing; and
- (e) adding one or more cells to the plurality of chambers, microchambers, or microwells that are configured for reversible sealing.

In an aspect, the one or more optical barcodes include one or more optical barcode sequences. In another aspect, the one or more optical barcodes include one or more fluorescent dyes including different colors and/or intensities.

The disclosure further provides for method of drug discovery, drug profiling, and/or drug testing described herein comprising (f) adding a buffer to the plurality of chambers, microchambers, or microwells configured for reversible sealing. In an aspect, the buffer includes a lysis buffer.

The disclosure further provides for a method of drug discovery, drug profiling, and/or drug testing comprising analyzing said cell-identifying optical barcode sequences by fluorescence.

In another aspect, the device or system of described herein comprise a plurality of chambers, microchambers, or microwells attached to a polysiloxane substrate. In yet another aspect, said polysiloxane substrate comprises polydimethylsiloxane.

In another aspect, the device or system described herein comprise cell-identifying optical barcode sequences are adapted for florescence detection.

In yet another aspect, the device, system, or methods comprise cells and said cells are not arranged in a droplet configuration.

In another aspect, the disclosure provides for a method for single cell RNA capture and sequencing, wherein said method comprises

- (a) introducing at least one cell into a microwell, wherein the microwell is attached to a first substrate that faces a second substrate and wherein oligo primers are attached to the surface of said second substrate;
- (b) hybridizing mRNA molecules to the surface of said second substrate;
- (c) adding at least one buffer to the microwell; and
- (d) contacting said first substrate with said second substrate, thereby creating a seal between said first substrate and said second substrate.

In yet another aspect, the disclosure provides for a device for single cell RNA capture and sequencing, wherein said device comprises a plurality of microwells; wherein said plurality of microwells are attached to a first polysiloxane substrate; a second substrate comprising glass that faces said first substrate, wherein oligo primers are grafted onto to the glass surface of said second substrate.

The disclosure further provides for a microwell comprising a composition comprising one or more mRNA capture beads; one or more cell-identifying optical barcode sequences; one or more cells, one of more buffers.

BRIEF DESCRIPTION OF THE FIGURES

The patent or application file contains at least one drawing executed in color. Copies of this patent or patent application publication with color drawings(s) will be provided by the Office upon request and payment of the necessary fee.

(FIG. 2A) For mRNA capture on polymer beads, the microwell array is fabricated in a thin PDMS layer on top of a glass slide or coverslip with a microfluidic flow channel above. Cells are first deposited in the microwell array by gravity followed by beads (while circles) cov-2Balently functionalized with oligo(dT) primers (orange circular outlines). A lysis buffer is introduced followed by rapid displacement of fluid in the channel with oil, which conformally seals the array. Single cell lysates (green) become trapped in individual microwells and mRNA hybridizes to the oligo(dT) on the beads (red circular outlines).

FIGS. 3A and 3B provide for combinatorial scheme for synthesis of barcoded capture beads. As illustrated in FIG. 3A, beads are first attached to a set of barcoded oligonucleotides in a multi-well plate, pooled into a single tube, and then re-distributed into a second multi-well plate for combinatorial addition of a second barcode sequence and capture site (oligo(dT)). FIG. 3B provides for detailed molecular biology for solid-phase, combinatorial barcode synthesis. A first barcode sequence is copied onto a dual-biotinylated oligonucleotide containing the T7 promoter sequence and a partial Illumina adapter using DNA polymerase. The resulting double-stranded DNA is conjugated to streptavidin-coated beads, and the non-biotinylated strand is removed.

After pooling and expanding the beads, a second reaction is used to add a second barcode sequence and oligo(dT) by priming off of a universal anchor sequence that follows the first barcode.

Figure 4A:
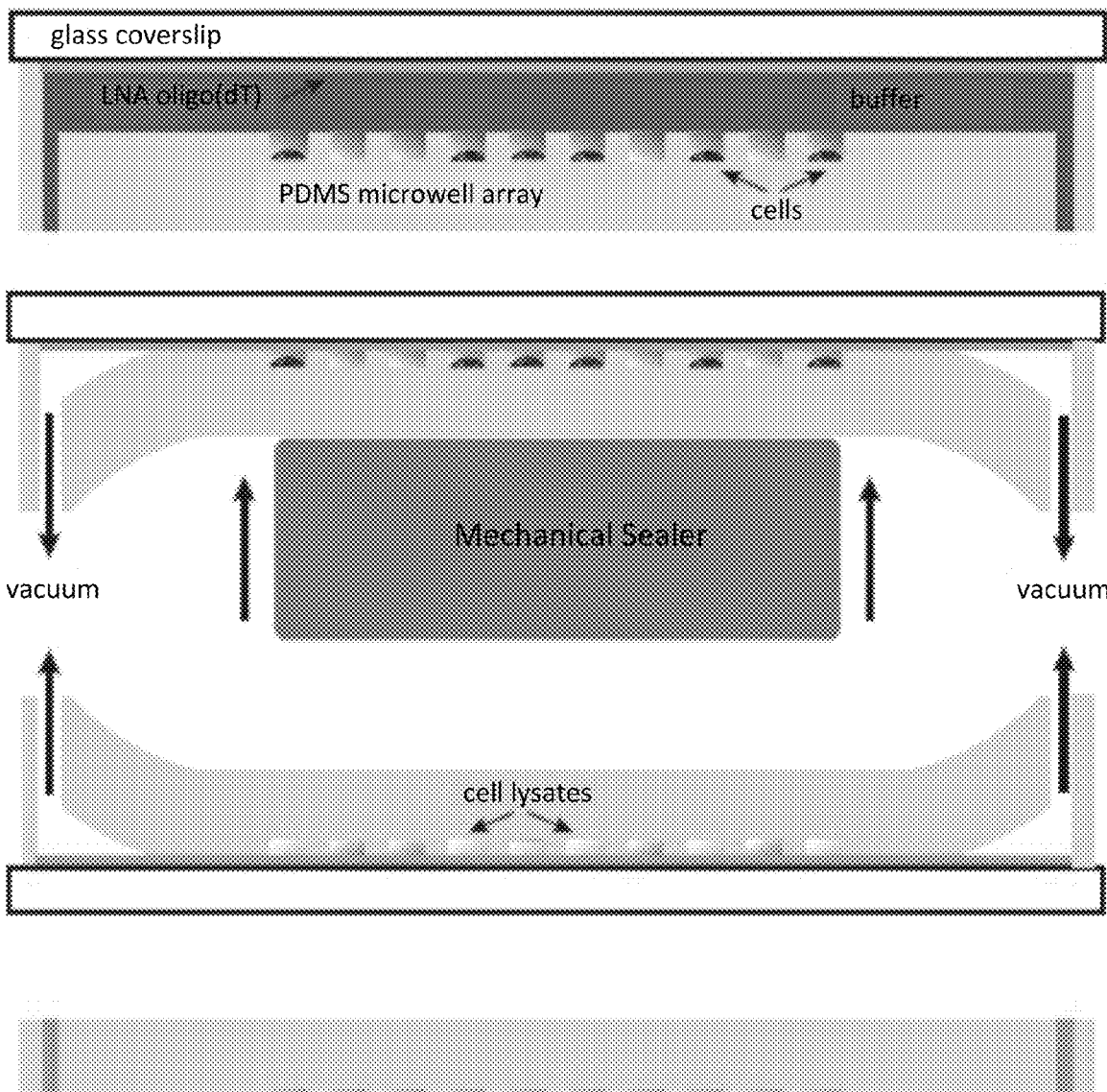
Figure 4B:
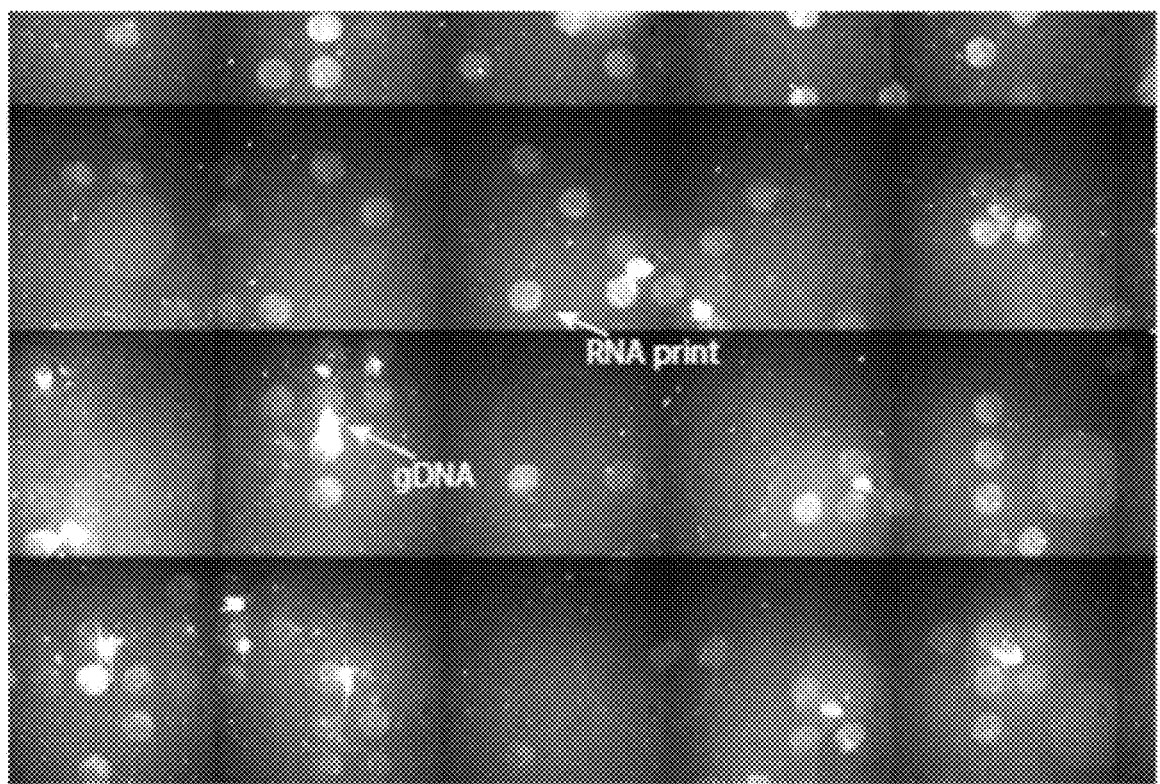
Figure 4C:
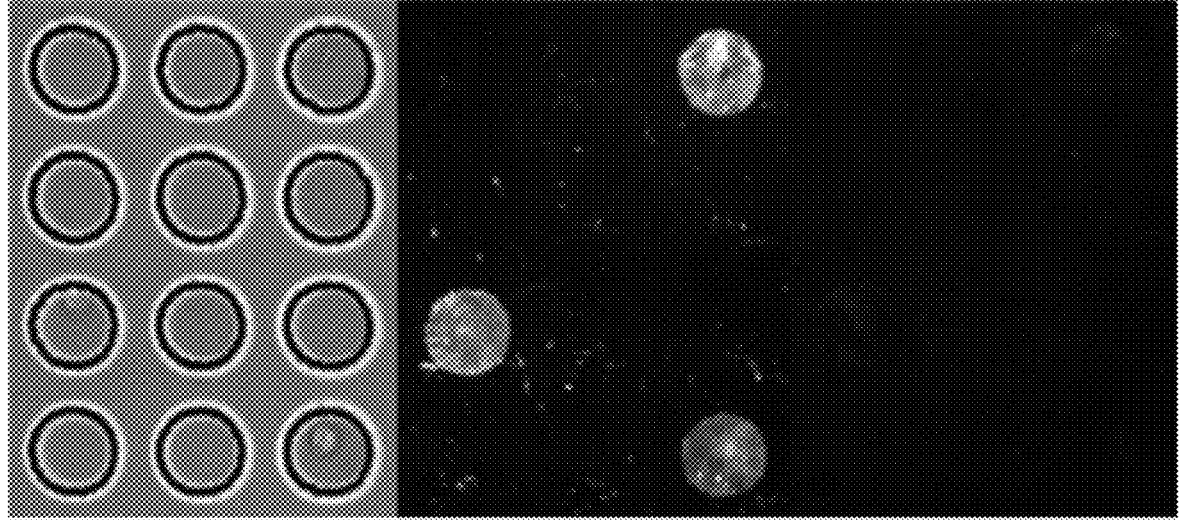

FIGS. 4A-4C provide for a schematic and fluorescence imaging data for single cell RNA printing. As shown in FIG. 4A, cells are first deposited in the microwell array by gravity. The glass surface opposite the microwell array is covalently functionalized with oligo(dT) primers for mRNA capture (orange line). The device is then rapidly and conformally sealed against a glass surface in the presence of lysis buffer, flipped over, and held in a sealed position using negative pressure. Single cell lysates (green) become trapped in the sealed microwells, and mRNA hybridizes to the oligo(dT) primers on the glass surface, resulting in single cell mRNA "prints" (red lines). As shown by FIG. 4B an array of single cell mRNA prints on a glass coverslip generated using the device in FIG. 4A and imaged after on-chip reverse transcription. The double-stranded RNA/DNA hybrids are stained with SYTOX Orange, an intercalator dye and imaged on the glass surface. >96% of the prints result from individual cells. Note that the bright spots in the image that are not registered with the array originate from genomic DNA aggregates that were not fully removed by DNase digestion. FIG. 4C shows close-up images of single cell RNA printing. The left-most panel is a bright field image of three cells in individual microwells of the array, the middle panel is a fluorescence image of the corresponding RNA prints on the glass surface after reverse transcription and staining with SYTOX Orange, and the right-most panel is a fluorescence image of the glass surface after RNase digestion, demonstrating that the fluorescent prints originate from captured RNA.

Figure 5A:
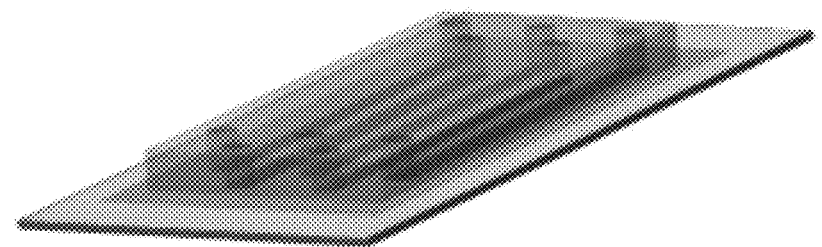
Figure 5B:
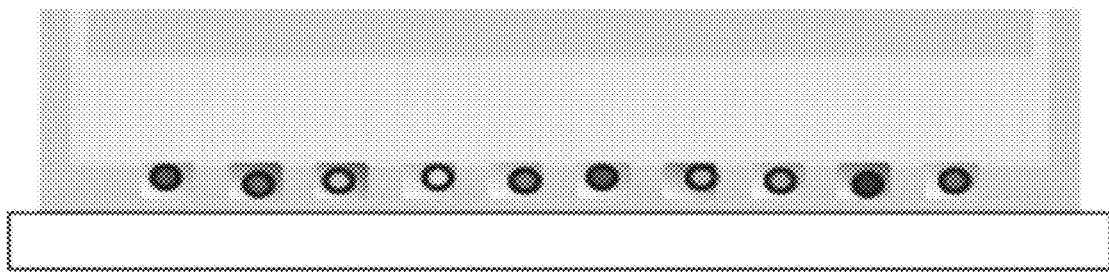
Figure 5B:
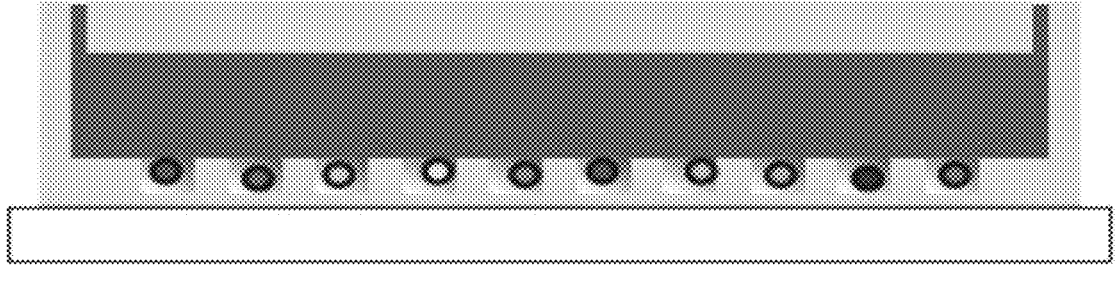
Figure 5B:
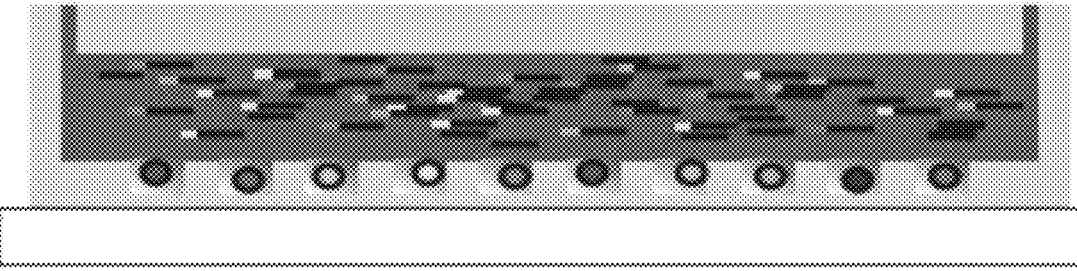
Figure 5C:
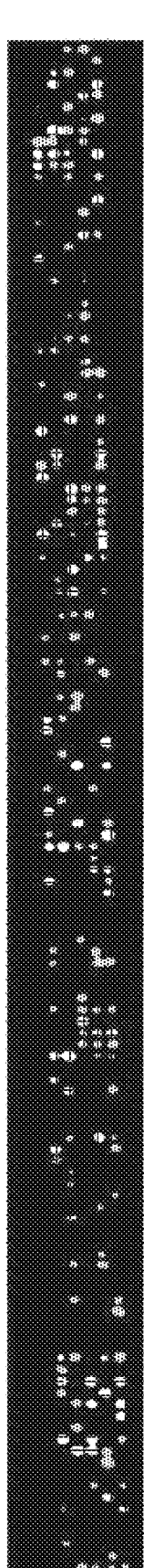

FIGS. 5A-5C provide for an example flow cell device for single cell RNA-Seq. (A) Graphical representation of our five-lane microwell array flow cell device for single cell RNA-Seq. FIG. 5B shows a schematic of on-chip steps for single cell RNA-Seq. After depositing cells, barcoded capture beads (barcode sequences represented as different colors), and sealing as in FIG. 2A, single cell lysates (green) are trapped in individual microwells and mRNA hybridizes to the barcoded capture beads. The device is unsealed and rapidly washed by flow before on-chip, solid-phase reverse transcription and second-strand synthesis followed by elution and pre-amplification of the pooled library by in vitro transcription. FIG. 5C shows a montage of fluorescence images from part of one lane of the device in FIG. 5A showing beads (red) and cells (blue) loaded in the array. Note that this image was acquired following cell lysis while the device is sealed, and so the blue live stain fills the entire volume of the corresponding microwell and is confined to the microwell by sealing.

Figure 6A:
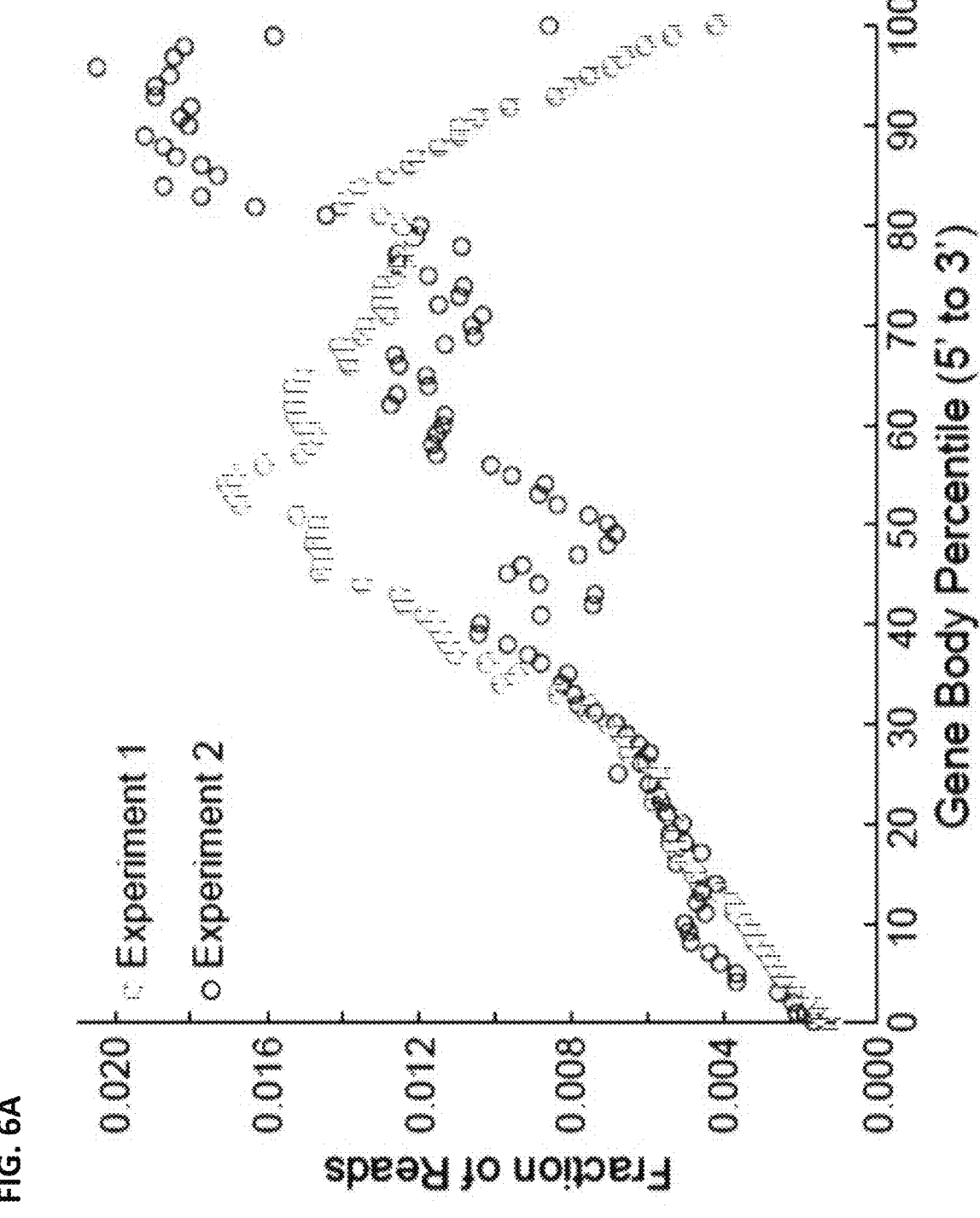
Figure 6B:
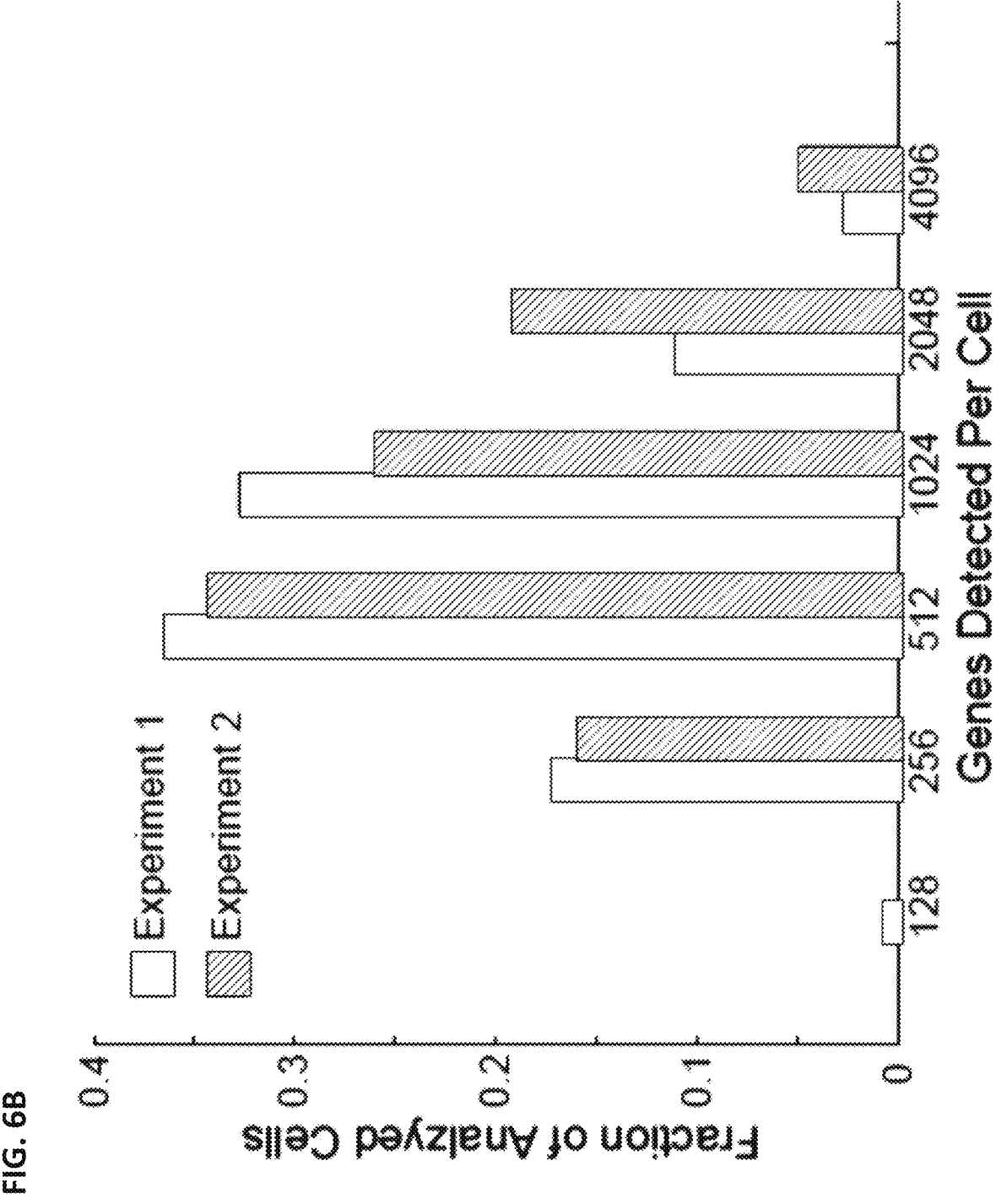

FIGS. 6A and 6B show an analysis of single cell RNA-Seq data. FIG. 6A shows a gene body distribution for uniquely mapped reads showing that we are primarily sequencing the 3'-end of transcripts, as expected. FIG. 6B shows a histogram of the number of genes detected per cell for the 396 single cell profiles used in all subsequent analysis of Experiment 1 and 247 single cell profiles used in all subsequent analysis of Experiment 2.

Figure 7A:
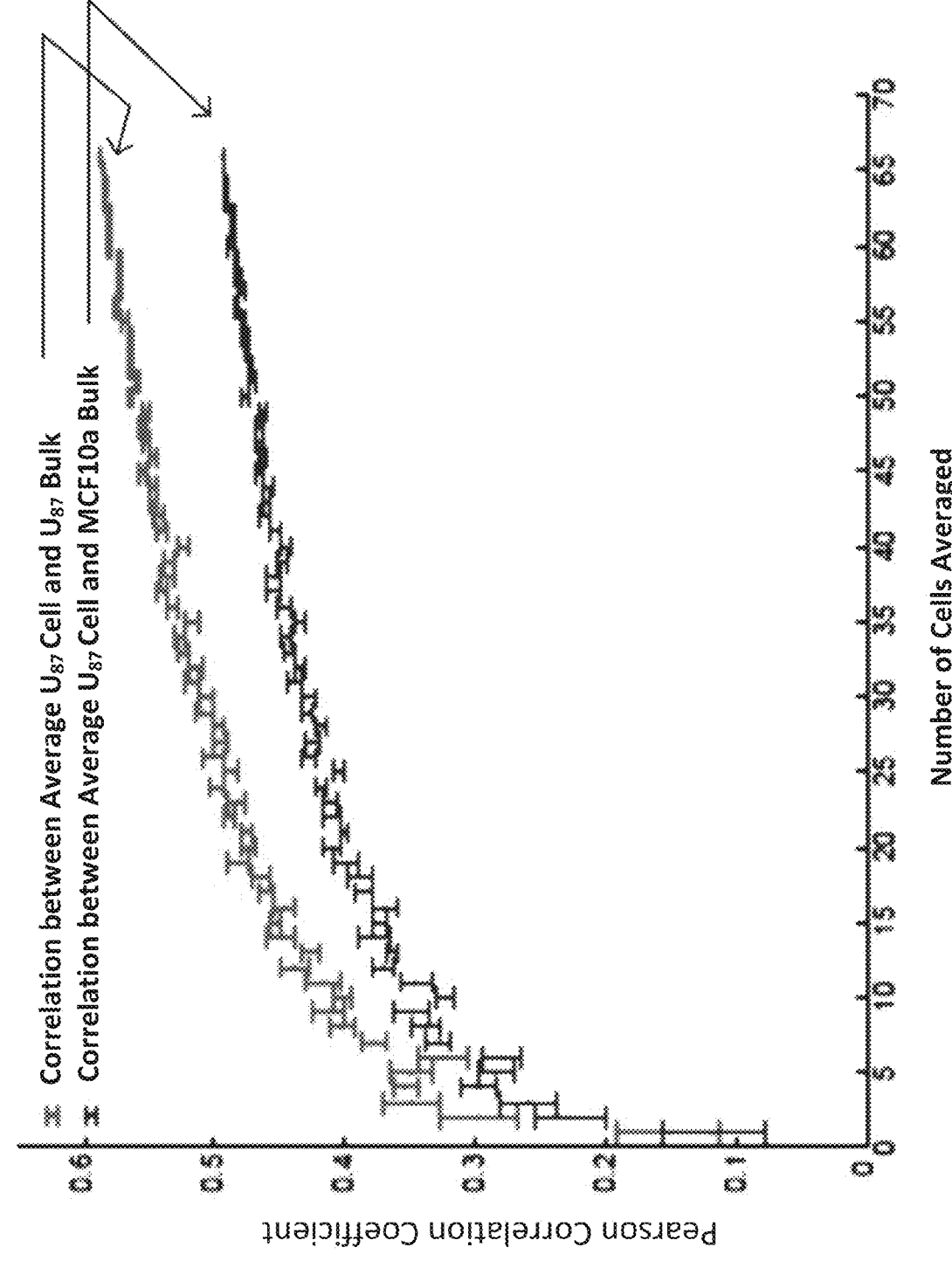
Figure 7B:
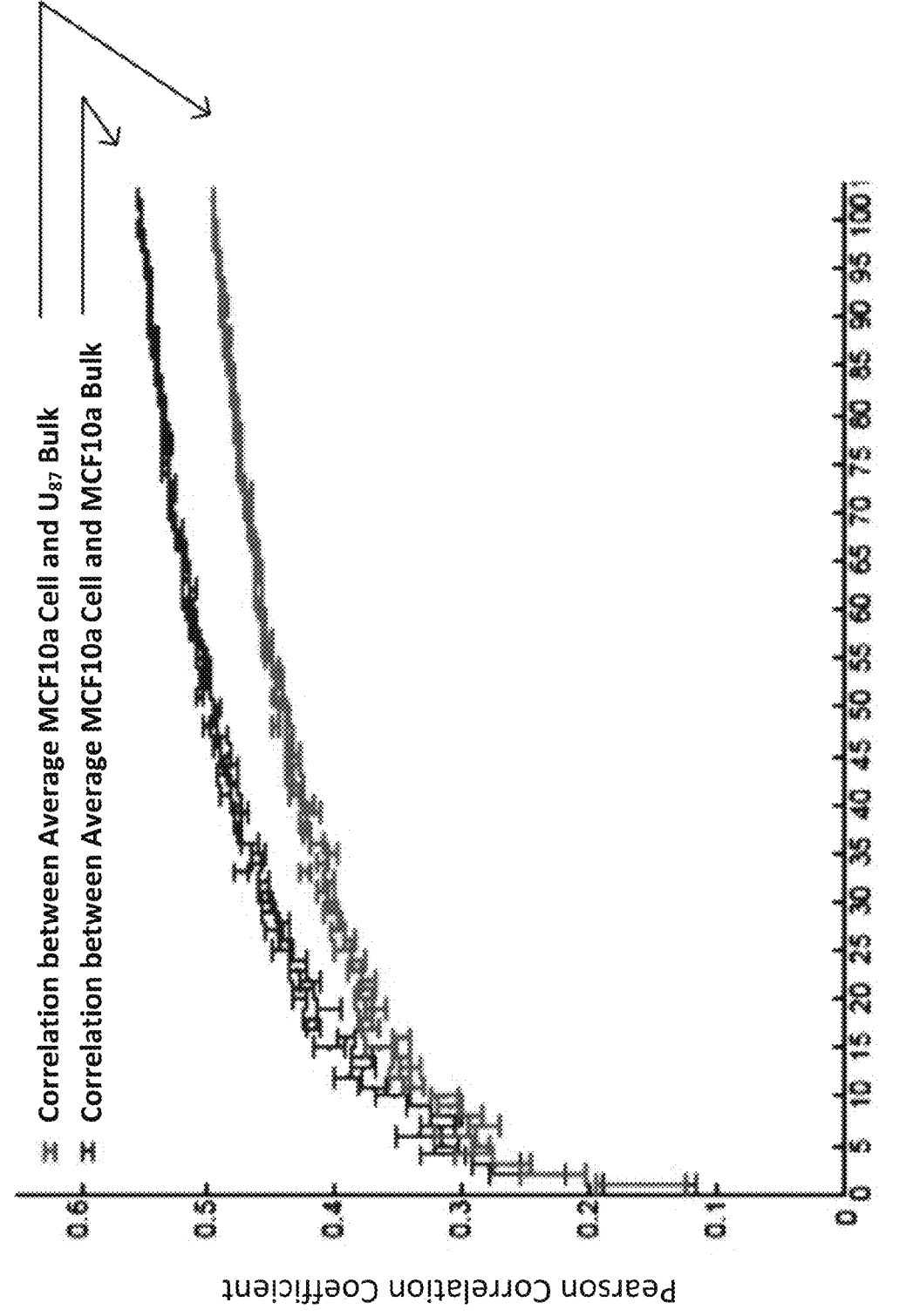
Figure 7C:
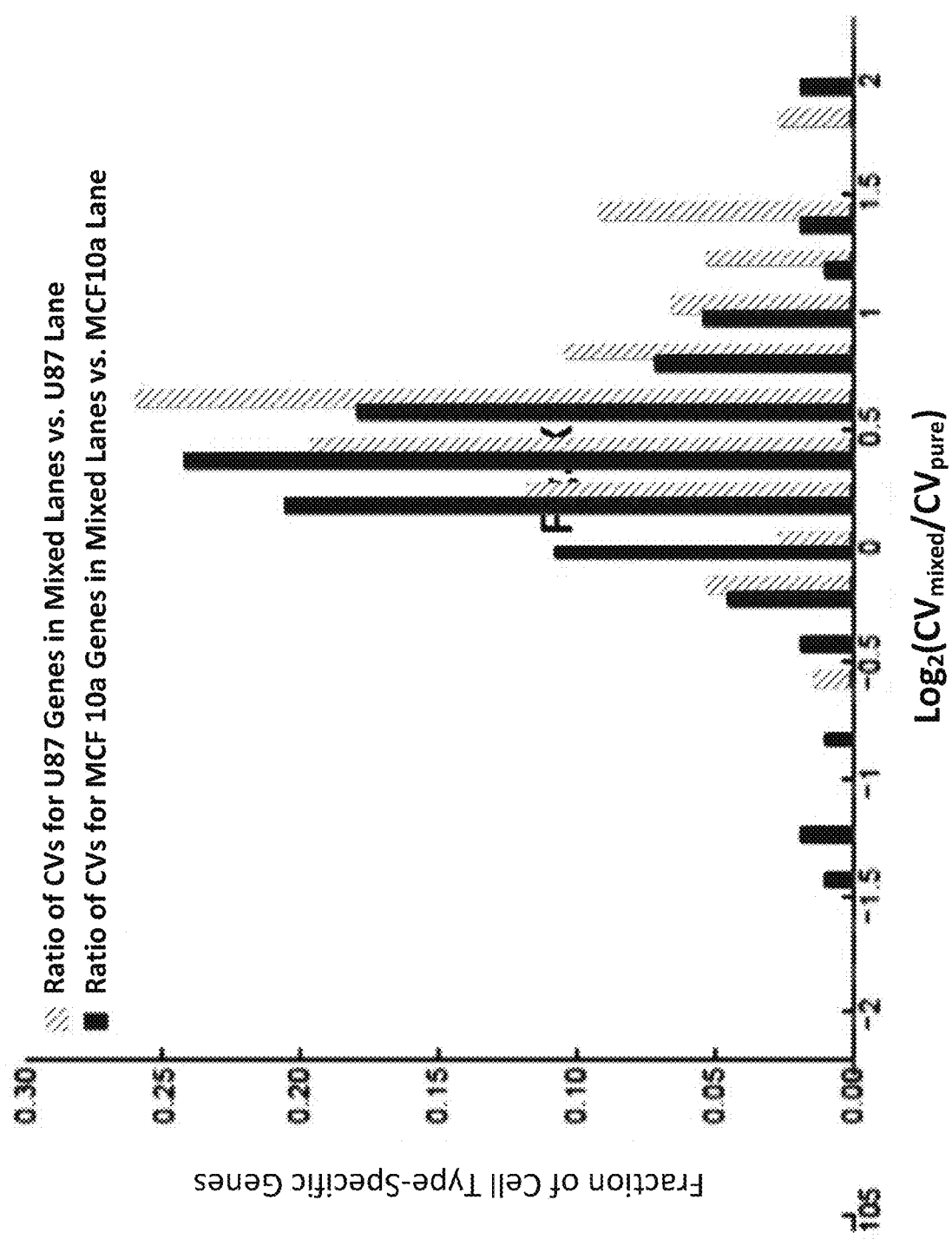

FIGS. 7A-7C provide for (FIG. 7A) a comparison of single cell median and population-level RNA-Seq profiles for cells originating from the U87-exclusive lane in Experiment 1. Each data point was obtained by constructing a median profile from a given number of cells and repeating this ten times by random sampling with replacement to obtain a median Pearson correlation coefficient and error bar (SEM). This exercise was repeated for comparison to both the U87 and MCF10a bulk RNA-Seq profiles to demonstrate better concordance between the U87 single cell profiles and the U87 bulk profile. FIG. 7B provides for the same as FIG. 7A, but for single cell profiles in the MCF10a-exlusive lane. As shown in FIG. 7C, differential expression analysis was conducted to obtain cell type-specific gene sets for the U87 and MCF10a cells based on single cell profiles from the pure-cell lanes. Here, we show a histogram of log-ratio of the coefficients of variation (CVs) for the cell type-specific gene sets between the mixed lane profiles and the profiles from the respective pure lanes. As expected, the heterogeneity given by CV is greater for cells in the mixed lanes than in the cell type-exclusive lanes for the cell type-specific genes.

Figure 8B:
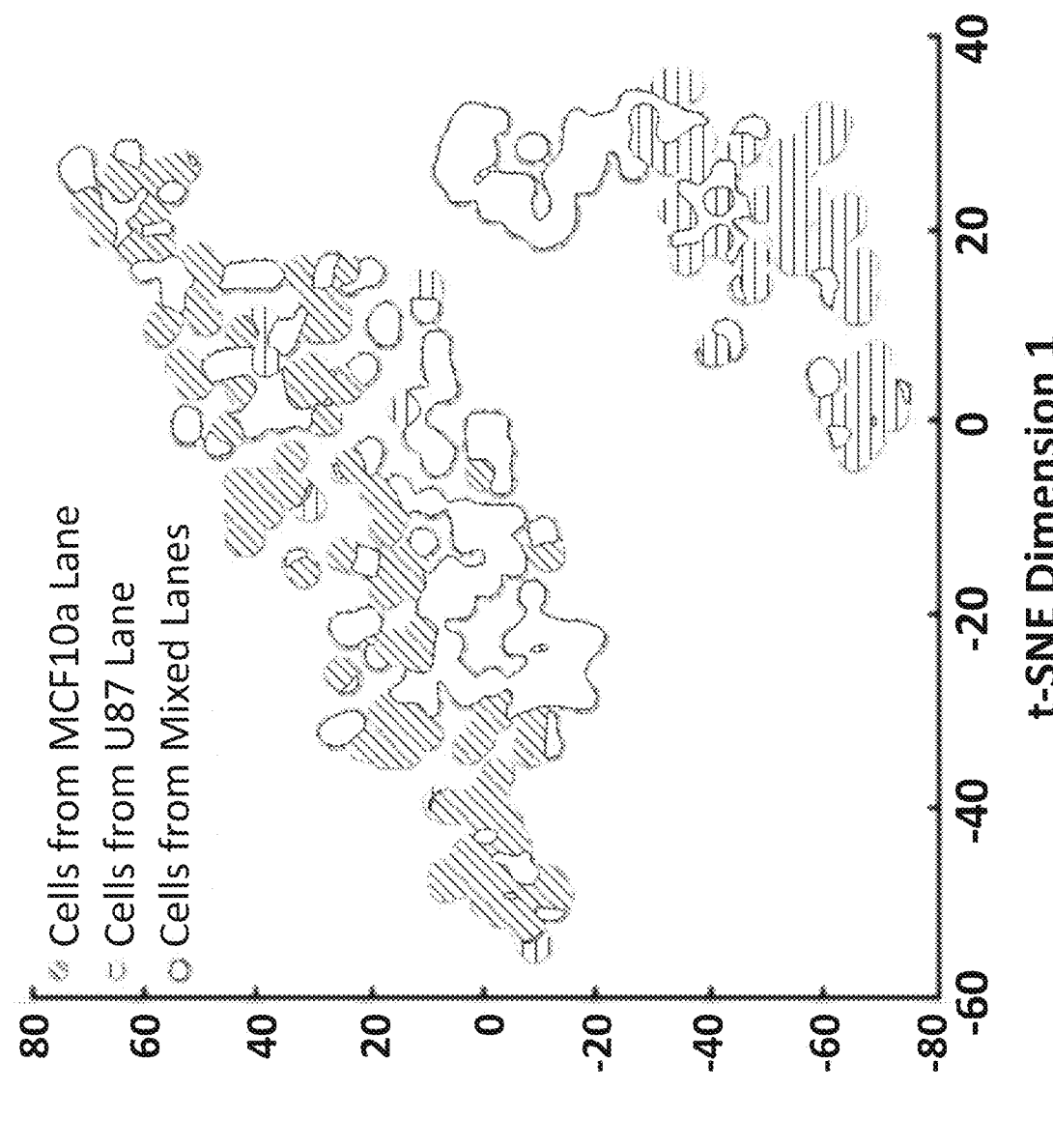
Figure 8C:
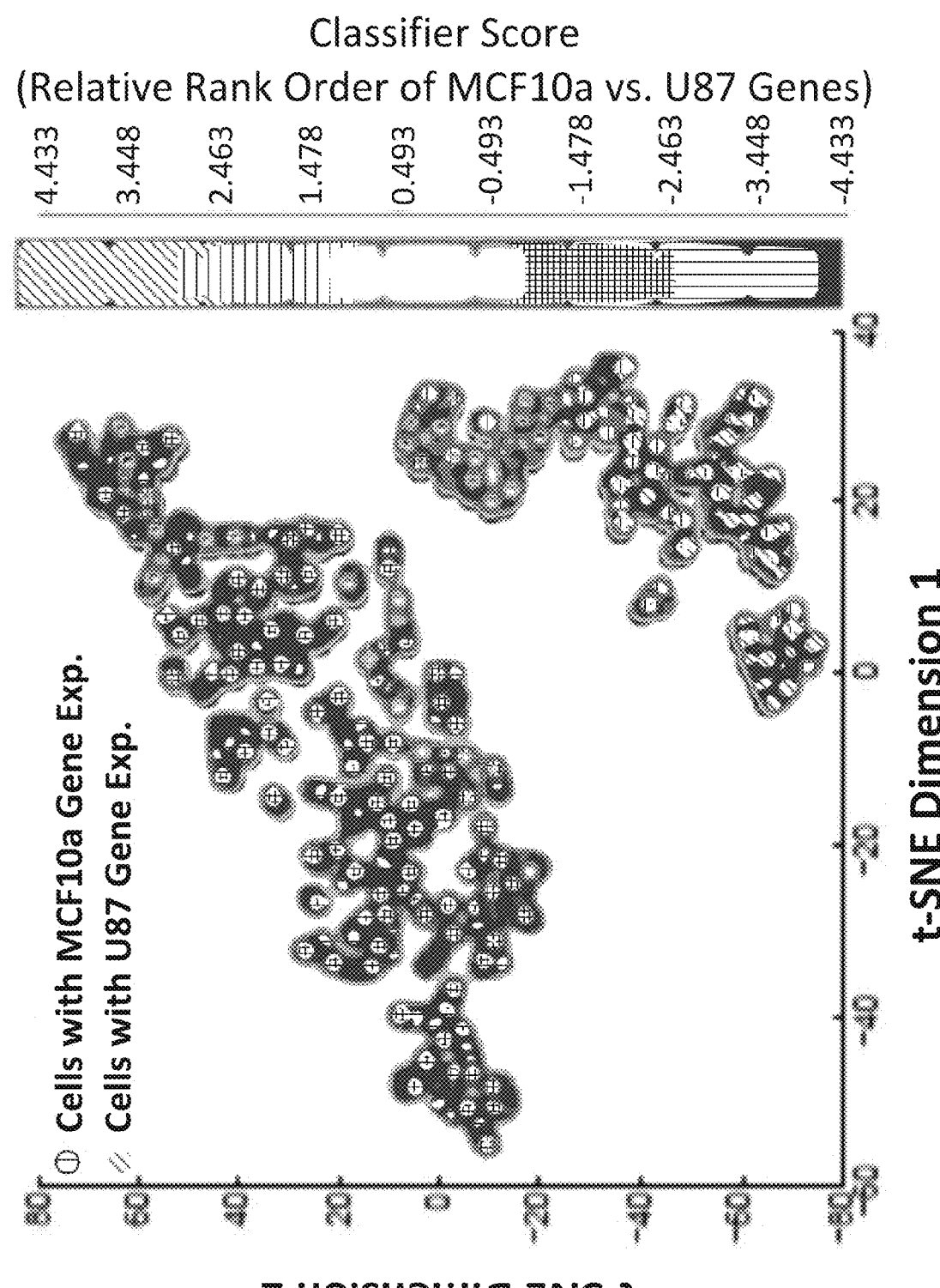

FIGS. 8A-8C provide for cell type separation by single cell RNA-Seq. FIG. 8A: iPAGE gene ontology/pathway analysis based on rank-ordering of differentially expressed genes using $+/-(1-p)$ where p is the p-value for differential expression between the U87- and MCF10a-exclusive lanes given by the Wilcoxin rank-sum test. Values are positive for genes more highly expressed in U87 and negative for genes more highly expressed in MCF10a. FIG. 8B: t-SNE clustering of 396 single cell profiles based on the differentially expressed genes color-coated by the lane-of-origin of each profile. Two clear spatial clusters form and each is predominantly associated with a specific cell type-exclusive lane. FIG. 8C shows the same t-SNE clustering shown in (FIG. 8B) but color-coated with a score indicating expression of the U87-specific genes vs. the MCF10a-specific genes. The score is based on the relative rank ordering of U87- and MCF10a-specific genes in each cell.

Figure 9:
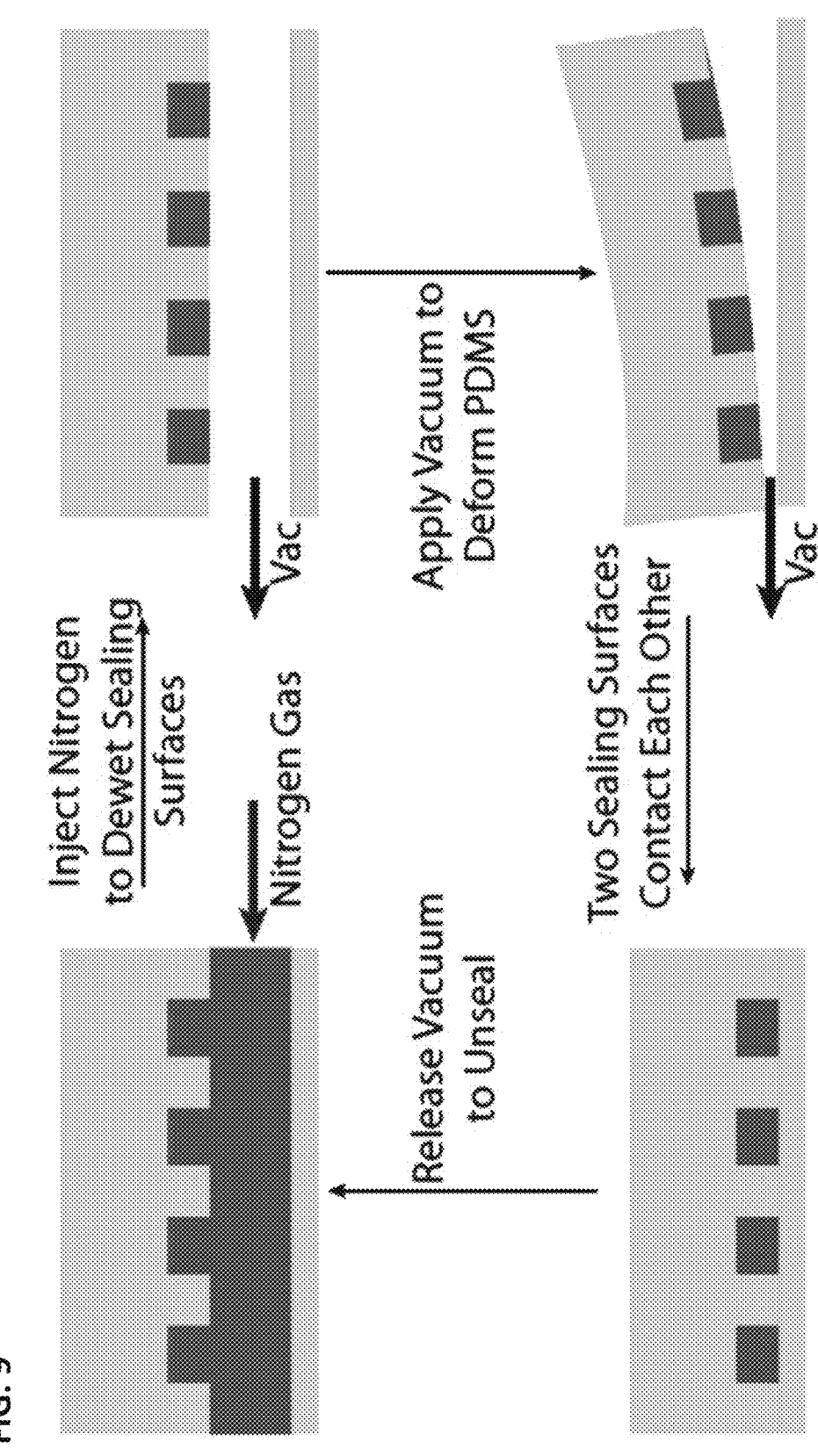

FIG. 9 provides for a schematic of a reversible PDMS-based device in one aspect of the disclosure.

Figure 10:
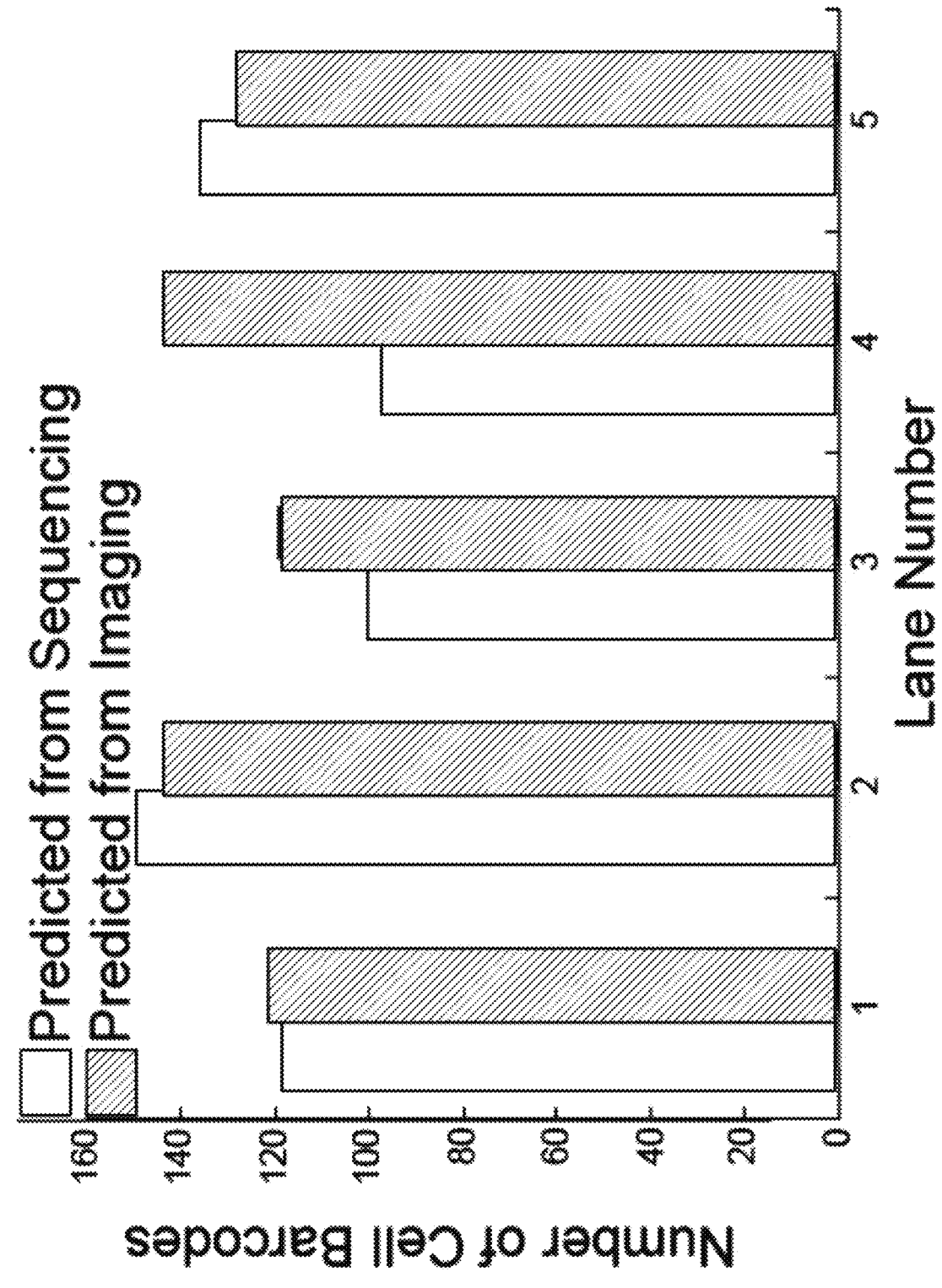

FIG. 10 describes ingle Cell RNA-Seq of U87 and MCF10a Cell Lines ~600 cells paired with beads in five-lane microfluidic device.

Figure 11:
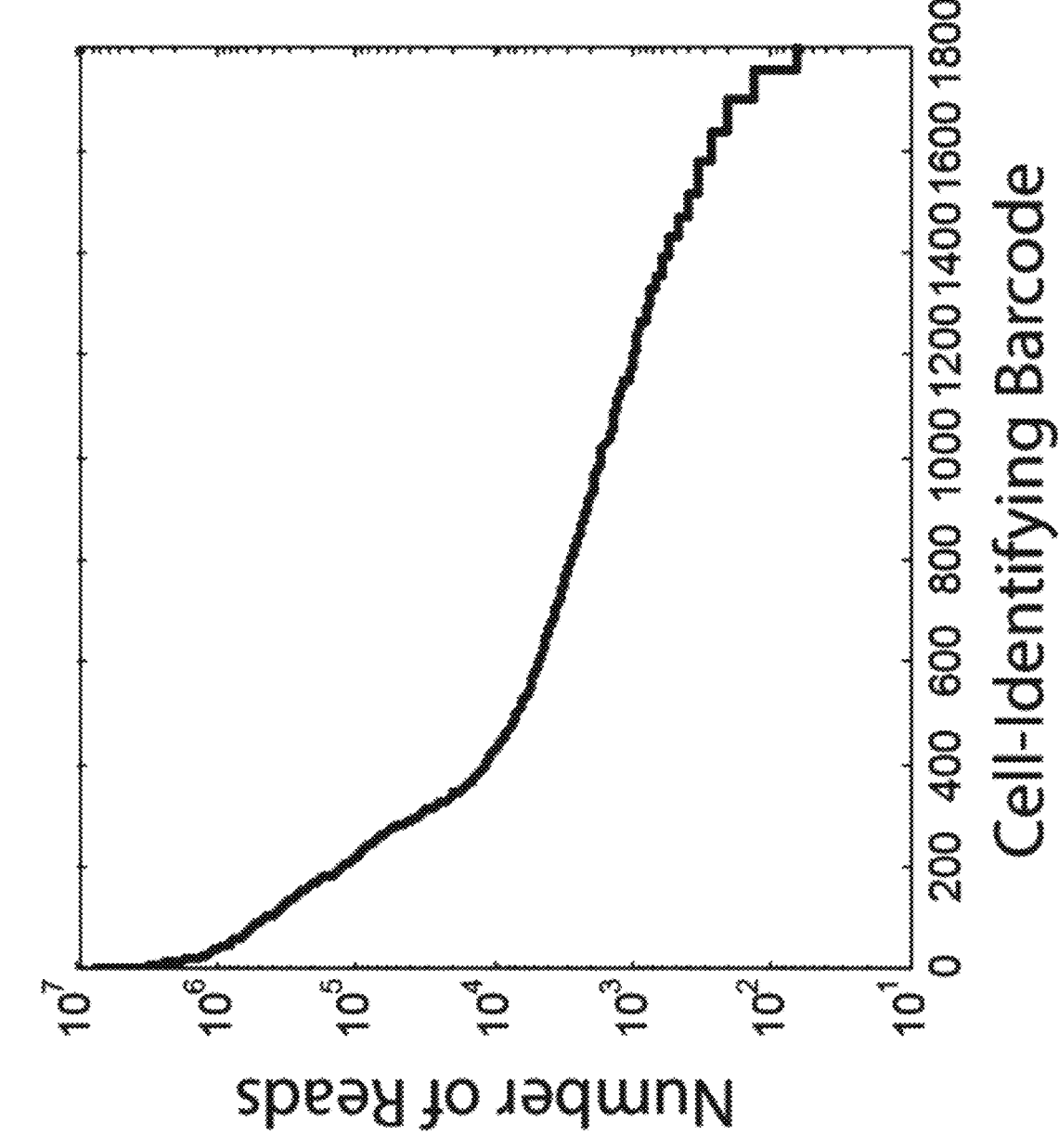

FIG. 11 shows the number of reads associated with each cell-identifying barcode showing a sharp change in slope at ~350 barcodes, consistent with the ~350 cell-bead pairs loaded in the microwell array. The remaining cell-identifying barcodes originate either from sequencing error or ambient, background mRNA hybridizing to beads in the device that were not associated with a cell.

Figure 12:
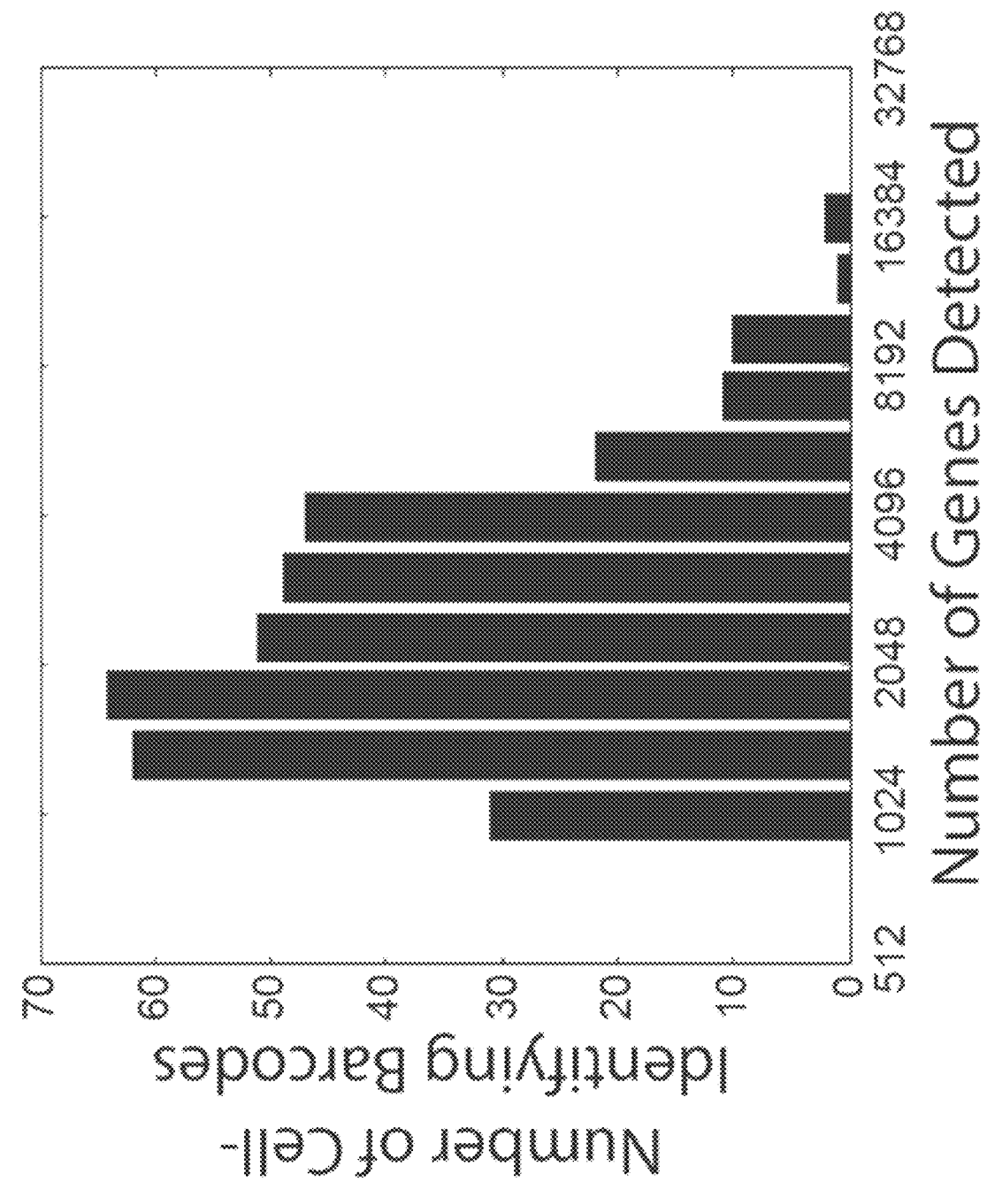

FIG. 12 is a histogram showing that the number of genes detected per individual cell ranges from 1,000 to 17,000 (~3,400 genes per cell on average).

Figure 13A:
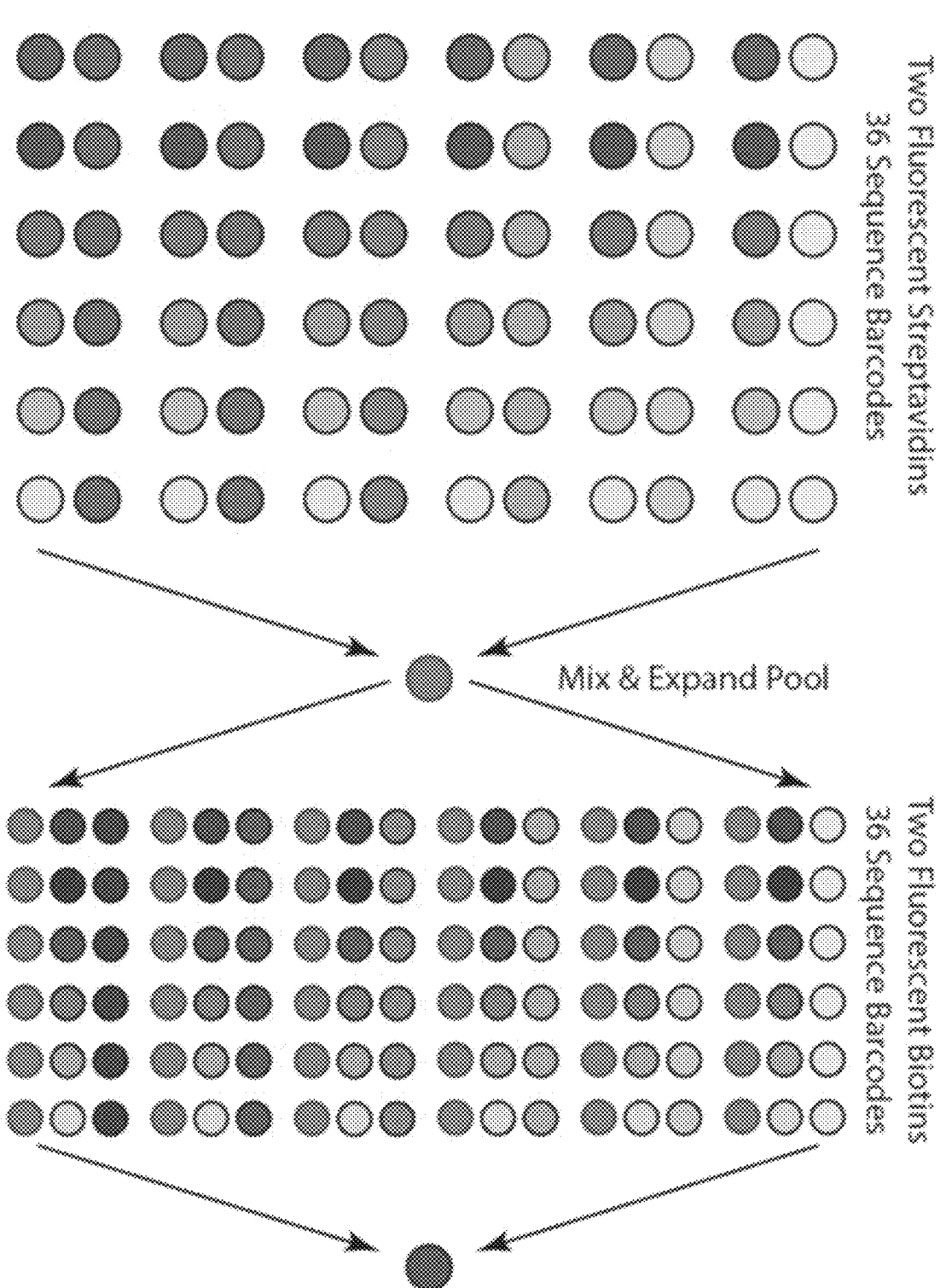
Figure 13B:
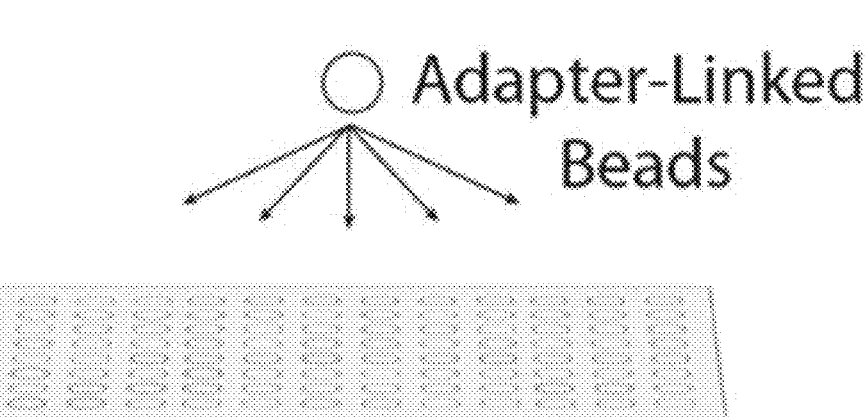
Figure 13B:
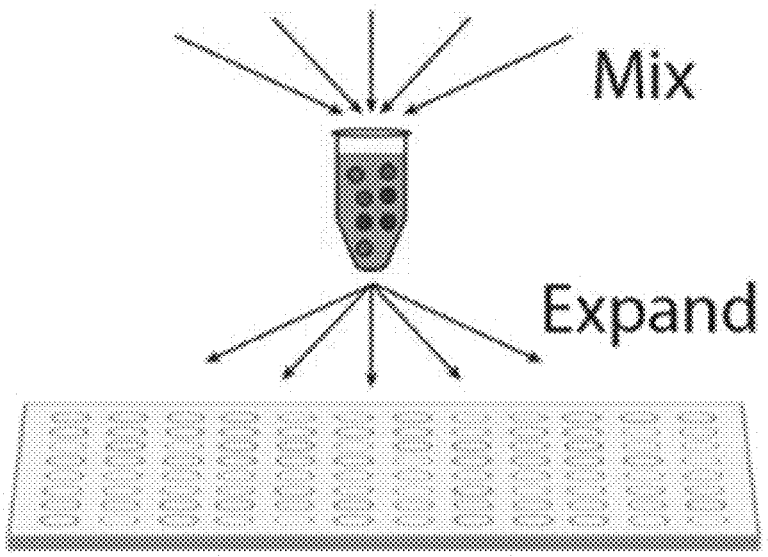
Figure 13B:
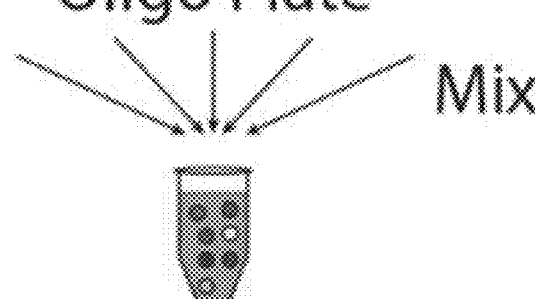

FIG. 13A and FIG. 13B describes a representative example of the capabilities described herein for linking high content imaging to single cell sequencing. For example, introducing 4 different at 6 intensities generates 64 or 1296 optical barcodes (FIG. 13A).

Figure 14A:
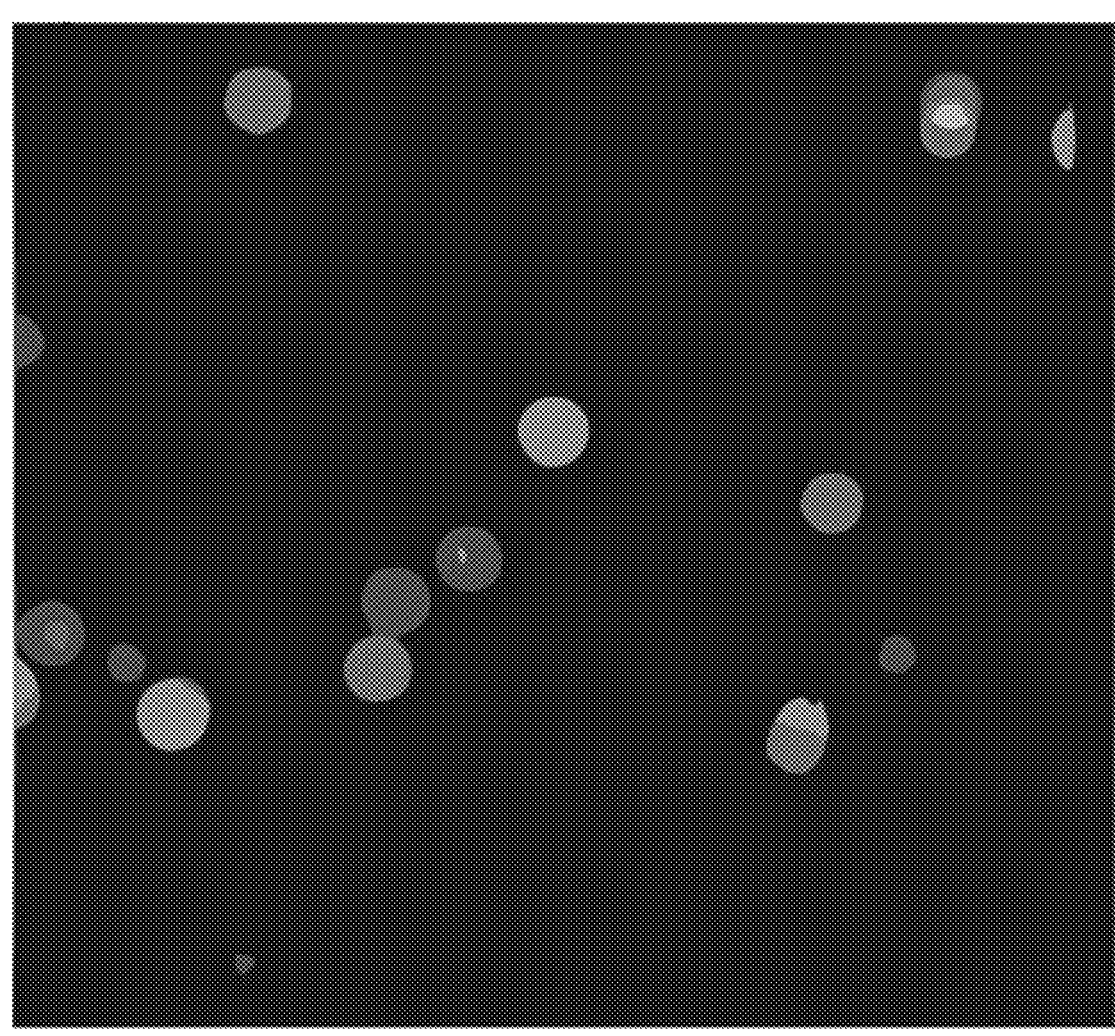
Figure 14B:
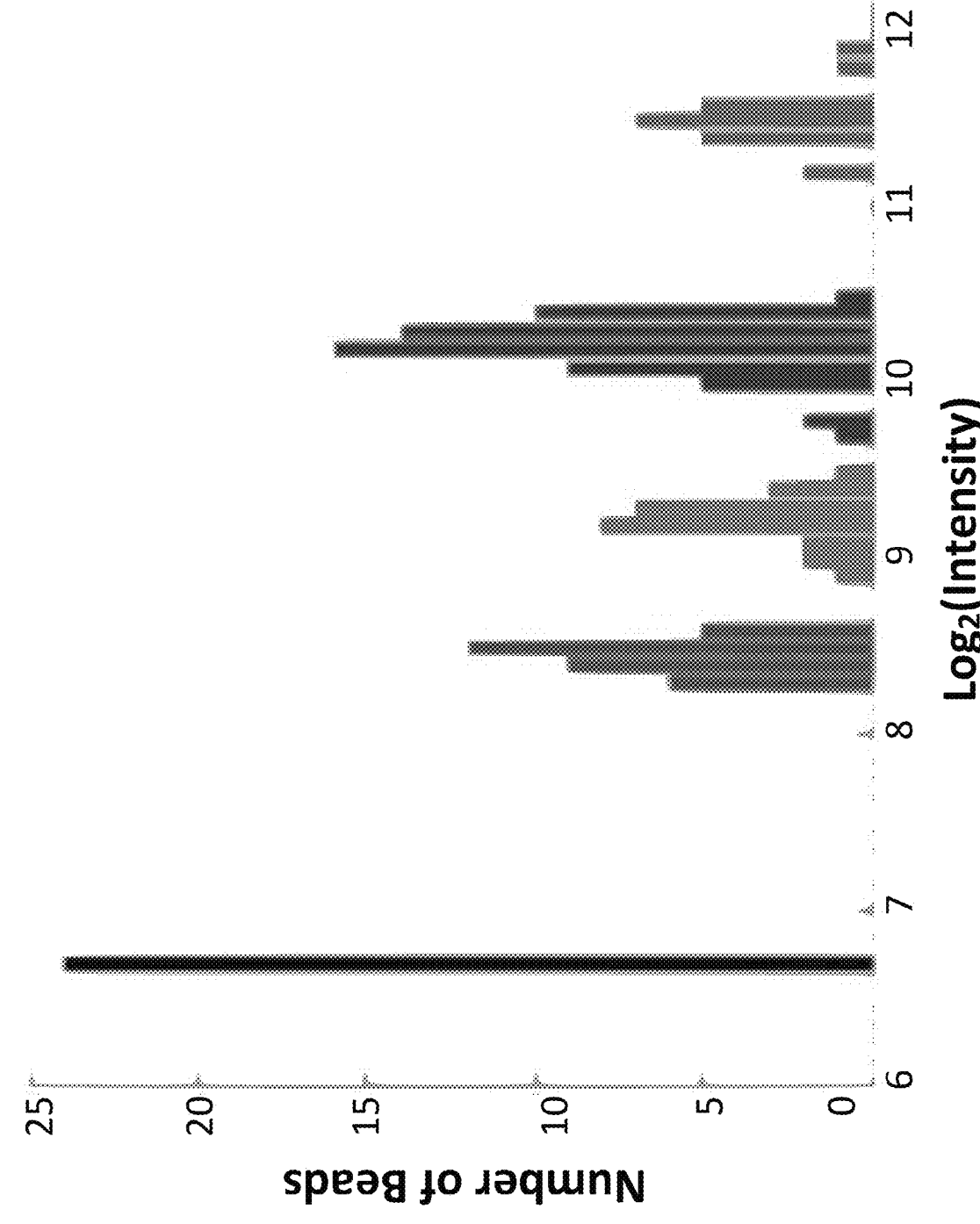

FIGS. 14A and 14B provides for (FIG. 14A) a fluorescence image of beads with different fluorescent colors generated by combinatorial mixing of different fluorescent dyes at different concentrations. Each color combination and intensity represents a different sequence barcode for mRNA capture that is also attached to the bead. In this example the optical barcodes themselves are not sequences. FIG. 14B shows the intensity distribution for the beads in one of the three fluorescence channels demonstrating our ability to separate the optical barcodes based on fluorescence intensity (in this case with five different intensity levels).

DETAILED DESCRIPTION

In an aspect, the disclosure provides for a microwell array system, devices, and methods for pairing individual cells with mRNA capture beads. In another aspect, the disclosure provides for a microwell array system, device, and methods for pairing individual cells with mRNA capture beads that introduce, cell-identifying barcode sequences into cDNA generated after mRNA capture. In an aspect, the system is compatible with high-content cellular imaging and drug stimulation experiments.

The disclosure further provides for capture beads, for example a mRNA capture beads, or probes comprising one or more optical barcodes described herein. In an aspect, the capture beads, for example a mRNA capture beads, or probes are used to identify drug and/or to be used in drug simulation experiments.

In an aspect, the disclosure provides for devices, systems, and/or methods wherein cells are arranged in a grid and/or a chamber. In yet another aspect, the disclosure provides for devices, systems, and/or methods wherein cells are arranged in a grid and/or chamber as compared to devices, systems, and/or methods wherein cells are arranged in droplets or a configuration where cells are physically segregated from one another. In an aspect, a microfluidic device, system, or method described herein comprises a flow cell with an array of microwells embedded in either the top or bottom of the device. In another aspect, the device described herein is a solid state device that allows for single cell isolation, imaging, and/or uniform parallel introduction of reagents to a plurality of cells.

The disclosure provides for devices, systems, and/or methods wherein cells are arranged in a reversible chamber or microchamber wherein the chamber and/or microchamber can be open and/or closed. The disclosure also provides for devices, systems, and/or methods wherein cells are arranged in reversible chamber or microchamber where the chamber and/or microchamber can be opened or closed as compared to devices, systems, and/or methods wherein cells are arranged in non-reversible droplets or a non-reversible configuration wherein cells are physically segregated from one another. In such a non-reversible configuration, the droplets and/non-reversible configuration wherein cells are physically segregated cannot be readily toggled back and forth, that is, may not be opened or closed. As a result, in a non-reversible configuration, fluidics cannot be uniformly distributed to the cells and then uniformly removed and replaced by a second fluid.

The disclosure further provides for devices or system comprising (a) one or more capture beads, for example mRNA capture beads;

(b) one or more cell-identifying barcode sequences, for example, optical barcode sequences;

(c) a plurality of chambers or microchambers including one or more mRNA capture beads and/or one or more cell-identifying barcode sequences;

(d) wherein the plurality of chambers or microchambers including one or more mRNA capture beads and/or one or more cell-identifying barcode sequences are reversible and are capable of being opened or closed more than a single time.

In an aspect, the disclosure provides for devices or system comprising (a) one or more mRNA capture beads;

(b) one or more cell-identifying barcode sequences;

(c) a plurality of chambers or microchambers including one or more mRNA capture beads and/or one or more cell-identifying barcode sequences;

(d) wherein the plurality of chambers or microchambers including one or more mRNA capture beads and/or one or more cell-identifying barcode sequences are reversible and are capable of being opened or closed more than a single time; and (e) wherein the device or system does not comprise a droplet microfluidics device or does not include droplet microfluidic technology, nonoliter droplet technology, and/or droplet sequence, "Drop-seq," "Drop-seq single cell analysis" technology, and/or technology wherein cells are captured in "droplets."

The disclosure further provides for probes comprising one or more mRNA capture beads and one or more cell-identifying barcode sequences associated or coupled with the one or more mRNA capture beads.

The disclosure further provides for compositions comprising one or more mRNA capture beads and one or more cell-identifying barcode sequences associated or coupled with the one or more mRNA capture beads and one or more cells.

The disclosure further provides for methods of drug discovery, drug profiling, and/or drug testing comprising (a) combining one or more mRNA capture beads with one or more cell-identifying barcode sequences;

(b) adding one or more mRNA capture beads with one or more cell-identifying barcode sequences to a plurality of chambers or microchambers;

(c) wherein the plurality of chambers or microchambers including one or more mRNA capture beads and one or more cell-identifying barcode sequences are reversible; and (d) adding one or more drugs to the reversible chambers or reversible microchambers.

The disclosure further provides for a probe comprising (a) one or more mRNA capture beads;

(b) one or more cell-identifying barcode sequences, for example, optical barcode sequences;

(c) a plurality of chambers or microchambers including one or more mRNA capture beads and/or one or more cell-identifying barcode sequences;

(d) wherein the plurality of chambers or microchambers including one or more mRNA capture beads and/or one or more cell-identifying barcode sequences are reversible and are capable of being opened or closed more than a single time The disclosure further provides for methods for single cell RNA capture and sequencing, wherein said method comprises (a) introducing at least one cell into a microwell, wherein the microwell is attached to a first substrate that faces a second substrate and wherein oligo primers are attached to the surface of said second substrate;

(b) hybridizing mRNA molecules to the surface of said second substrate;

(c) adding at least one buffer to the microwell;

(d) contacting said first substrate with said second substrate, thereby creating a seal between said first substrate and said second substrate.

In an aspect, the device, system, and/or microarray is imaged using florescence.

In another aspect, the disclosure provides for a device for single cell RNA capture and sequencing, wherein said device comprises a plurality of microwells; wherein said plurality of microwells are attached to a first polysiloxane substrate; a second substrate comprising glass that faces said first substrate, wherein oligo primers are grafted onto to the glass surface of said second substrate.

In an aspect, the substrate or surface comprises a polysiloxane substrate. In an aspect, the polysiloxane substrate comprises PDMS. In another aspect, the substrate comprises polymethylmethyacrylate (PMMA). In another aspect, the substrate comprises a thermoplastic for fabrication by, for example, hot embossing. In another aspect, the substrate comprises glass for fabrication by, for example laser machining. In another aspect, the substrate comprises silicon or silicon-on-glass or photoresist-on-silicon.

In another aspect, a system or device described herein further comprises one or more drugs, buffers, active agents, and/or a plurality of cells.

In an aspect, the disclosure provides for devices, systems, methods, and/or probes capable of profiling as hundreds or thousands of cells from an organ or tumor. In an aspect, the cells analyzed are healthy human cells, abnormal cells, cancer cells, neural cells, immune cells, epithelial cells, mesenchymal cells, or stem cells. Cells could also originate from microorganisms including parasites, fungi, or bacteria. Other units containing nucleic acids such as viruses both in isolation or inside of an infected host cell could be analyzed.

In yet another aspect, different drugs or chemical constituents or compositions, for example, lysis buffer, may be introduced to a device or system described herein, for example, in a chamber or microchamber, at any time given the reversible nature of the chambers or microchambers. This provides for additional flexibility and advantages over other devices or systems, such as those employing, for example, droplet microfluidic technology, nanoliter droplet technology, and/or droplet sequence, "Drop-seq," "Drop-seq single cell analysis" technology, and/or technology where cells are captured in "droplets."

In an aspect, the device or system described herein, for example, the microfluidic device does not involve any on-chip valves and/or moving parts, which can result in a high feature density. In another aspect, the device or system described herein is not a droplet microfluidics device or does not include droplet microfluidic technology, nonoliter droplet technology, and/or droplet sequence, "Drop-seq," "Drop-seq single cell analysis" technology, and/or technology where cells are captured in "droplets." In an aspect, the device or system described herein is more compatible with cell culture and cell perturbation assays than a droplet microfluidic device because fluids can be readily exchanged in a uniform fashion and cells can communicate with each other via diffusible factors. Hence, cell viability will be higher and cells will exhibit normal physiology in comparison to cells that are sequestered in droplets. In another aspect, in the device or system described herein, cell are arranged in regular array and are in contact with a flat, optically transparent surface as opposed to a droplet microfluidic device in which cells are isolated inside of a spherical enclosure. Therefore, in yet another aspect, the device or system described herein is intrinsically more compatible with imaging, for example optical imaging or microscopy, than droplet devices.

In an aspect, devices, systems, and methods described herein have a higher throughput than devices, systems, or methods employing droplet microfluidic technology, nonoliter droplet technology, and/or droplet sequence, "Drop-seq," "Drop-seq single cell analysis" technology, and/or technology where cells are captured in "droplets." In yet another aspect, analysis of cells, probes, and beads using devices, systems, and methods described herein have a throughput that is 5, 10, 15, 20, 25, or 100 or more times less expensive than devices, systems, or methods employing droplet microfluidic technology, nonoliter droplet technology, and/or droplet sequence, "Drop-seq," "Drop-seq single cell analysis" technology, and/or technology were cells are captured in "droplets."

In another aspect, the device described herein is compatible with automation, for example, a computer-controlled system that is capable of facilitating automated introduction of any of various fluids to the device, temperature control, and reversible sealing of the microwells. Accordingly, in a preferred aspect the device described herein can capture mRNA from thousands of individual cells in parallel and produce pooled, single cell RNA-Seq libraries for ~$0.10/ cell.

In an aspect, barcoded capture beads are introduced to the microwell array in either a random process or ordered process. In yet another aspect, barcoded capture beads are introduced into the microwell array in a random process with little or no control over which barcoded capture bead enter each microwell. Under such a scenario, in an aspect, imaging information acquired from the cells in the device is not directly associated with the single cell transcriptomes that ultimately are quantified by deep sequencing. In an aspect, this issue is addressed by introducing barcodes, for example, optical barcodes, to the mRNA capture beads that indicate the sequence barcode attached to each bead. In another aspect, the optical barcodes can be read out using the same or different fluorescence microscope used for live cell imaging on the device. In yet another aspect, the disclosure provides for a reagent that allows for the capture RNA from individual cells, allows for association of a unique sequence barcode with each single cell cDNA library, and/or reveals the identity of the attached sequence barcode by optical methods.

In an aspect, the disclosure provides for an optical barcode and associated methods described herein. In an aspect, the optical barcode is a sequence. In another aspect, the optical barcode is not a sequence. In another aspect, optical barcodes described herein are not DNA sequences.

In an aspect, an optical barcode described herein comprises a combination of fluorescent dyes comprising at least one different color and optionally more than one different intensity that make the bead uniquely identifiable on an optical microscope. In another aspect, an optical barcode described herein comprises a combination of fluorescent dyes comprising two, three, four, five or more different colors and optionally more than one different intensity that make a respective bead uniquely identifiable on an optical microscope The disclosure further provides for proteomic methods and systems utilizing a device, probe, or bead described herein. In an aspect, an oligonucleotide-based optical barcode is loaded onto beads that also harbor reactive groups for capturing protein (e.g. amine-, carboxyl-, or thiol-reactive groups). In yet another aspect, optical barcodes are loaded onto beads along with one or more antibodies capable of capturing specific proteins. Proteins can be quantified by fluorescence methods (e.g. fluorescently labeled antibodies) or mass spectrometry. In a further aspect, the disclosure provides for the use of DNA-labeled antibodies that are amplified, identified, and quantified by deep sequencing.

The devices, systems, and methods described herein provide for key distinctions and advantages over other devices, systems, and methods. For example, the microwell array device is constructed in such a way that it can be reversibly sealed during cell lysis and RNA capture. Significant loss of RNA occurs in our arrays when cells are lysed in unsealed or even imperfectly sealed arrays due to rapid diffusion of RNA molecules. In the context of the bead capture and RNA-Seq experiments, this could result not only in reduced RNA capture, but also significant cross-talk. Herein, advantage is taken of the physical properties of PDMS, namely its flexibility and hydrophobicity, for high-fidelity, reversible sealing which is difficult to achieve using the agarose hydrogel device reported previously. In addition, the devices, systems, and methods described herein demonstrate genome-wide single cell RNA-Seq. Additionally, the single cell capture and pooled library preparation scheme described herein costs $0.10-$0.20/cell even at a relatively modest scale of several hundred cells per run (see, for example, Table 7), compared to the <$1/cell estimated at the 10,000- cell scale for alternative approach, for example, one described in Fan H C, Fu G K, Fodor S P A: Combinatorial labeling of single cells for gene expression cytometry. *Science* 2015, 347:628-636, which is herein incorporated by reference in its entirety.

In an aspect, the disclosure provides for optical demultiplexing or optical barcoding of sequence-barcoded capture beads by, for example, attaching a unique combination of short oligonucleotides to each bead. In an aspect, while the sequence barcode associated with the RNA capture primer can be read out by DNA sequencing, the optical barcode can be read out on a standard fluorescence microscope. In another aspect, the oligonucleotide combination is unique to each sequence barcode and can be identified by hybridizing fluorescently labeled complementary oligonucleotides to beads. The presence or absence of a series of fluorescently labeled oligonucleotides on each bead after hybridization indicates the unique combination of short oligonucleotides attached to each bead and therefore the sequence barcode attached to each bead. Once the sequence barcode attached to each bead is identified, single cell transcriptome captured on each bead can be identified and read out using a sequencer with phenotypic information obtained from imaging the cells associated with each bead in each microwell of our device.

In an aspect, optical barcoding technology described herein is combined with applications beyond single cell RNA-Seq. In an aspect, an extension of the invention is bulk RNA-Seq or RNA-Seq of small numbers of cells. These can be seeded in the microwells or propagated from a single cell seeded in each microwell. The disclosure further provides for single cell DNA-Seq. The disclosure further provides for barcoded capture oligonucleotides that contain oligo(dT) for capturing mRNA from individual eukaryotic cells. Alternatively, the beads are functionalized with primers that are specific to targeted DNA loci or RNA transcripts. In yet another aspect, the beads are functionalized with primers that have a random sequence and can therefore capture any DNA or RNA sequence from an individual cell. In an aspect, in each case, a corresponding optical barcode is used to link imaging data acquired for a target cell or group of cells and sequencing data acquired from whatever nucleic acids are captured on the bead.

The disclosure further provides for proteomic methods and systems utilizing a device described herein. In an aspect, an oligonucleotide-based optical barcode is loaded onto beads that also harbor reactive groups for capturing protein (e.g. amine-, carboxyl-, or thiol-reactive groups). In yet another aspect, optical barcodes are loaded onto beads along with one or more antibodies capable of capturing specific proteins. Proteins can be quantified by fluorescence methods (e.g. fluorescently labeled antibodies) or mass spectrometry. In a further aspect, the disclosure provides for the use of DNA-labeled antibodies that are amplified, identified, and quantified by deep sequencing.

Single cell analysis is important for understanding how cells respond to drugs and other perturbations because phenotypic responses are inherently asynchronous and cells PDMS Microwell Flow Cell for Single Cell Transcriptome Capture In an aspect, the microfluidic platform described herein comprises a flow cell with an array of microwells embedded in either the top or bottom of the device. In an aspect, the device or system described herein comprises a high-throughput DNA sequencing and digital PCR device, as described in, for example, White A K, VanInsberghe M, Petriv O I, Hamidi M, Sikorski D, Marra M A, Piret J, Aparicio S, Hansen C L: High-throughput microfluidic single-cell RT-qPCR. *Proceedings of the National Academy of Sciences of the United States of America*, 2011, 108(34):13999-14004 or Men Y, Fu Y, Chen Z, Sims P A, Greenleaf W J, Huang Y: Digital polymerase chain reaction in an array of femtoliter polydimethylsiloxane microreactors. *Anal Chem* 2012, 84(10):4262-4266, the contents of which are incorporated by reference herein in their entirety.

In an aspect, fluids can be driven through the flow cell manually by, for example, laminar flow using a syringe or pipette. Fluid exchange in the microwells occurs by diffusion, while cells and beads can be loaded by gravity. The microwell arrays may be fabricated from, a polysiloxane substrate, for example, polydimethylsiloxane (PDMS), a silicone rubber commonly used in soft lithography. PDMS allows inexpensive, rapid, and repeatable fabrication from molds produced on silicon in photoresist using standard photolithography. See, for example, McDonald J C, Whitesides G M: Poly(dimethylsiloxane) as a material for fabricating microfluidic devices. *Accounts of chemical research* 2002, 35(7):491-499 and *First Single Cell Expression Analysis with PDMS*, Marcus et al., *Analytical Chemistry*, 2006 (Quake Lab), which are herein incorporated by reference in their entirety. In addition, the material properties of PDMS, including its hydrophobicity and flexibility, facilitate reversible sealing of the microwells against a flat surface using mechanical deformation and negative pressure (see, for example, FIG. 2A) or introduction of oil by laminar flow (See, for example, FIG. 3A).

In an aspect, the device or system described herein is capable of solid-phase capture of RNA from individual cells via two modes of operation—RNA "printing" on glass and RNA capture on beads. For example, in an aspect, in RNA printing mode, individual cells are loaded in the microwells, which are fabricated in a PDMS slab that faces a glass coverslip. Oligo(dT) primers are covalently grafted to the glass surface so that mature mRNA molecules can be immobilized by hybridization of their poly(A) tails. Following the introduction of lysis buffer, the microwells can be sealed by mechanically placing them in conformal contact with the functionalized glass surface. Cell lysis releases mRNA into the solution confined by the microwells, resulting in hybridization to the oligo(dT)-coated glass coverslip. By placing the flow channel under negative pressure, the seal can be maintained in the absence of mechanical force, making the device transportable and readily accessible to an optical microscope. See, for example, White A K, VanInsberghe M, Petriv O I, Hamidi M, Sikorski D, Marra M A, Piret J, Aparicio S, Hansen C L: High-throughput microfluidic single-cell RT-qPCR. *Proceedings of the National Academy of Sciences of the United States of America* 2011, 108(34):13999-14004, which is herein incorporated by reference in its entirety.

Because the mRNA is immobilized on a glass surface, enzymatic processing steps can take place on-chip, simply by sequential flow of reagents through the device. After incubating the trapped, single cell lysates with the glass capture surface, the seal may be released and the flow cell can be rinsed with a detergent-containing buffer followed by a reaction mixture containing DNase. Because the oligo(dT) primers are comprised of locked nucleic acid (LNA), they are resistant to nuclease digestion. See, for example, Koshkin A A, Nielsen P, Meldgaard M, Rajwanshi V K, Singh S K, Wengel J: LNA (locked nucleic acid): an RNA mimic forming exceedingly stable LNA:LNA duplexes. *Journal of the American Chemical Society* 1998, 120(50):13252-13253, the content of which is incorporated by reference in its entirety.

The immobilized single cell mRNA libraries can then be reverse transcribed in parallel, and the resulting mRNA/cDNA hybrids can be visualized by fluorescence microscopy after staining with a fluorogenic intercalator dye. For example, FIG. 4B illustrates a fluorescence image of single cell transcriptome "prints" arrayed on a glass coverslip as described above. Here, it is further confirmed by running a control experiment that the printed material originates from RNA. While some aggregates of genomic DNA were not fully digested (but are reduced in intensity by DNase treatment), the disclosure further confirms that the vast majority of material imaged in the circular prints originates from RNA. For example, the left-most panel of FIG. 4C shows a bright field image of a microwell array in which three microwells each contain an individual cell. The resulting RNA prints (middle panel) that can be visualized after reverse transcription are ablated by incubating the surface with RNaseH (right-most panel), which selectively digests RNA in RNA/DNA hybrids. Conversion of RNA/DNA hybrids to single-stranded cDNA precludes detection using the intercalator dye, and so removal of RNA from the prints eliminates the fluorescence signal almost completely. FIG. 4C also contains some small fluorescent objects associated with the interstitial walls of the microwell array or with microwells that did not contain a cell. These are substantially reduced in intensity by RNase treatment, confirming that they are, in fact, RNA that is spuriously captured or non-specifically absorbed. These objects could arise due to contamination from dead cells or other sources of freely floating RNA introduced with the cells prior to sealing. Nonetheless, the vast majority of the observed signal in FIG. 4C is associated with the circular mRNA prints that correlate perfectly with microwells that initially contained a cell.

Figure 1A:
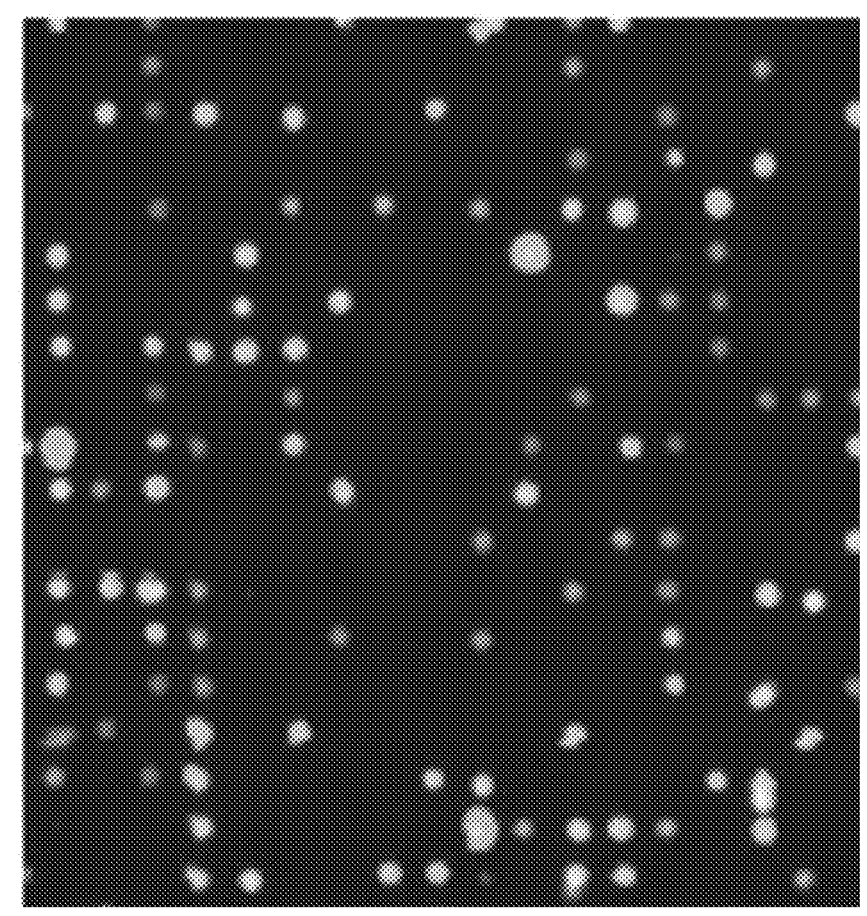
FIG. 1A provides for florescence imaging of a microwell array loaded with optically barcoded beads after introduction and hybridization of a single optical barcode probe. The brighter beads contain optical barcode oligonucleotides that are complimentary to the probe.
Figure 1B:
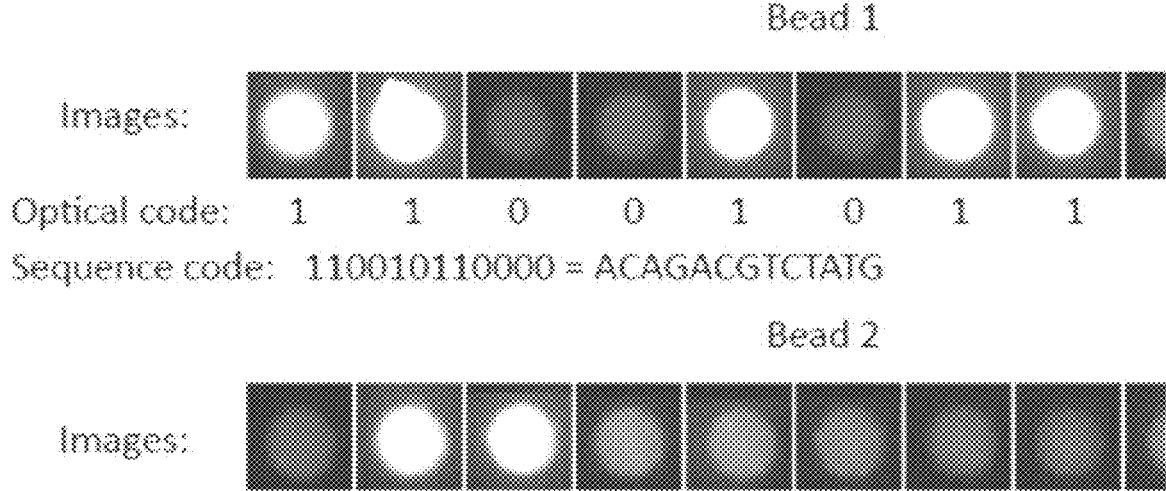
FIG. 1B provides for a series of 12 fluorescence images from each of two beads in the microwell array device after introduction of each of 12 barcoded probes. When a probe is complimentary to optical barcode oligonucleotides on the bead surface, the bead becomes fluorescent, resulting in the 12-digit binary code that corresponds to a sequence attached to the capture oligonucleotide on the bead.
Figure 2A:
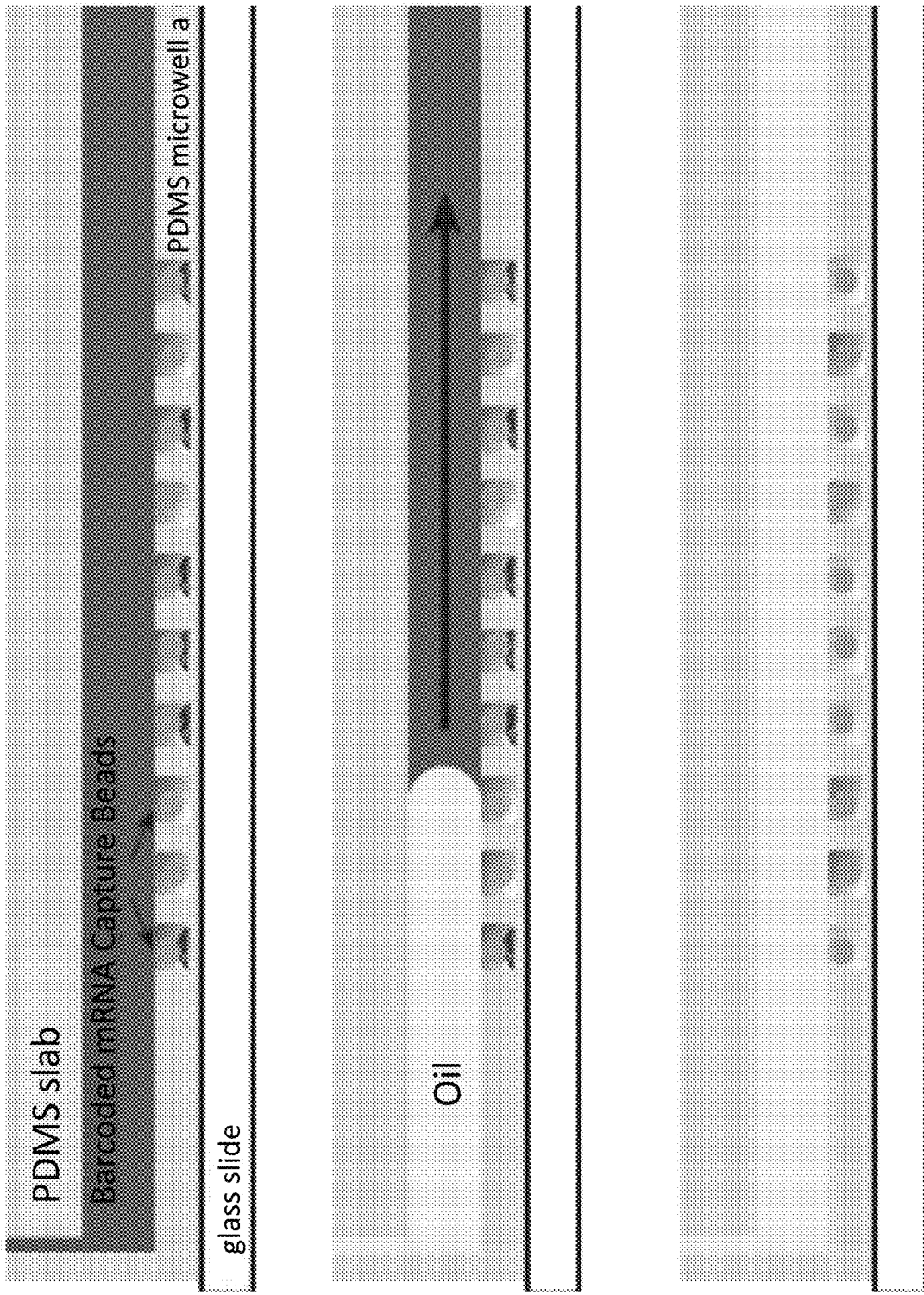
FIG. 2A shows schematic and fluorescence imaging data for single cell RNA capture on beads.
Figure 2B:
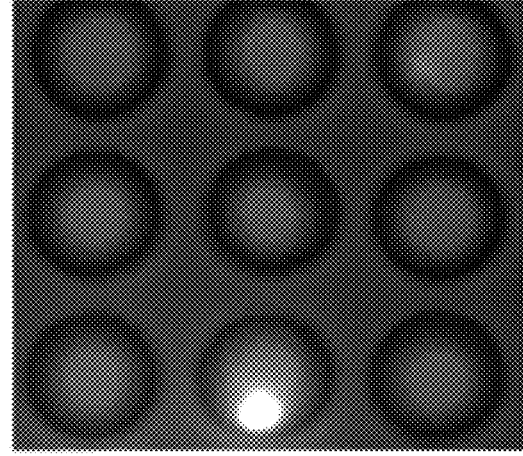
FIG. 2B are close-up images of single cell RNA capture on beads. The top panel is a bright field/fluorescence overlay of a microwell array in which four microwells contain a bead, but only one contains both a bead and a cell (fluorescently labeled with live stain). The middle panel is a fluorescence image of the array after RNA capture, reverse transcription, and staining with SYTOX Orange. Note that the bead associated with a cell is significantly brighter than the other beads. The bottom panel is a fluorescence image of beads in an array from a negative control experiment involving no RNA or cells, showing that the beads have a certain level of background fluorescence in the presence of stain, which explains the majority of the background signal observed in the beads with no cell in the middle panel.
Figure 2B:
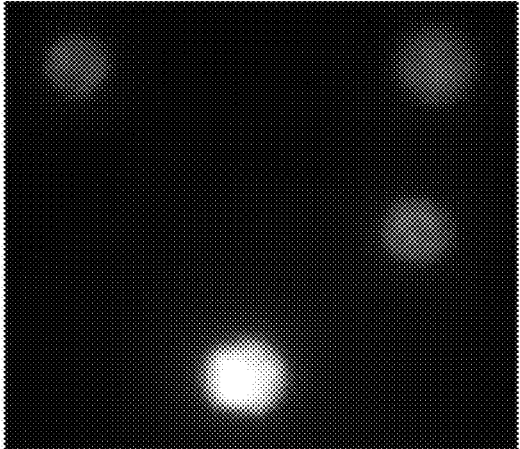
Figure 2B:
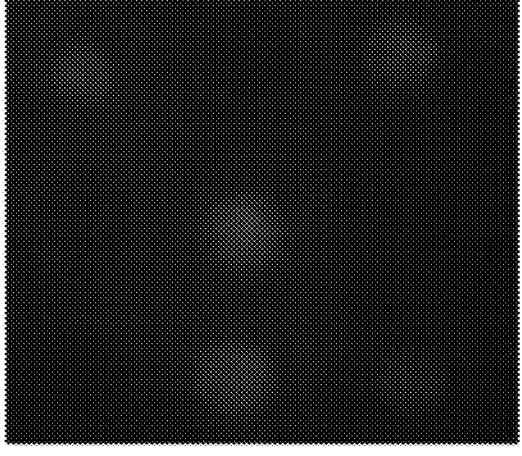

FIG. 4A shows a second, very similar version of the device where the microwells are fabricated in PDMS on a glass slide, and the sealing is accomplished by laminar flow of oil. Using nearly the same procedures as described above for RNA printing mode, we use this version of the device to capture RNA on beads. After introducing cells, we can load beads into the microwells by gravity and achieve super-Poisson loading by using beads with a mean diameter greater than the radius of the microwells. Like the glass surface in FIG. 4A, we coat the beads in oligo(dT) to facilitate mRNA capture after cell lysis and sealing. FIG. 2B shows bright field and fluorescence images of a bead-containing microwell array loaded with individual cells following solid-phase mRNA capture and reverse transcription. The bead contained in a microwell that also contains a cell is substantially more fluorescent following reverse transcription than the other beads. While there is some fluorescence signal associated with beads that do not contain a cell, this is mainly due to non-specific staining of the high-density of single-stranded primers on the bead surface and non-specific staining of the bead itself, as shown in the third panel of FIG. 2B where we depict fluorescence images of beads in the absence of cells, cell lysate, or RNA as a negative control.

A Scalable Platform for Single Cell RNA-Seq

A scalable platform for single cell RNA-Seq based on the bead capture modality is described herein. The low reagent volumes required for microfluidic processing result in a significant cost reduction relative to some conventional methods, for example, as described in Wu A R, Neff N F, Kalisky T, Dalerba P, Treutlein B, Rothenberg M E, Mburu F M, Mantalas G L, Sim S, Clarke M F et al: Quantitative assessment of single-cell RNA-sequencing methods. *Nat Methods* 2014, 11(1):41-46, which is herein incorporated by reference in its entirety.

A further reduction in cost can be realized by, for example, using microfluidics in combination with schemes for cDNA barcoding. A representative example of this, such as the CEL-Seq strategy, can be found in Hashimshony T, Wagner F, Sher N, Yanai I: CEL-Seq: single-cell RNA-Seq by multiplexed linear amplification. *Cell Rep* 2012, 2(3): 666-673, which is herein incorporated by reference in its entirety. By introducing a cell-specific barcode to the cDNA during reverse transcription, all subsequent sequencing library preparation steps can be accomplished on pooled cDNA from multiple cells, further reducing hands-on time and reagent consumption.

Figure 3A:
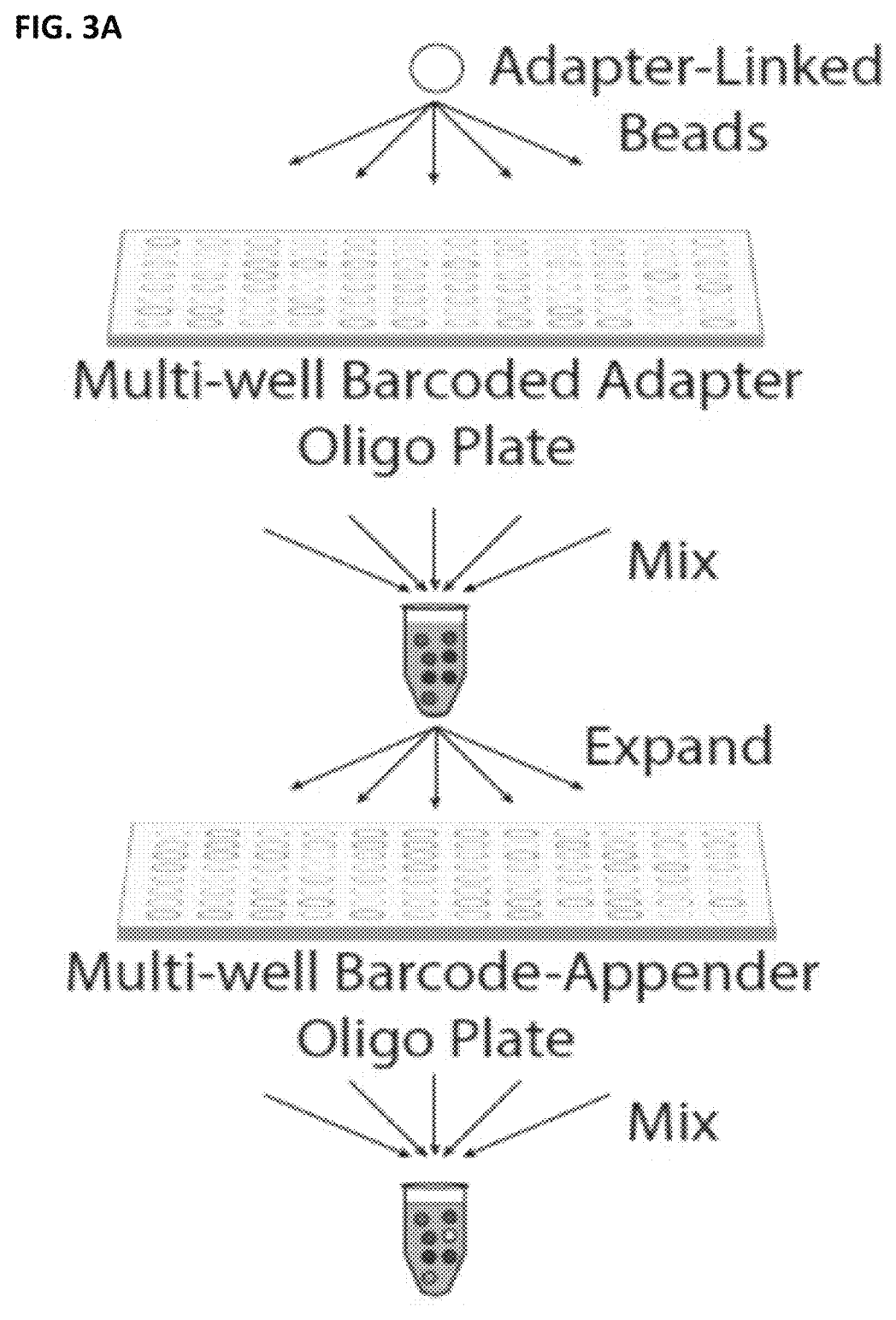
Figure 3B:
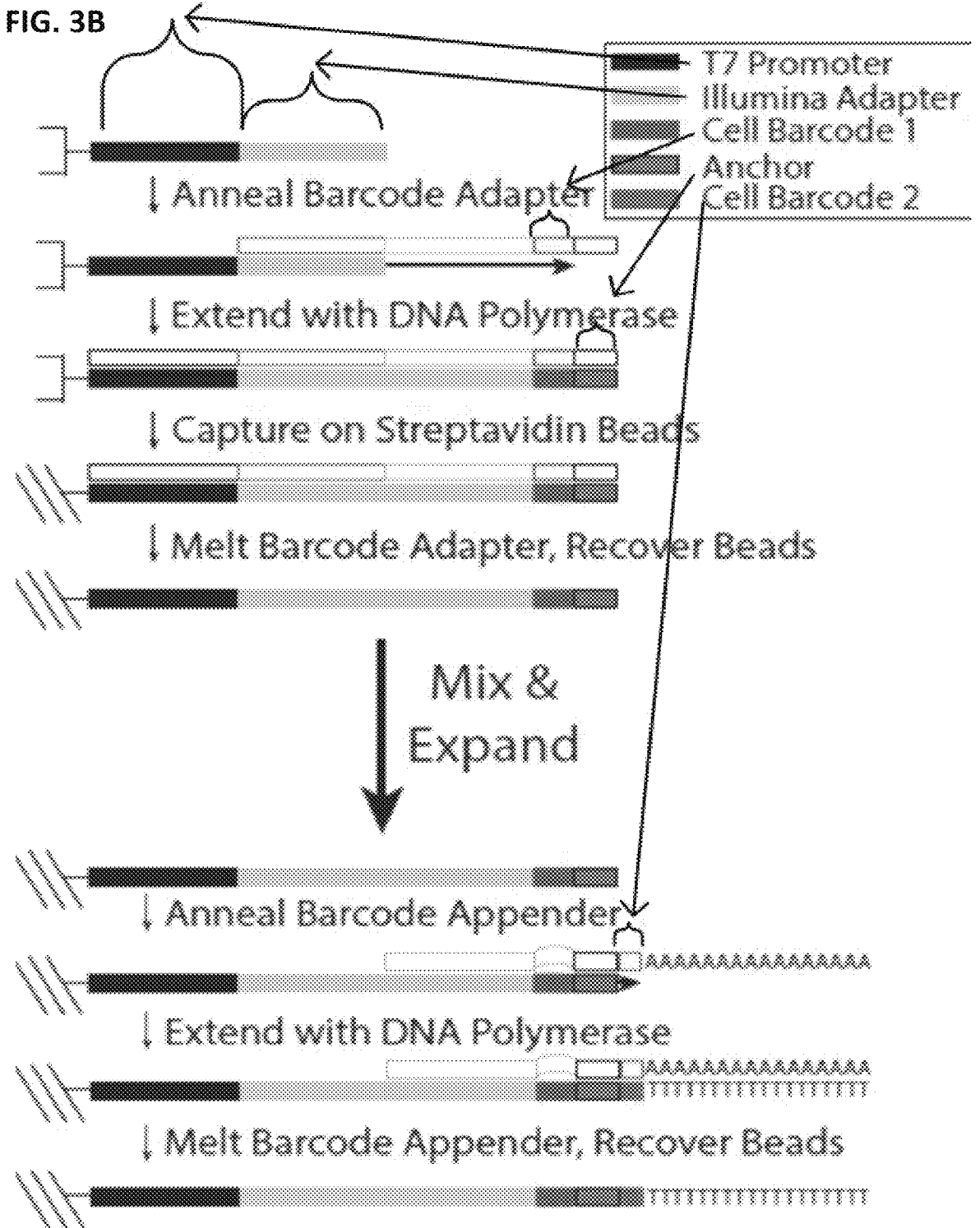

A pool of mRNA capture beads was generated in which each bead is attached to ~1 billion copies of a primer terminated on the 3'-end with one of 960 possible barcode sequences followed by oligo(dT) using a combinatorial synthesis technique (FIGS. 3A and 3B). If, for example, 100 cells loaded into the microwells of a device or system described herein receive a random barcoded bead from the pool, it is expected that the mRNA from ~95 of them would be uniquely labeled based on the binomial distribution. A copy of the T7 promoter sequence (TPS) and part of an Illumina sequencing adapter (ISA) comprise the 5'-end of the capture primer (Table 1) to allow linear pre-amplification by in vitro transcription (IVT) and library enrichment by PCR (FIG. 3B). To create this large pool of barcoded beads, 96 different barcode-containing oligonucleotides (Table 2) were copies onto a dual-biotinylated oligonucleotide containing TPS and ISA by primer extension with DNA polymerase in a 96-well plate. Each barcode is terminated with a universal, 6-base anchor sequence that becomes the 3'-end of the biotinylated oligonucleotide after the first round of primer extension (FIG. 3B). After this first reaction, each barcoded oligonucleotide was immobilized onto a set of streptavidin-coated Sepharose beads, quench the reaction, combine all of the barcoded beads in a pool, and remove original barcode-containing strand by denaturation. At this point, the pool of beads is split into ten new reactions and each containing one of ten unique second barcodes along with poly(dT) (Table 3) are added to the 3'-end of the immobilized oligonucleotide by primer extension from the universal anchor sequence (FIG. 3B). After quenching this reaction, the beads can be pooled, removing the unbiotinylated strands, and washed. The resulting pool of beads contains 960 barcoded capture primers.

A PDMS microwell device containing five flow channel lanes for physical multiplexing of samples and >10,000 microwells was constructed (FIG. 5A). The cylindrical microwells are about 50 μm in diameter and height with a volume of <100 pL. In another aspect, the microwells are about 100 μm to about 5 mm, about 5 μm to about 200 μm, about 10 μm to about 100 μm, about 25 μm to about 75 μm, about 30 μm to about 600 μm in diameter and height. In yet another aspect, the microwells comprise a volume of about 10 pL to about pL, about 10 pL to about 100 pL, about 25 pL to about 75 pL, about 25 pL to about 100 pL. In an aspect, cells are loaded in individual microwells randomly, according to Poisson statistics, such that the majority of cell-containing wells contain one cell. The concentration of the cellular suspension can be tuned in order to avoid overloading the microwell array. For example, if ~100 cells are captured in every 1,000 microwells of a given array, then about <5% of microwells will contain more than one cell. Beads can then be loaded into the wells at a somewhat higher density because the mean diameter of the beads (~30 μm) significantly reduces the probability double-loading (FIG. 5B and FIG. 5C). In an aspect, depending on the size of the microwell, it is rare to observe both beads and cells in an overloaded microwell. Given the pool of 960 cell-identifying barcodes and five lanes, the capacity of the system described herein for single cell RNA-Seq is ~600 cells at a unique barcoding rate of >94%. In another aspect, the capacity of the system described herein for single cell RNA-Seq is ~600 cells at a unique barcoding rate of about greater than 85%, greater than 90%, greater than 91%, greater than 92%, greater than 93%, greater than 94%, greater than 95% or more. In an aspect, the device or systems described herein may be scaled to increase capacity by synthesizing additional barcodes and/or adding microwells to the device or system.

After loading the cells and barcoded beads, procedures described above and herein can be employed to trap single cell lysates in sealed microwells, immobilizing captured mRNA on beads, and reverse transcribe (FIG. 5B). Following on-chip second-strand synthesis, the pool of single cell libraries can be simultaneously elute and pre-amplify overnight by IVT using T7 RNA polymerase (FIG. 5B). The resulting amplified RNA (aRNA) can be removed from each lane using a pipette, reverse transcribe the aRNA from each lane with primers containing lane-identifying barcodes, the cDNA libraries from all five lanes can be pooled, and enrichment of the sequencing library in a single PCR reaction can be undertaken. The primers used for aRNA reverse transcription contain 8-base unique molecular identifiers (UMIs) so that the vast majority of cDNA molecules are distinguishable. That way, genes can be quantified from sequencing data based on the number of UMIs associated with each gene rather than the number of reads, mitigating noise and bias that result from exponential amplification by PCR. See, for example, Shiroguchi K, Jia T Z, Sims P A, Xie X S: Digital RNA sequencing minimizes sequence-dependent bias and amplification noise with optimized single-molecule barcodes. *Proceedings of the National Academy of Sciences* 2012, 109(4):1347-1352 and Shiroguchi K, Jia T Z, Sims P A, Xie X S: Digital RNA sequencing minimizes sequence-dependent bias and amplification noise with optimized single-molecule barcodes. *Proceedings of the National Academy of Sciences* 2012, 109(4):1347-1352, which are incorporated by reference in their entirety.

Demonstration and Analysis of Highly Multiplexed Single Cell RNA-Seq

In an aspect, the microfluidic device described herein is used to obtain RNA-Seq profiles from ~600 cells across five lanes from two commonly used human cancer cell lines (described herein as "Experiment 1" throughout the text). One of the five lanes contained U87 human glioma cells, one contained MCF10a human breast cancer cells, and the other three contained a mixture of both cell lines. These two cell lines are highly mesenchymal, have been cultured for numerous passages, and have relatively similar expression profiles. Nonetheless, they are distinguishable by a few key genes and can be readily separated the data set. In addition, in an aspect, a slightly different protocol with less expensive reagents are used to obtain profiles of ~500 cells across five lanes for a different cell pair (U87 cells and the diploid cell line WI-38, which has not undergone malignant transformation) in Experiment 2.

A factor with any pooled library scheme is cross-talk between cell-identifying barcodes. As described herein, this issue is addressed by quantitative analysis of Experiment 1. For example, the disclosure provides for methodology wherein cross-talk is quantified by using both sequencing and imaging data. In an aspect, because the device or system described herein is compatible with fluorescence micros-copy, a fraction of the streptavidin molecules on each bead can be labelled with red-fluorescent AlexaFluor 647 and pre-stained the cells with a blue-excitable live stain. This allows quantification of the number of cells paired with a barcoded capture bead and also allows for the estimation of the number of barcodes that are expected to be observed in the sequencing data for each lane. The sequencing data reveals that more barcodes are present in the library for each lane than expected based on the imaging data. Analysis reveals that the number of molecules associated with a given barcode placed the barcodes in two distinct populations. The size of the population of barcodes associated with a larger number of molecules was highly consistent with the imaging data (within ~8%), which we take to demarcate our single cell RNA-Seq profiles. The second, larger population of barcodes with relatively few associated molecules likely results from multiple potential sources including sequencing error, actual cross-talk or spurious capture within our micro-fluidic device, and PCR jumping as observed in other implementations of multiplex single cell RNA-Seq. Across all five lanes the cell-identifying barcodes that were not associated with actual cells in the device had 200-300× fewer molecules per barcode than those associated with cells (based on the ratio of median unique molecules in the two populations).

As described in FIGS. 6A and 6B, the systems and devices described herein produce useful single cell RNA-Seq pro-files. For example, in an aspect, the library preparation protocol described herein is based on CEL-Seq where, rather than sequencing the full gene body and normalizing by transcript length, the 3'-end of transcripts are sequenced and counted. FIGS. 6A and 6B show the expected distribution of mapping positions for 3'-end sequencing, with most reads mapping to the 3'-UTRs or coding sequences. Subsequent analysis to demonstrate cell type separation using our data set will rely on the 396 single cell profiles that we obtained with the highest coverage. Although 635 genes on average were detected across all cell profiled in Experiment 1, an average of 876 genes from the top 396 cells were detected (FIG. 6B). Hence, the 204 cells that we discard from subsequent analysis have an average of ~170 genes detected per cell. Similarly, for Experiment 2, an average of 1,030 genes from the top 247 single cell profiles were detected, but ~530 genes on average across all cells.

To assess the similarity of our single cell expression profiles to conventional, population-level RNA-Seq, the Pearson correlation between bulk RNA-Seq and single-cell medians constructed from different numbers of individual cells after normalizing by the total number of molecules detected in each cell were calculated (FIG. 7A and FIG. 7B). An analysis on single cell profiles originating from the U87-exclusive and MCF10a-exclusive lanes in Experiment 1 was conducted, randomly sampling the complete sets of profiles ten times without replacement for each point in the curves shown in FIG. 7A and FIG. 7B. This analysis shows that the single cell medians constructed from U87 single cell profiles correlate better with the bulk U87 RNA-Seq profile than with the bulk MCF10a RNA-Seq profile (FIG. 7A), and vice-versa (FIG. 7B). It also shows that the single cell median correlations saturate around r=0.55-0.60 depending on the cell type. As a point of comparison, an analysis for CEL-Seq and DR-Seq gave population-level Pearson correlations of 0.71 and 0.69, respectively. See, for example, Dey S S, Kester L, Spanjaard B, Bienko M, van Oudenaarden A: Integrated genome and transcriptome sequencing of the same cell. *Nat Biotechnol* 2015, 33(3):285-289, which is herein incorporated by reference in its entirety.

To further demonstrate the robustness of our data set, classifier for U87 and MCF10a cells in Experiment 1 were built. Single cell profiles from lanes that contained either exclusively U87 cells of MCF10a cells were used to identify 189 differentially expressed genes (p<0.05, Wilcoxin rank-sum test). FIG. 7C shows the log-ratio of the coefficients of variation (CVs) for each of these two genes sets between the mixed lane profiles and the profiles from the respective pure lanes. The log-ratio of CVs is greater than zero (CV ratio greater than one) for 92% of U87-specific genes and 85% of MCF10a-specific genes.

FIG. 8A shows a pathway analysis of gene ontologies enriched across >11,600 genes that were both detected across our 396 single cell profiles and available in the iPAGE database and ranked based on differential expression in Experiment 1. See, for example, Goodarzi H, Elemento O, Tavazoie S: Revealing global regulatory perturbations across human cancers. *Mol Cell* 2009, 36(5):900-911, which is herein incorporated by reference in its entirety. A matrix of Spearman correlation coefficients across our 396 profiles based on rank-ordering the 189 differentially expressed genes in each cell was then generated. The data was clus-tered spatially using the t-stochastic neighborhood embed-ding (t-SNE) algorithm, described for example in Van der Maaten L, Hinton G: Visualizing data using t-SNE. *Journal of Machine Learning Research* 2008, 9(2579-2605):85, a clustering algorithm applied to high-dimensional single cell analysis data (FIG. 8B and FIG. 8C). This t-SNE result contains two closely associated clusters of individual cells. To understand the origin of these two clusters, the t-SNE clustering with two different color-schemes are displayed. In FIG. 8B, it is shown how single cell profiles from the various lanes of a device described herein are distributed. One of the two clusters contains all of the cells from the MCF10a-exclusive lane, while the other contains nearly all of the cells from the U87 lane with a few exceptions. Single cell profiles from the mixed lanes are distributed throughout the two clusters. While the single cell profiles from mixed lanes are distributed uniformly throughout the MFC10a cluster, there is some separation between a subset of mixed lane profiles and the U87-exclusive lane profiles in the U87 cluster. In FIG. 8C, the same clustering result with a different color scheme that indicates the relative rank ordering of the U87 vs. MCF10a gene sets in each profile is described. This metric associates the cells in each of the two clusters with the expected cell type-specific expression pattern.

In an aspect, the microfluidic platforms described throughout are compatible with transcriptome-wide analysis of individual cells by RNA-Seq. In an another aspect, either could be combined with a sequence-based barcoding scheme to generate a pooled cDNA library from hundreds or thousands of individual cells. For example, in the bead capture device, barcoding is not strictly necessary because physical means could be used to extract the beads from the microwells for downstream processing with conventional labware. Alternatively, fluorescently labeled oligonucleotide probes could be used to image captured RNA molecules similar to RNA-FISH. Probes could be introduced sequentially, imaged, and removed in cycles or combined with previously reported multiplexing schemes. Similarly, sequential rounds of qRT-PCR in sealed microwells could allow targeted detection of specific genes or mutations in captured RNA.

Kits

In another aspect, the disclosure provides for a kit comprising, consisting essentially of, or consisting of any of probes, beads, and regents disclosed herein. In an aspect, the kit includes any of the combination of probes, beads, and regents disclosed herein in FIGS. 1-13. In another aspect, the kit provides for probes, beads, and regents applied in a manner that is consistent with the methodology of the examples and figures. In another aspect, the kit provides instructions or guidance regarding the use of the compositions, probes, devices, systems or methods described herein.

In an aspect, the kit includes instructions describing the methodology described herein.

The following examples serve to illustrate certain aspects of the disclosure and are not intended to limit the disclosure.

EXAMPLES

The invention is illustrated herein by the experiments described by the following examples, which should not be construed as limiting. The contents of all references, pending patent applications and published patents, cited throughout this application are hereby expressly incorporated by reference. Those skilled in the art will understand that this invention may be embodied in many different forms and should not be construed as limited to the embodiments set forth herein. Rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

Example 1

Generation of Optically Barcoded mRNA Capture Beads for Optical Demultiplexing by Multi-Color Fluorescence Imaging for Single Cell RNA-Seq N-succinimide-coated Sepharose beads with a mean diameter of ~30 μm were obtained from GE Healthcare in isopropanol. The beads were washed three times with water by centrifugation and split into 125 different tubes. The beads were then re-suspended in a reaction mixture with a final concentration of 100 mM sodium borate (pH 8.5) along with three differently-labeled streptavidin proteins (streptavidin-AlexaFluor 488, streptavidin-AlexaFluor 546, and Streptavidin-AlexaFluor 647 from Life Technologies). For each of the 125 reaction mixtures, the three proteins were added at one of 5 concentrations such that each of the 125 reaction mixtures had one of $5^3=125$ unique combinations of labels and label intensities. The reaction was incubated at room temperature for one hour on a rotisserie to allow the labeled streptavidins to covalently react with the beads, form amide bonds. The beads were then washed five times in 50 mM Tris-HCl pH 8, 50 mM NaCl, and 0.1% Tween-20 before using to completely quench any remaining reactive groups on the beads. Each of the 125 uniquely labeled sets of beads were then incubated with a uniquely barcoded, 5'-biotinylated oligonucleotide. The oligonucleotides had a universal adapter sequence on the 5'-end to facilitate amplification, a barcode sequence, and oligo(dT) on the 3'-end to facilitate mRNA capture. The oligonucleotides became bound to the beads through the biotin-streptavidin interaction, resulting in beads that could be identified by fluorescence microscopy based on their unique configuration of fluorescent labels to harbor a specific nucleic acid barcode sequence.

Generation of Optically Barcoded mRNA Capture Beads for Optical Demultiplexing by Sequential Fluorescence Hybridization for Single Cell RNA-Seq 2.4 million beads aminated polystyrene beads (Custom Primer Support 200 Amino, GE) were reacted with an 8% solution of glutaraldehyde in Cyanoborohydride Coupling Buffer (Sigma) for six hours a room temperature. After washing the beads in phosphate buffered saline (PBS), the beads were divided evenly into each of 32 tubes. To each tube, 62.5 pmol of a unique 5'-aminated oligonucleotide were added containing an adapter sequence, a unique capture barcode sequence, and a linker sequence. In addition, zero or more 5'-aminated oligonucleotides were added from a set of five, each of which contains a unique optical barcode sequence and a linker sequence. The constellation of oligonucleotides on the bead surface forms a binary code. For example, if there are five oligonucleotides in a set, and the first, third, and fourth oligonucleotides are present on the bead, then the code could be in an aspect, 10110. However, there will also be a bead in the set with the code 00000, where none of the oligonucleotides are present. This also provides a signal, a bead that does not fluoresce when exposed to any of the probes 0.2.5 pmol of each optical barcode oligonucleotide was further added. Each capture barcode sequence is associated with a unique set of optical barcode sequences. In this embodiment, there are 32 capture barcode sequences and $2^5=32$ possible combinations of optical barcode configurations added in the first round of synthesis. The 5'-aminated oligonucleotides were reacted with the aldehyde-conjugated beads in Cyanoborohydride Coupling buffer for 12 hours at room temperature. The reaction was then quenched by the reaction by adding 1 M Tris-HCl to each well. The beads were then washed in PBS.

In a second barcode synthesis, the 32 reactions from the first round were pooled and then re-distributed into each of 128 tubes. To each tube, 150 pmol of a unique oligonucleotide was added containing a linker sequence complementary to that in the capture barcode oligonucleotides already attached to the beads, a second capture barcode sequence, a random sequence (for unique molecular identification), and a poly(A) sequence. In addition, zero or more oligonucleotides from a set of seven were added, each of which contains a unique optical barcode sequence and a linker sequence complementary to that in the optical barcode oligonucleotides already attached to the beads. 20 pmol of each optical barcode oligonucleotide. Each capture barcode sequence is associated with a unique set of optical barcode sequences. There are 128 capture barcode sequences and $2^7=128$ possible combinations of optical barcode configurations added in the second round of synthesis. In combination with the first round of synthesis, the second round of synthesis results in a set of $32\times128=4,096$ uniquely barcoded beads with both unique capture and optical barcodes attached. The second round oligonucleotides was hybridized to the oligonucleotides attached in the first round in Buffer 2 (New England BioLabs) with 1% tween-20 (Sigma) at 50 C for 20 minutes and at room temperature for 12 hours. The beads were then washed and then copied the second round oligonucleotides onto the 3'-end of the first round oligonucleotides by primer extension with Klenow Large Fragment DNA Polymerase (New England BioLabs) at room temperature for 2 hours. The primer extension reaction was quenched with EDTA followed by sodium hydroxide. The beads from all 128 reactions were then pooled and washed them extensively in sodium hydroxide and Wash Buffer (10 mM Tris pH 8, 1 mM EDTA, 0.01% tween-20).

Fabrication of a PDMS Microwell Array Device

Microfabricated arrays of cylindrical pillars in photoresist on a silicon wafer were obtained from FlowJEM. The pillars were 50 microns in diameter and 50 microns tall. A second wafer contained a relief pattern of a flow channel. A 1:10 mixture of liquid polydimethylsiloxane (PDMS) base and curing agent (Sylgard 184, Dow-Corning) was poured on each wafer. A glass microscope slide was pressed onto the uncured liquid PDMS that had been poured on the wafer containing cylindrical pillars, forming a thin layer of PDMS between the wafer and the glass slide. Both wafers with liquid PDMS were then placed in an oven to cure at 90° C. overnight. The cured, solidified PDMS were then peeled from both wafers resulting in a thin microwell array on the glass slide and a PDMS flow channel. After using a punch to insert inlet and outlet holes on either end of the flow channel, air plasma was used to bond the flow channel over the microwell array. The resulting microwell array flow cell device was then used for single cell RNA-Seq and optical demultiplexing.

Single Cell RNA-Seq Library Generation in a Microwell Array Device Using In Vitro Transcription Prior to the experiment, the device was flushed with 0.1% Tween-20 and incubated for several hours to hydrate the microwells, which were subsequently washed with PBS. Cell suspensions were counted using the Countess automated cell counter (Life Technologies). A suspension of cells in PBS mixed with Calcein AM (live stain) was flowed into the device and incubated for five minutes. Cells were deposited in the microwells by gravity. After thoroughly removing any excess cells with PBS, a suspension of barcoded capture beads that had been pre-counted by microscopy was introduced in PBS and allowed to load under gravity for five minutes. Excess beads were thoroughly removed with PBS and the flow cell was incubated on ice. A lysis buffer containing 0.08% Triton X-100 supplemented with SUPERaseIN (Life Technologies) was flowed under ice-cold conditions immediately followed by fluorinert oil (Sigma) to seal the device. After two cycles of freeze-thaw at ~80 C to enhance cell lysis, the device was incubated at room temperature for 60 minutes for mRNA capture. After one hour of incubation for mRNA capture, the device was unsealed by rapid removal of the fluorinert oil with 20 mM Tris-HCl pH 8 containing 1% Triton X-100 and SUPERaseIN followed by thorough washing of the device with 20 mM Tris-HCl pH 8, 50 mM NaCl, and 0.1% Tween-20.

The mRNA captured on the beads was reverse transcribed using ProtoScript II Reverse Transcriptase (New England BioLabs) for two hours at 42 C in 1× ProtoScript Reverse Transcriptase Buffer supplemented with 10 mM DTT, 0.5 mM dNTPs, 0.1% Tween-20, and SUPERaseIN. The reaction mixture was then removed with 20 mM Tris-HCl pH 8, 50 mM NaCl, and 0.1% Tween-20. Second strand synthesis was carried out using the MessageAmp II aRNA amplification kit (Ambion) according to the manufacturer's instructions. This involves a reaction mixture with DNA polymerase and RNaseH that is incubated for two hours at 16 C. After removing the second strand reaction mixture with 20 mM Tris-HCl pH 8, 50 mM NaCl, and 0.1% Tween-20, in vitro transcription (IVT) was carried out using reagents in the MessageAmp II aRNA amplification kit (Ambion) including T7 RNA polymerase according to the manufacturer's instructions for 13 hours at 37 C. The reaction linearly amplified the double-stranded cDNA libraries on the beads, eluting pools of barcoded aRNA into the flow channel which was subsequently removed using a pipette and purified using an RNA Clean & Concentrator Column (Zymo). aRNA was then reverse transcribed using uniquely barcoded random hexamer primers using PrimeScript Reverse Transcriptase (Clontech) supplemented with 0.5 mM dNTPs, 10 mM DTT, 1× PrimeScript Buffer, and 0.1 U/uL SUPERaseIN. The reaction proceeded for 10 minutes at 25 C and two hours at 42 C. The RNA-cDNA hybrid product was purified twice using 0.65× Ampure XP beads (Beckman). The resulting cDNA libraries were then enriched by PCR using Phusion High Fidelity DNA polymerase (New England BioLabs) using the Illumina RP1 and RPI primers. The resulting PCR product was then purified on a 1.5% agarose gel, extracted using a Gel Extraction Kit (Qiagen), purified using 0.65× Ampure XP beads (Beckman), and sequenced on a NextSeq 500 sequencer (Illumina).

Single Cell RNA-Seq Library Generation in a Microwell Array Device Using Template-Switching Cells and mRNA capture beads were loaded into the microwell array device as described above. The device was then placed on a computerized temperature and fluidic control system for automated single cell library production. The system consists of a manually controlled pressurization system, software, an electronic six-port rotary selector valve (Rheodyne), and a thermoelectric heater-cooler module (TE Technology). After cooling the system to 4 C, a lysis solution comprised of TCL Buffer (Qiagen) and 1% 2-mercaptoethanol was introduced to the device, which was rapidly and automatically sealed with fluorinert (Sigma). After removing the oil and unsealing the microwells, a reverse transcription reaction mixture comprised of 1× Maxima RT Buffer, 1 mM dNTPs, 1 U/uL SUPERaseIN, 2.5 uM template-switching oligonucleotide, 0.1% Tween-20, and 10 U/uL Maxima H-Reverse Transcriptase (ThermoFisher) was introduced and incubated for 30 minutes at room temperature followed by 90 minutes at 42 C.

After removing the reverse transcription reaction mixture, the beads were removed from the microwells by sonication, concentrated by centrifugation and incubated for 30 minutes at 37 C with Exonuclease I in 1× Exonuclease I Buffer (New England BioLabs). The beads were then washed in 10 mM Tris-HCl pH 8, 1 mM EDTA, and 0.5% sodium dodecyl sulfate (SDS) followed by 10 mM Tris-HCl pH 8, 1 mM EDTA, and 0.01% Tween-20. The beads were then resuspended in a PCR reaction mixture containing 1× HiFi Hot Start Ready Mix (Kappa) and 1 uM PCR primer and thermocycled to amplify a full-length, double-stranded, pooled cDNA library. The PCR product was purified with 0.6× Ampure XP beads (Beckman). The library was then fragmented and a sequencing adapter introduced using the Nextera XT library preparation kit (Illumina) according to the manufacturer's instructions. Finally, the sequencing library was enriched by PCR using a reverse PCR primer from the Nextera XT kit and a custom forward PCR primer along with amplification reagents from the Nextera XT kit used according to the manufacturer's instructions. The resulting PCR product was purified with 0.6× Ampure XP beads (Beckman) and sequenced on a NextSeq 500 sequencer (Illumina).

Optical Demultiplexing of Barcoded mRNA Capture Beads

Following cDNA synthesis on the surface of optically barcoded capture beads, the microwell array device was transferred to an epifluorescence microscope system. The microscope system contains an inverted microscope frame (Ti-U, Nikon), an electron-multiplied charge coupled device (EM-CCD) camera (iXon, Andor), a 20×0.75 NA air objective lens (Nikon), a three-axis motorized stage (ASI), a 140 mW 637 nm optically pumped semiconductor laser (OBIS, Coherent), and custom optics for coupling the laser beam into the microscope. The custom optical path includes an engineered diffusor (Thorlabs) and electronic phase scrambling device for flattening the illumination field. An automated, computer-controlled fluidics system is attached the microscope system and contains two, ten-channel rotary selector valves (Rheodyne). A single computer program controls the fluidics system, laser shutter, camera, and microscope stage. Each of twelve, Cy5-labeled optical barcode probes was loaded into the channels of the fluidics system. The optical barcode probes were each complementary to one of the optical barcode oligonucleotides attached the beads as described above. In addition, a wash buffer (20 mM Tris-HCl pH 8, 50 mM NaCl, and 0.1% Tween-20) and a denaturing solution (100 mM NaOH) were loaded into independent channels of the fluidics system. The first of twelve optical barcode probes was flowed into the flow cell, incubated at room temperature for ten minutes, and washed out with wash buffer. After washing, the microscope automatically scanned and imaged the entire microwell array and identifies the beads in each microwell that are fluorescently labeled with the first optical barcode probe by hybridization, indicating the presence of the first optical barcode sequence. The denaturing solution was then introduced to the flow cell which causes the first optical barcode probe to dissociate from the beads and exit the flow cell. After washing with wash buffer, the process was repeated for all of the remaining optical barcode probes. At conclusion, the configuration of optical barcode sequences attached to each bead can be inferred from the series of twelve fluorescence images. Because each unique configuration of optical barcode sequences corresponds to a specific capture barcode sequence associated with the cDNA that is also attached to each bead, the capture barcode sequence for each individual cell can be identified (see, for example, FIG. 1A and FIG. 1B). This allows a direct association between imaging information acquired from the cells, the capture barcode associated with the cDNA of the at cell that is read out on the sequencer, and therefore the transcriptome of that cell all through identification of the corresponding optical barcode.

Example 2

Fabrication PDMS Microwell Arrays for Single Cell RNA Printing

Silicon wafer masters (~4 in) with cylindrical pillars (diameter 50 micron; height 30 micron) for photolithography were obtained from Stanford Microfluidics Foundry and were subsequently exposed to 1H,1H,2H,2H-perfluorooctyltrichlorosilane (Alfa Aesar) vapor under vacuum for ~30 minutes to avoid curing of the PDMS on the wafer. PDMS (Sylgard 184, Dow Corning) was thoroughly mixed 10:1 (base:curing agent) and degassed under house vacuum for 2 hours. ~15 g of degassed PDMS was poured onto the 4 in silicon wafer master and allowed to cure overnight at ~90°

C. This slab with microwells was then gently peeled off from the master and used to construct PDMS microreactor flow cells.

Surface Chemistry on Glass Coverslip

VistaVision Microscope cover glass (22×50×0.16 mm) was plasma sterilized (Harrick Plasma) for ~5 mins, and immediately immersed in 10% acetic acid (pH 3.5) ethanol solution containing 0.5% trimethoxysilanealdehyde (United Chemical Technologies), and incubated for 15 mins. The cover glass was then washed with ethanol, air-dried and heat cured at 90° C. for 10 mins. A 2.5 μM solution of 5'-aminated-LNA-oligo(dT) (Exiqon) in cyanoborohyride coupling buffer (Sigma) supplemented with 1M NaCl was added on the aldehyde surface of the cover glass. The cover glass was incubated for 3 hours at room temperature inside a humid chamber, and then washed with DI water. The aldehyde surface was then incubated in 10% ethanolamine in cyanoborohydride coupling buffer for 30 mins to quench the unreacted aldehydes.

Construction of the Flowcell

A rectangular slab (3.5×1.5×0.1 cm) of PDMS containing the microwell array in the center was cut and a double-sided adhesive tape (~120 micron thickness, Grace BioLabs) was adhered to the flat side of the PDMS slab that contained the microwells. The tape was cut in an elongated hexagonal shape, which formed the microchannel in the flowcell. The other side of the tape was pasted on the LNA coated cover glass to build the microfluidic device. Two holes were punched at the two end of the microchannel with a biopsy punch, which acted as the inlet and outlet of the device and tubing were attached to allow liquid flow. The periphery of the PDMS slab was sealed on to the cover glass using epoxy glue.

Experimental Procedure for Single Cell mRNA Printing on Glass

A suspension of U87 cells in PBS was flowed in to the device and loaded into the microwells by gravity (kept upside down) for 5 mins at room temperature. After washing with PBS buffer supplemented with SUPERaseIN (Ambion), the microwells were sealed using an automated mechanical device by placing the flow cell upside down on a screw mounted on a motorized z-stage (ASI) so that the top PDMS slab containing the microwells was pressed against the glass bottom. After sealing the wells mechanically, the seal was retained by hermetic sealing to trap the single cell lysate within a single microwell. The cells were lysed by freeze-thaw. Once the cells lysed, the mRNAs were captured on the LNA surface by hybridization of the 3'-polyA tail of the mRNA to the LNA-oligo(dT) during a 60 minute incubation. The microwells were then unsealed and the flow cell was immediately and vigorously washed with the Wash Buffer (20 mM Tris pH 8.0, 50 mM NaCl, 0.1% Tween-20), supplemented with SUPERaseIN (FIG. 2A). The flowcell was then incubated with TURBO DNase (Ambion) in TURBO DNase buffer, supplemented with 0.1% Tween-20 and SUPERaseIN for 30 mins at 37° C. to digest any residual genomic DNA. The mRNA captured on the LNA surface was reverse transcribed using M-MuLV Reverse Transcriptase (New England Biolabs) for 2 hours at 42° C. in 1× M-MuLV Reverse Transcriptase buffer, supplemented with 10 mM DTT, 5 mM dNTPs, 0.1% Tween-20 and SUPERaseIN. After reverse transcription the double stranded RNA-cDNA hybrids were stained with 10 nM SYTOX Orange dye (Invitrogen), an intercalator that is selective for double-stranded DNA, and incubated for 5 mins prior to imaging.

The epifluorescence imaging system was constructed on an inverted Nikon Eclipse Ti-U microscope with 20×, 0.75 NA air objective (Plan Apo X, Nikon). SYTOX Orange was excited using a 532 nm diode-pumped solid state laser (Dragon Lasers), and the fluorescence was collected and imaged onto an electron multiplying charge coupled device (EMCCD) camera (iXON3, Andor Technologies). The images were acquired with 0.5 s exposure time (controlled by external shutter) at 1 MHz digitization (with no EM gain). Automated scanning of the surface (motorized X-Y stage, ASI), image acquisition, and illumination were controlled with custom software written in C/C++. The images were analyzed using ImageJ software.

Microfluidic Device for Single Cell RNA-Seq

For the single cell RNA-Seq experiment a monolithic PDMS was designated based multi-channel device, by fabricating each channel with a microwell array. Two key soft lithography techniques were used to fabricate this device. First, instead of using silicon wafer master directly for fabricating the microwell array as done in the case of RNA printing device, we generated a secondary master made out of PDMS. This was done because the aspect ratio of the micropillars results in a relatively fragile silicon master. It was found that the PDMS master to be more durable. Second, instead of using a double-sided adhesive tape for the device assembly, the bottom and the top of the device were bonded together by partial curing. This provided us with more durable and reliable partitions between the individual channels of our device than could be generated using tape. For the multi-lane microfluidic device, two different silicon wafer masters were fabricated, one for the top and other for the bottom containing the array of microwells. Masters for soft lithography were generated from 4-inch silicon test wafers (University Wafer) coated with SU-8 2005 (MicroChem) photoresist. The wafer master for the bottom of the device contained five arrays of cylindrical pillars (diameter 50 micron; height 50 micron). The wafer was then fluorosilanized as described above. To avoid repeated use of the silicon wafer, we fabricated secondary masters in PDMS as follows. 40 g of degassed PDMS 10:1 (base:curing agent) was poured and cured on the wafer, and then peeled off and cut into a rectangular slab. The surface containing an array of microwells was oxidized in plasma chamber (Harrick Plasma) for ~2 mins and immediately fluorosilanized. Using this microwell-containing slab as a master, ~10 g of degassed PDMS was cured on it and peeled off. This new PDMS slab containing array of pillars is an exact replica of the silicon wafer, and is fluorosilanized and served as a secondary master for soft lithography for microfabrication of the bottom part of the microfluidic flowcell device. ~2 g of degassed PDMS 10:1 (base:curing agent) was poured on a plasma cleaned glass slide and the secondary master with pillar array was placed gently with pillars immersed into the liquid PDMS. The slide, PDMS and master (on top) was degassed for ~5 mins and then cured hard at 90° C. for 2 hours. After curing, the master is peeled off and a thin layer of PDMS is bonded to the glass slide with 5 lane arrays of microwells.

A second silicon wafer master was constructed containing five longitudinal ridges (with a height of 100 microns) with rounded ends on which ~30 g of degassed PDMS 15:1 (base:curing agent) was poured and allowed to cure partially at 60° C. for 90 mins. The partially cured PDMS was cut into a slab, holes were punched at either end of each channel, and the slab was placed gently on the top of the glass slide containing the microwell array in such a way that the longitudinal grooves were aligned over each of the five microwell arrays. The slide assembly was then incubated at 90° C. overnight to form a single monolithic PDMS structure as shown in FIG. 5A.

Synthesis of Uniquely Barcoded Beads for mRNA Capture

N-succinimide-coated Sepharose beads with a mean diameter of ~30 μm were obtained from GE Healthcare in isopropanol. The beads were washed three times with water by centrifugation and re-suspended in a reaction mixture with a final concentration of 100 mM sodium borate (pH 8.5) and ~0.8 mg/mL streptavidin (streptavidin from New England BioLabs was spiked with ~2% AlexaFluor 647-labeled streptavidin from Life Technologies). The reaction was incubated at room temperature for one hour on a rotisserie to allow the streptavidin to covalently attach to the beads. The beads were then washed five times in Wash Buffer and incubated in 1 Wash Buffer for 30 minutes before using to completely quench any remaining reactive groups on the beads.

A dual-biotinylated oligonucleotide containing both the T7 promoter sequence and a partial Illumina adapter sequence (Table 1) were annealed to each of 96 oligonucleotides (Table 2) that are complementary to the partial Illumina adapter sequence on the 3'-end and contain a unique barcode and universal anchor sequence on the 5'-end (FIGS. 3A and 3B). Table 1 describes a list of oligonucleotides used for barcoding and library preparation in additional to list of cell-identifying barcodes in Table 2 for Experiment 1.

TABLE 1

| Oligonucleotide Name | Oligonucleotide Sequence |
|---|---|
| Bead Capture Oligo (5'-dual biotinylated) | AGGTAAGGTAATACGACTCACTATAGGGGTTCAGAGTTCTACAGTCCG ACGATC (SEQ ID NO: 1) |
| RT1 (Reverse Transcription Primer for Lane 1) | GCCTTGGCACCCGAGAATTCCANNNNNNNNNCGTGATNNNNNNN (SEQ ID NO: 2) |
| RT2 (Reverse Transcription Primer for Lane 2) | GCCTTGGCACCCGAGAATTCCANNNNNNNNNACATCGNNNNNNN (SEQ ID NO: 3) |
| RT3 (Reverse Transcription Primer for Lane 3) | GCCTTGGCACCCGAGAATTCCANNNNNNNNNGCCTAANNNNNNN (SEQ ID NO: 4) |
| RT4 (Reverse Transcription Primer for Lane 4) | GCCTTGGCACCCGAGAATTCCANNNNNNNNNTGGTCANNNNNNN (SEQ ID NO: 5) |
| RT5 (Reverse Transcription Primer for Lane 5) | GCCTTGGCACCCGAGAATTCCANNNNNNNNNCACTGTNNNNNNN (SEQ ID NO: 6) |

TABLE 1-continued

| Oligonucleotide Name | Oligonucleotide Sequence |
|---|---|
| RP1 (PCR Primer 1) | AATGATACGGCGACCACCGAGATCTACACGTTCAGAGTTCTACAGTCC<br>GA (SEQ ID NO: 7) |
| RPI1 (PCR Primer 2) | CAAGCAGAAGACGGCATACGAGATCGTGATGTGACTGGAGTTCCTTGG<br>CACCCGAGAATTCCA (SEQ ID NO: 8) |

TABLE 2

| Oligonucleotide Name | Oligonucleotide Sequence |
|---|---|
| FBC_Oligo1 | CAGGTCAACCAGAGAGATCGTCGGACTGTAGAACTCTGAAC<br>(SEQ ID NO: 9) |
| FBC_Oligo2 | CAGGTCAAAGTACGCGATCGTCGGACTGTAGAACTCTGAAC<br>(SEQ ID NO: 10) |
| FBC_Oligo3 | CAGGTCGTTTGGCATGATCGTCGGACTGTAGAACTCTGAAC<br>(SEQ ID NO: 11) |
| FBC_Oligo4 | CAGGTCAAGTGAGGTGATCGTCGGACTGTAGAACTCTGAAC<br>(SEQ ID NO: 12) |
| FBC_Oligo5 | CAGGTCACGTTAGCTGATCGTCGGACTGTAGAACTCTGAAC<br>(SEQ ID NO: 13) |
| FBC_Oligo6 | CAGGTCGTGCTAGAGGATCGTCGGACTGTAGAACTCTGAAC<br>(SEQ ID NO: 14) |
| FBC_Oligo7 | CAGGTCGTCCTGTGTGATCGTCGGACTGTAGAACTCTGAAC<br>(SEQ ID NO: 15) |
| FBC_Oligo8 | CAGGTCTCTACGGCAGATCGTCGGACTGTAGAACTCTGAAC<br>(SEQ ID NO: 16) |
| FBC_Oligo9 | CAGGTCACAGGGCTTGATCGTCGGACTGTAGAACTCTGAAC<br>(SEQ ID NO: 17) |
| FBC_Oligo10 | CAGGTCGTGCGTTATGATCGTCGGACTGTAGAACTCTGAAC<br>(SEQ ID NO: 18) |
| FBC_Oligo11 | CAGGTCGGGTAAGTAGATCGTCGGACTGTAGAACTCTGAAC<br>(SEQ ID NO: 19) |
| FBC_Oligo12 | CAGGTCTCCCTTAGGGATCGTCGGACTGTAGAACTCTGAAC<br>(SEQ ID NO: 20) |
| FBC_Oligo13 | CAGGTCCAAGTTGGTGATCGTCGGACTGTAGAACTCTGAAC<br>(SEQ ID NO: 21) |
| FBC_Oligo14 | CAGGTCTTCTCACTCGATCGTCGGACTGTAGAACTCTGAAC<br>(SEQ ID NO: 22) |
| FBC_Oligo15 | CAGGTCTCCCACTCTGATCGTCGGACTGTAGAACTCTGAAC<br>(SEQ ID NO: 23) |
| FBC_Oligo16 | CAGGTCCGGTATACCGATCGTCGGACTGTAGAACTCTGAAC<br>(SEQ ID NO: 24) |
| FBC_Oligo17 | CAGGTCAGGCATGTGGATCGTCGGACTGTAGAACTCTGAAC<br>(SEQ ID NO: 25) |
| FBC_Oligo18 | CAGGTCCCCAGATTGGATCGTCGGACTGTAGAACTCTGAAC<br>(SEQ ID NO: 26) |
| FBC_Oligo19 | CAGGTCTTCCCTTGAGATCGTCGGACTGTAGAACTCTGAAC<br>(SEQ ID NO: 27) |
| FBC_Oligo20 | CAGGTCGTTGTACGAGATCGTCGGACTGTAGAACTCTGAAC<br>(SEQ ID NO: 28) |
| FBC_Oligo21 | CAGGTCTGCTTGCAGGATCGTCGGACTGTAGAACTCTGAAC<br>(SEQ ID NO: 29) |
| FBC_Oligo22 | CAGGTCGGCCTCATTGATCGTCGGACTGTAGAACTCTGAAC<br>(SEQ ID NO: 30) |

TABLE 2-continued

| Oligonucleotide Name | Oligonucleotide Sequence |
| --- | --- |
| FBC_Oligo23 | CAGGTCAACAGCCTAGATCGTCGGACTGTAGAACTCTGAAC<br>(SEQ ID NO: 31) |
| FBC_Oligo24 | CAGGTCGATGCAATGGATCGTCGGACTGTAGAACTCTGAAC<br>(SEQ ID NO: 32) |
| FBC_Oligo25 | CAGGTCGAAGGAACGGATCGTCGGACTGTAGAACTCTGAAC<br>(SEQ ID NO: 33) |
| FBC_Oligo26 | CAGGTCCAGCCACTTGATCGTCGGACTGTAGAACTCTGAAC<br>(SEQ ID NO: 34) |
| FBC_Oligo27 | CAGGTCCTCTGCTTCGATCGTCGGACTGTAGAACTCTGAAC<br>(SEQ ID NO: 35) |
| FBC_Oligo28 | CAGGTCGGCTTATGAGATCGTCGGACTGTAGAACTCTGAAC<br>(SEQ ID NO: 36) |
| FBC_Oligo29 | CAGGTCCTAGTCCTCGATCGTCGGACTGTAGAACTCTGAAC<br>(SEQ ID NO: 37) |
| FBC_Oligo30 | CAGGTCCTAGAGGAGGATCGTCGGACTGTAGAACTCTGAAC<br>(SEQ ID NO: 38) |
| FBC_Oligo31 | CAGGTCAGCTTTACCGATCGTCGGACTGTAGAACTCTGAAC<br>(SEQ ID NO: 39) |
| FBC_Oligo32 | CAGGTCGTCCATGAAGATCGTCGGACTGTAGAACTCTGAAC<br>(SEQ ID NO: 40) |
| FBC_Oligo33 | CAGGTCCTCGAACCTGATCGTCGGACTGTAGAACTCTGAAC<br>(SEQ ID NO: 41) |
| FBC_Oligo34 | CAGGTCCATTGTACGGATCGTCGGACTGTAGAACTCTGAAC<br>(SEQ ID NO: 42) |
| FBC_Oligo35 | CAGGTCTTGAACGCTGATCGTCGGACTGTAGAACTCTGAAC<br>(SEQ ID NO: 43) |
| FBC_Oligo36 | CAGGTCTACGTCATGGATCGTCGGACTGTAGAACTCTGAAC<br>(SEQ ID NO: 44) |
| FBC_Oligo37 | CAGGTCAAGCCGTTAGATCGTCGGACTGTAGAACTCTGAAC<br>(SEQ ID NO: 45) |
| FBC_Oligo38 | CAGGTCCGGACGTATGATCGTCGGACTGTAGAACTCTGAAC<br>(SEQ ID NO: 46) |
| FBC_Oligo39 | CAGGTCTCGTTACCGGATCGTCGGACTGTAGAACTCTGAAC<br>(SEQ ID NO: 47) |
| FBC_Oligo40 | CAGGTCATCCCCCATGATCGTCGGACTGTAGAACTCTGAAC<br>(SEQ ID NO: 48) |
| FBC_Oligo41 | CAGGTCCAGACGATTGATCGTCGGACTGTAGAACTCTGAAC<br>(SEQ ID NO: 49) |
| FBC_Oligo42 | CAGGTCATCGATCCCGATCGTCGGACTGTAGAACTCTGAAC<br>(SEQ ID NO: 50) |
| FBC_Oligo43 | CAGGTCCCTGAGGATGATCGTCGGACTGTAGAACTCTGAAC<br>(SEQ ID NO: 51) |
| FBC_Oligo44 | CAGGTCAGCTCTTTGGATCGTCGGACTGTAGAACTCTGAAC<br>(SEQ ID NO: 52) |
| FBC_Oligo45 | CAGGTCGGAATACGGGATCGTCGGACTGTAGAACTCTGAAC<br>(SEQ ID NO: 53) |
| FBC_Oligo46 | CAGGTCCTATCCTGGGATCGTCGGACTGTAGAACTCTGAAC<br>(SEQ ID NO: 54) |
| FBC_Oligo47 | CAGGTCGGTTGTAGTGATCGTCGGACTGTAGAACTCTGAAC<br>(SEQ ID NO: 55) |
| FBC_Oligo48 | CAGGTCGAACGTAGCGATCGTCGGACTGTAGAACTCTGAAC<br>(SEQ ID NO: 56) |

TABLE 2-continued

| Oligonucleotide Name | Oligonucleotide Sequence |
|---|---|
| FBC_Oligo49 | CAGGTCGTCTATCGGATCGTCGGACTGTAGAACTCTGAAC<br>(SEQ ID NO: 57) |
| FBC_Oligo50 | CAGGTCTACGAGTGGATCGTCGGACTGTAGAACTCTGAAC<br>(SEQ ID NO: 58) |
| FBC_Oligo51 | CAGGTCTCATGTCGGATCGTCGGACTGTAGAACTCTGAAC<br>(SEQ ID NO: 59) |
| FBC_Oligo52 | CAGGTCAAACACCCGATCGTCGGACTGTAGAACTCTGAAC<br>(SEQ ID NO: 60) |
| FBC_Oligo53 | CAGGTCACTAGTCCGATCGTCGGACTGTAGAACTCTGAAC<br>(SEQ ID NO: 61) |
| FBC_Oligo54 | CAGGTCCGAGGAATGATCGTCGGACTGTAGAACTCTGAAC<br>(SEQ ID NO: 62) |
| FBC_Oligo55 | CAGGTCACAATGGCGATCGTCGGACTGTAGAACTCTGAAC<br>(SEQ ID NO: 63) |
| FBC_Oligo56 | CAGGTCTAGGTCTCGATCGTCGGACTGTAGAACTCTGAAC<br>(SEQ ID NO: 64) |
| FBC_Oligo57 | CAGGTCTCTGTGAGGATCGTCGGACTGTAGAACTCTGAAC<br>(SEQ ID NO: 65) |
| FBC_Oligo58 | CAGGTCGGGATTGAGATCGTCGGACTGTAGAACTCTGAAC<br>(SEQ ID NO: 66) |
| FBC_Oligo59 | CAGGTCAACTCTGGGATCGTCGGACTGTAGAACTCTGAAC<br>(SEQ ID NO: 67) |
| FBC_Oligo60 | CAGGTCAAACGCGTGATCGTCGGACTGTAGAACTCTGAAC<br>(SEQ ID NO: 68) |
| FBC_Oligo61 | CAGGTCTCCTACGAGATCGTCGGACTGTAGAACTCTGAAC<br>(SEQ ID NO: 69) |
| FBC_Oligo62 | CAGGTCTAGCAGGTGATCGTCGGACTGTAGAACTCTGAAC<br>(SEQ ID NO: 70) |
| FBC_Oligo63 | CAGGTCCCTGCATTGATCGTCGGACTGTAGAACTCTGAAC<br>(SEQ ID NO: 71) |
| FBC_Oligo64 | CAGGTCGTGATGCAGATCGTCGGACTGTAGAACTCTGAAC<br>(SEQ ID NO: 72) |
| FBC_Oligo65 | CAGGTCCGATTCAGGATCGTCGGACTGTAGAACTCTGAAC<br>(SEQ ID NO: 73) |
| FBC_Oligo66 | CAGGTCAGGATGACGATCGTCGGACTGTAGAACTCTGAAC<br>(SEQ ID NO: 74) |
| FBC_Oligo67 | CAGGTCAGGCCATAGATCGTCGGACTGTAGAACTCTGAAC<br>(SEQ ID NO: 75) |
| FBC_Oligo68 | CAGGTCGCTTGCTTGATCGTCGGACTGTAGAACTCTGAAC<br>(SEQ ID NO: 76) |
| FBC_Oligo69 | CAGGTCTCCCAAGTGATCGTCGGACTGTAGAACTCTGAAC<br>(SEQ ID NO: 77) |
| FBC_Oligo70 | CAGGTCTCAAGGCAGATCGTCGGACTGTAGAACTCTGAAC<br>(SEQ ID NO: 78) |
| FBC_Oligo71 | CAGGTCACGAGGTAGATCGTCGGACTGTAGAACTCTGAAC<br>(SEQ ID NO: 79) |
| FBC_Oligo72 | CAGGTCGGAACGAAGATCGTCGGACTGTAGAACTCTGAAC<br>(SEQ ID NO: 80) |
| FBC_Oligo73 | CAGGTCAATCCCAGGATCGTCGGACTGTAGAACTCTGAAC<br>(SEQ ID NO: 81) |
| FBC_Oligo74 | CAGGTCCGATAAGGGATCGTCGGACTGTAGAACTCTGAAC<br>(SEQ ID NO: 82) |

TABLE 2-continued

| Oligonucleotide Name | Oligonucleotide Sequence |
|---|---|
| FBC_Oligo75 | CAGGTCTATCGCGAGATCGTCGGACTGTAGAACTCTGAAC (SEQ ID NO: 83) |
| FBC_Oligo76 | CAGGTCCGCATAACGATCGTCGGACTGTAGAACTCTGAAC (SEQ ID NO: 84) |
| FBC_Oligo77 | CAGGTCGTGCAGTTGATCGTCGGACTGTAGAACTCTGAAC (SEQ ID NO: 85) |
| FBC_Oligo78 | CAGGTCAGAACGCTGATCGTCGGACTGTAGAACTCTGAAC (SEQ ID NO: 86) |
| FBC_Oligo79 | CAGGTCTAGAGGTCGATCGTCGGACTGTAGAACTCTGAAC (SEQ ID NO: 87) |
| FBC_Oligo80 | CAGGTCCTGTGATGGATCGTCGGACTGTAGAACTCTGAAC (SEQ ID NO: 88) |
| FBC_Oligo81 | CAGGTCTAGAGCCAGATCGTCGGACTGTAGAACTCTGAAC (SEQ ID NO: 89) |
| FBC_Oligo82 | CAGGTCCTTGATGCGATCGTCGGACTGTAGAACTCTGAAC (SEQ ID NO: 90) |
| FBC_Oligo83 | CAGGTCTTCGTGTCGATCGTCGGACTGTAGAACTCTGAAC (SEQ ID NO: 91) |
| FBC_Oligo84 | CAGGTCTATCTGCGGATCGTCGGACTGTAGAACTCTGAAC (SEQ ID NO: 92) |
| FBC_Oligo85 | CAGGTCTGGTAGGAGATCGTCGGACTGTAGAACTCTGAAC (SEQ ID NO: 93) |
| FBC_Oligo86 | CAGGTCCCTAGACAGATCGTCGGACTGTAGAACTCTGAAC (SEQ ID NO: 94) |
| FBC_Oligo87 | CAGGTCAGTCAACGGATCGTCGGACTGTAGAACTCTGAAC (SEQ ID NO: 95) |
| FBC_Oligo88 | CAGGTCAAGGGTGAGATCGTCGGACTGTAGAACTCTGAAC (SEQ ID NO: 96) |
| FBC_Oligo89 | CAGGTCCTTCACACGATCGTCGGACTGTAGAACTCTGAAC (SEQ ID NO: 97) |
| FBC_Oligo90 | CAGGTCAGGTTGCTGATCGTCGGACTGTAGAACTCTGAAC (SEQ ID NO: 98) |
| FBC_Oligo91 | CAGGTCACCCGAAAGATCGTCGGACTGTAGAACTCTGAAC (SEQ ID NO: 99) |
| FBC_Oligo92 | CAGGTCGAAAAGGGGATCGTCGGACTGTAGAACTCTGAAC (SEQ ID NO: 100) |
| FBC_Oligo93 | CAGGTCACTTCCCAGATCGTCGGACTGTAGAACTCTGAAC (SEQ ID NO: 101) |
| FBC_Oligo94 | CAGGTCTGCTGCATGATCGTCGGACTGTAGAACTCTGAAC (SEQ ID NO: 102) |
| FBC_Oligo95 | CAGGTCATTCCTGGGATCGTCGGACTGTAGAACTCTGAAC (SEQ ID NO: 103) |
| FBC_Oligo96 | CAGGTCCAGAACTCGATCGTCGGACTGTAGAACTCTGAAC (SEQ ID NO: 104) |

Table 2 describes a list of oligonucleotide sequences used to generate the first set of barcoded beads (FBC) for combinatorial synthesis in Experiment 1.

The dual-biotinylated oligonucleotide was annealed at a final concentration of 2 μM in the presence of a four-fold molar excess of the barcoded oligonucleotide in a 96-well plate by stepwise cooling from 85 C to 30 C over 30 minutes. A DNA polymerase master mix was then added to each well such that the final concentration of the reaction components was 1×NEB Buffer 2 (New England BioLabs), 0.25 U/μL Klenow Fragment (exo-) (New England Bio-Labs), and 0.5 mM dNTPs. The reaction was incubated in each well at 37 C for 30 minutes before heat inactivating the polymerase at 75° C. for 20 minutes.

An equal volume of beads was then added to each reaction mixture so that the extended, dual-biotinylated oligonucleotide could conjugate to the streptavidin coated beads at a final density of ~1 billion oligonucleotide primers per bead. The conjugation reaction was incubated at room temperature overnight on a rotisserie and quenched with biotin at a final concentration of 2 mM and sodium hydroxide at a final concentration of 125 mM to melt the template strand off of the beads. The beads were then pooled and washed five times in 125 mM sodium hydroxide supplemented with 0.1 mM biotin and then washed an additional three times with Wash Buffer and 0.1 mM biotin. The beads were then re-suspended in Hybridization Buffer (20 mM Tris pH 8.0, 1 M NaCl, 0.1% Tween-20) supplemented with 0.1 mM biotin.

The pooled beads were split into ten reactions to which one of ten partially complementary oligonucleotides (Table 3) each containing a specific second barcode was added at a final concentration of 5 μM. The second barcode-containing oligonucleotides were allowed to hybridize to the beads at room temperature overnight on a rotisserie.

thermocycler and Klenow Fragment (exo-) (New England BioLabs) was added at a final concentration of 0.25 U/μL. The reaction was incubated for one hour at 16° C. with mixing every 10 minutes with a pipette followed by heat inactivation at 75° C. for 20 minutes.

The ten reaction mixtures were then quenched and the hybridized strand was denatured by addition of sodium hydroxide to a final concentration of 125 mM. The reaction mixtures were then washed five times in 125 mM sodium hydroxide with 0.1 mM biotin, pooled, and then further washed three times with Wash Buffer supplemented with 0.1 mM biotin.

Procedure for Single Cell RNA-Seq Experiment 1

Prior to the experiment, each lane of the device was flushed with 0.1% Tween-20 solution and incubated for several hours to hydrate the microwells, which were subsequently washed with 2 mL of phosphate-buffered saline (PBS). Cell suspensions were counted using Countess automated cell counter (Life Technologies). A suspension of

TABLE 3

| Oligonucleotide Name | Oligonucleotide Sequence |
|---|---|
| SBC_Oligo1 | AAAAAAAAAAAAAAAAAAAAAAAAAGGTGATACAGGTCAAAAAAAAA-GATCG TCGGACTGTAGAACTC (SEQ ID NO: 105) |
| SBC_Oligo2 | AAAAAAAAAAAAAAAAAAAAAAAATGAATGCCAGGTCAAAAAAAAA-GATCG TCGGACTGTAGAACTC (SEQ ID NO: 106) |
| SBC_Oligo3 | AAAAAAAAAAAAAAAAAAAAAAAATGCCAAACAGGTCAAAAAAAAA-GATCG TCGGACTGTAGAACTC (SEQ ID NO: 107) |
| SBC_Oligo4 | AAAAAAAAAAAAAAAAAAAAAAAACAGAAGCAGGTCAAAAAAAAA-GATCG TCGGACTGTAGAACTC (SEQ ID NO: 108) |
| SBC_Oligo5 | AAAAAAAAAAAAAAAAAAAAAAAACACTGGACAGGTCAAAAAAAAA-GATCG TCGGACTGTAGAACTC (SEQ ID NO: 109) |
| SBC_Oligo6 | AAAAAAAAAAAAAAAAAAAAAAAACGATGATCAGGTCAAAAAAAAA-GATCG TCGGACTGTAGAACTC (SEQ ID NO: 110) |
| SBC_Oligo7 | AAAAAAAAAAAAAAAAAAAAAAAAGTGTCCACAGGTCAAAAAAAAA-GATCG TCGGACTGTAGAACTC (SEQ ID NO: 111) |
| SBC_Oligo8 | AAAAAAAAAAAAAAAAAAAAAAAATCCTCTTCAGGTCAAAAAAAAA-GATCG TCGGACTGTAGAACTC (SEQ ID NO: 112) |
| SBC_Oligo9 | AAAAAAAAAAAAAAAAAAAAAAAAGTGCAGTCAGGTCAAAAAAAAA-GATCG TCGGACTGTAGAACTC (SEQ ID NO: 113) |
| SBC_Oligo10 | AAAAAAAAAAAAAAAAAAAAAAAAGGTAGACAGGTCAAAAAAAAA-GATCG TCGGACTGTAGAACTC (SEQ ID NO: 114) |

55

Table 3 describes oligonucleotide sequences used to generate the second set of barcoded beads (SBC) for combinatorial synthesis in Experiment 1.

The beads were then washed five times in Wash Buffer supplemented with 0.1 mM biotin and then re-suspended in a reaction mixture with final concentrations of 0.5 mM dNTPs, 1×NEB Buffer 2 (New England BioLabs), and 0.1 mM biotin. We included biotin in the wash and storage buffers in order to saturate any remaining streptavidin sites on the beads so that, in the even that a barcoded capture primer dissociates form a beads, it cannot re-associate with a different bead. The reactions were cooled to 16° C. on a cells in PBS mixed with Calcein AM (live stain) dye was flowed in to each lane and incubated for ~5 mins, so that the cells load in to the microwells under gravity. After thoroughly washing out the excess cells with PBS, a suspension of barcoded capture beads that had been pre-counted by microscopy was introduced in PBS and allowed to load under gravity for ~5 mins. In an aspect, ~3,000 cells to each lane of the device was introduced. It is also noted that only 25% of the lower surface of each channel contains a microwell array, and so by expanding this area, the number of cells captured without incurring increased reagent costs for on-chip library generation were significantly increased (for example, as long as the size of the barcode pool was pooled). Excess beads were washed out thoroughly with PBS and the flow cell was incubated on ice. 20 μL 0.08% TritonX-100 (Sigma) supplemented with SUPERaseIN in PBS was flowed under ice-cold conditions immediately followed by fluorinert oil (Sigma) to seal the device. After two cycles of freeze-thaw at −80° C. to enhance cell lysis, the device was incubated at room temperature for 60 mins for mRNA capture (FIG. 2A).

Two of the lanes contained pure U87 and MCF10a cells, respectively, and other lanes were loaded with a mixture of both the cell types. All lanes were imaged twice, first with blue laser ($\lambda_{ex}$=473 nm, Dragon Lasers) for imaging the cells and secondly with a red laser ($\lambda_{ex}$=637 nm, Obis, Coherent) for imaging the beads labeled with AlexaFluor 647 tagged streptavidin. We used the two-color images to determine number of bead-cell pairs in the array. After an hour of incubation for mRNA capture, all the lanes were unsealed by rapid washing of the oil with 20 mM Tris, containing 1% TritonX-100 and SUPERaseIN, followed by Wash Buffer supplemented with SUPERaseIN. After this point the microwells stay open and subsequent enzymatic steps occur simultaneously in separate lanes of the open device.

The single cell library preparation protocol is adopted from the recently reported CEL-Seq protocol with few modifications as described below. The mRNA captured on the beads was reverse transcribed using ProtoScript II Reverse Transcriptase (New England Biolabs) for 2 hours at 42° C. in 1× ProtoScript Reverse Transcriptase buffer, supplemented with 10 mM DTT, 0.5 mM dNTPs, 0.1% Tween-20 and SUPERaseIN. The reaction mixture was washed out with Wash Buffer. The second strand synthesis was carried out using reagents from the MessageAmp II aRNA amplification kit (Ambion), where a mixture of DNA polymerase and RNaseH in second strand buffer was used along with dNTPs by incubating the device at 16° C. for 2 hours. After flushing out the second strand reaction mixture with Wash Buffer, an in vitro transcription mixture from the MessageAmp II kit containing four nucleotides and T7 RNA polymerase enzyme mix in T7 buffer was introduced to all lanes and incubated for 13 hours at 37° C. (FIGS. 5A-5C). The reaction linearly amplified our cDNA, eluting pools of barcoded aRNA into the flow channels of the device which was then removed from each lane using a pipette and purified separately using RNA Clean & Concentrator columns (Zymo) and eluted into five separate tubes. The aRNA from the 5 lanes was reverse transcribed separately using random hexamers tagged with five different barcodes and 8-base UMIs to differentiate cDNA for all five lanes and part of an Illumina sequencing adapter. The aRNA along with the hexamer primers was heated to 70° C. for 2 mins and immediately placed on ice for 5 mins. The reverse transcription mix containing PrimeScript Reverse Transcriptase (Clontech-Takara), 0.5 mM dNTPs, 10 mM DTT, 1× PrimeScript buffer supplemented with SUPERaseIN was added and incubated at 25° C. for 10 mins followed by 2 hour incubation at 42° C. The RNA-cDNA hybrid product was purified twice using 0.65× ratio of Agencourt Ampure beads (Beckman Coulter) and the purified cDNA from all the lanes were pooled together for PCR. Phusion High Fidelity DNA polymerase (New England Biolabs) was used for amplifying the cDNA using RP1 and RPI Illumina primers in 1× PhusionHF buffer supplemented with dNTPs. The PCR product was purified on a 1.5% agarose gel which was stained with SybrGold (Life Technologies) before being cut between 400-800 bp. The library was extracted from the gel using Gel Extraction kit (Qiagen), and further purified and concentrated using a 0.65× ratio of the AMpure beads (Beckman Coulter). The final library was quantified using a Qubit (Life Technologies) and Bioanalyzer (Agilent) and sequenced on NextSeq 500 desktop sequencer (Illumina). ~240 million paired-end reads with a 26-base first read and a 66-base second read were obtained.

Procedure for Single Cell RNA-Seq Experiment 2

Experiment 2 was identical to Experiment 1 with a few exceptions. First, the two cell types under study were U87 human glioma cells and WI-38 human fibroblast cells (a diploid, limited-passage, non-cancer cell line). Second, reagents from the HiScribe In Vitro Transcription kit (New England BioLabs) were substituted for the MessageAmp II kit for the IVT portion of the protocol. Third, some of the oligonucleotides used were different from in Experiment 1 and are tabulated as detailed in Tables 4-6.

Table 4 describes a group of preferred oligonucleotides used for barcoding and library preparation for Experiment 2.

TABLE 4

| Oligonucleotide Name | Oligonucleotide Sequence |
|---|---|
| Bead Capture Oligo (5'-dual biotinylated) | AGGTAAGGTAATACGACTCACTATAGGGGTTCAGAGT TCTACAGTCCGACGATC (SEQ ID NO: 115) |
| RT1 (Reverse Transcription Primer for Lane 1) | GCCTTGGCACCCGAGAATTCCANNNNNNNNCGTCATN NNNNN (SEQ ID NO: 116) |
| RT2 (Reverse Transcription Primer for Lane 2) | GCCTTGGCACCCGAGAATTCCANNNNNNNNTACCCAN NNNNN (SEQ ID NO: 117) |
| RT3 (Reverse Transcription Primer for Lane 3) | GCCTTGGCACCCGAGAATTCCANNNNNNNNGCCATTN NNNNN (SEQ ID NO: 118) |
| RT4 (Reverse Transcription Primer for Lane 4) | GCCTTGGCACCCGAGAATTCCANNNNNNNNGAGTACN NNNNN (SEQ ID NO: 119) |
| RT5 (Reverse Transcription Primer for Lane 5) | GCCTTGGCACCCGAGAATTCCANNNNNNNNAGAGTCN NNNNN (SEQ ID NO: 120) |
| RP1 (PCR Primer 1) | AATGATACGGCGACCACCGAGATCTACACGTTCAGAG TTCTACAGTCCGA (SEQ ID NO: 121) |

TABLE 4-continued

| Oligonucleotide Name | Oligonucleotide Sequence |
|---|---|
| RPI2 (PCR Primer 2) | CAAGCAGAAGACGGCATACGAGATACATCGGTGACTG GAGTTCCTTGGCACCCGAGAATTCCA (SEQ ID NO: 122) |

Table 5 describes oligonucleotide sequences used to generate the first set of barcoded beads (FBC) for combinatorial synthesis in Experiment 2.

TABLE 5

| Oligonucleotide Name | Oligonucleotide Sequence |
|---|---|
| FBC_Oligo1 | CAGGTCCTGATCGATGATCGTCGGACTGTAGAACTCTGAAC (SEQ ID NO: 123) |
| FBC_Oligo2 | CAGGTCGTGTAGACAGATCGTCGGACTGTAGAACTCTGAAC (SEQ ID NO: 124) |
| FBC_Oligo3 | CAGGTCCATTGTTCCGATCGTCGGACTGTAGAACTCTGAAC (SEQ ID NO: 125) |
| FBC_Oligo4 | CAGGTCCTTGACTACGATCGTCGGACTGTAGAACTCTGAAC (SEQ ID NO: 126) |
| FBC_Oligo5 | CAGGTCACCGTTTCGGATCGTCGGACTGTAGAACTCTGAAC (SEQ ID NO: 127) |
| FBC_Oligo6 | CAGGTCAAGGACCGTGATCGTCGGACTGTAGAACTCTGAAC (SEQ ID NO: 128) |
| FBC_Oligo7 | CAGGTCTCACTATGCGATCGTCGGACTGTAGAACTCTGAAC (SEQ ID NO: 129) |
| FBC_Oligo8 | CAGGTCCTGCAATGGGATCGTCGGACTGTAGAACTCTGAAC (SEQ ID NO: 130) |
| FBC_Oligo9 | CAGGTCTGAGTCGTCGATCGTCGGACTGTAGAACTCTGAAC (SEQ ID NO: 131) |
| FBC_Oligo10 | CAGGTCCTCACACTAGATCGTCGGACTGTAGAACTCTGAAC (SEQ ID NO: 132) |
| FBC_Oligo11 | CAGGTCTTACCCCCTGATCGTCGGACTGTAGAACTCTGAAC (SEQ ID NO: 133) |
| FBC_Oligo12 | CAGGTCCCAAGTAGAGATCGTCGGACTGTAGAACTCTGAAC (SEQ ID NO: 134) |
| FBC_Oligo13 | CAGGTCATAGCGCACGATCGTCGGACTGTAGAACTCTGAAC (SEQ ID NO: 135) |
| FBC_Oligo14 | CAGGTCTGACGTACGGATCGTCGGACTGTAGAACTCTGAAC (SEQ ID NO: 136) |
| FBC_Oligo15 | CAGGTCGTAGAGTTGGATCGTCGGACTGTAGAACTCTGAAC (SEQ ID NO: 137) |
| FBC_Oligo16 | CAGGTCTTTCTGGCGGATCGTCGGACTGTAGAACTCTGAAC (SEQ ID NO: 138) |
| FBC_Oligo17 | CAGGTCGGAATGTGTGATCGTCGGACTGTAGAACTCTGAAC (SEQ ID NO: 139) |
| FBC_Oligo18 | CAGGTCCTATGGAAGGATCGTCGGACTGTAGAACTCTGAAC (SEQ ID NO: 140) |
| FBC_Oligo19 | CAGGTCAAGTCCATGGATCGTCGGACTGTAGAACTCTGAAC (SEQ ID NO: 141) |
| FBC_Oligo20 | CAGGTCAGTACTTGGGATCGTCGGACTGTAGAACTCTGAAC (SEQ ID NO: 142) |
| FBC_Oligo21 | CAGGTCACAGGACTAGATCGTCGGACTGTAGAACTCTGAAC (SEQ ID NO: 143) |

TABLE 5-continued

| Oligonucleotide Name | Oligonucleotide Sequence |
|---|---|
| FBC_Oligo22 | CAGGTCACCAGGTAAGATCGTCGGACTGTAGAACTCTGAAC (SEQ ID NO: 144) |
| FBC_Oligo23 | CAGGTCGCATGAACCGATCGTCGGACTGTAGAACTCTGAAC (SEQ ID NO: 145) |
| FBC_Oligo24 | CAGGTCGTTGGTGTTGATCGTCGGACTGTAGAACTCTGAAC (SEQ ID NO: 146) |
| FBC_Oligo25 | CAGGTCCCTTCAGACGATCGTCGGACTGTAGAACTCTGAAC (SEQ ID NO: 147) |
| FBC_Oligo26 | CAGGTCCCTCTTGGTGATCGTCGGACTGTAGAACTCTGAAC (SEQ ID NO: 148) |
| FBC_Oligo27 | CAGGTCGGGAAAGTTGATCGTCGGACTGTAGAACTCTGAAC (SEQ ID NO: 149) |
| FBC_Oligo28 | CAGGTCAGCCAGAGTGATCGTCGGACTGTAGAACTCTGAAC (SEQ ID NO: 150) |
| FBC_Oligo29 | CAGGTCTCGCATCTGGATCGTCGGACTGTAGAACTCTGAAC (SEQ ID NO: 151) |
| FBC_Oligo30 | CAGGTCGATACGGCAGATCGTCGGACTGTAGAACTCTGAAC (SEQ ID NO: 152) |
| FBC_Oligo31 | CAGGTCTCGGCCAAAGATCGTCGGACTGTAGAACTCTGAAC (SEQ ID NO: 153) |
| FBC_Oligo32 | CAGGTCAGATTTCGCGATCGTCGGACTGTAGAACTCTGAAC (SEQ ID NO: 154) |
| FBC_Oligo33 | CAGGTCGACCCTCAAGATCGTCGGACTGTAGAACTCTGAAC (SEQ ID NO: 155) |
| FBC_Oligo34 | CAGGTCAGTCCACTCGATCGTCGGACTGTAGAACTCTGAAC (SEQ ID NO: 156) |
| FBC_Oligo35 | CAGGTCCAAACGATCGATCGTCGGACTGTAGAACTCTGAAC (SEQ ID NO: 157) |
| FBC_Oligo36 | CAGGTCGCCTAATAGGATCGTCGGACTGTAGAACTCTGAAC (SEQ ID NO: 158) |
| FBC_Oligo37 | CAGGTCGGCTACATCGATCGTCGGACTGTAGAACTCTGAAC (SEQ ID NO: 159) |
| FBC_Oligo38 | CAGGTCTATGAGCAGGATCGTCGGACTGTAGAACTCTGAAC (SEQ ID NO: 160) |
| FBC_Oligo39 | CAGGTCGGTAGTAACGATCGTCGGACTGTAGAACTCTGAAC (SEQ ID NO: 161) |
| FBC_Oligo40 | CAGGTCCGCGTATATGATCGTCGGACTGTAGAACTCTGAAC (SEQ ID NO: 162) |
| FBC_Oligo41 | CAGGTCTACTGGAGCGATCGTCGGACTGTAGAACTCTGAAC (SEQ ID NO: 163) |
| FBC_Oligo42 | CAGGTCAGGGAATCAGATCGTCGGACTGTAGAACTCTGAAC (SEQ ID NO: 164) |
| FBC_Oligo43 | CAGGTCATCCGAGATGATCGTCGGACTGTAGAACTCTGAAC (SEQ ID NO: 165) |
| FBC_Oligo44 | CAGGTCTCCCAAGCAGATCGTCGGACTGTAGAACTCTGAAC (SEQ ID NO: 166) |
| FBC_Oligo45 | CAGGTCGAGCCGTTTGATCGTCGGACTGTAGAACTCTGAAC (SEQ ID NO: 167) |
| FBC_Oligo46 | CAGGTCTGCTCTTACGATCGTCGGACTGTAGAACTCTGAAC (SEQ ID NO: 168) |
| FBC_Oligo47 | CAGGTCACGACTACCGATCGTCGGACTGTAGAACTCTGAAC (SEQ ID NO: 169) |

TABLE 5-continued

| Oligonucleotide Name | Oligonucleotide Sequence |
| --- | --- |
| FBC_Oligo48 | CAGGTCCAAGCAGCTGATCGTCGGACTGTAGAACTCTGAAC (SEQ ID NO: 170) |
| FBC_Oligo49 | CAGGTCGTATTCGCGATCGTCGGACTGTAGAACTCTGAAC (SEQ ID NO: 171) |
| FBC_Oligo50 | CAGGTCGCTCTGAAGATCGTCGGACTGTAGAACTCTGAAC (SEQ ID NO: 172) |
| FBC_Oligo51 | CAGGTCACGTAGTGGATCGTCGGACTGTAGAACTCTGAAC (SEQ ID NO: 173) |
| FBC_Oligo52 | CAGGTCATTGGGTCGATCGTCGGACTGTAGAACTCTGAAC (SEQ ID NO: 174) |
| FBC_Oligo53 | CAGGTCAACAGCACGATCGTCGGACTGTAGAACTCTGAAC (SEQ ID NO: 175) |
| FBC_Oligo54 | CAGGTCTCAGAGACGATCGTCGGACTGTAGAACTCTGAAC (SEQ ID NO: 176) |
| FBC_Oligo55 | CAGGTCGTGTGCTAGATCGTCGGACTGTAGAACTCTGAAC (SEQ ID NO: 177) |
| FBC_Oligo56 | CAGGTCGCAGTTGAGATCGTCGGACTGTAGAACTCTGAAC (SEQ ID NO: 178) |
| FBC_Oligo57 | CAGGTCTTAACGGGGATCGTCGGACTGTAGAACTCTGAAC (SEQ ID NO: 179) |
| FBC_Oligo58 | CAGGTCGCTCGATTGATCGTCGGACTGTAGAACTCTGAAC (SEQ ID NO: 180) |
| FBC_Oligo59 | CAGGTCACACCTGTGATCGTCGGACTGTAGAACTCTGAAC (SEQ ID NO: 181) |
| FBC_Oligo60 | CAGGTCAGACGGTTGATCGTCGGACTGTAGAACTCTGAAC (SEQ ID NO: 182) |
| FBC_Oligo61 | CAGGTCGCAAACCAGATCGTCGGACTGTAGAACTCTGAAC (SEQ ID NO: 183) |
| FBC_Oligo62 | CAGGTCGAGTATGGGATCGTCGGACTGTAGAACTCTGAAC (SEQ ID NO: 184) |
| FBC_Oligo63 | CAGGTCGGTCTTTCGATCGTCGGACTGTAGAACTCTGAAC (SEQ ID NO: 185) |
| FBC_Oligo64 | CAGGTCCATCTGCTGATCGTCGGACTGTAGAACTCTGAAC (SEQ ID NO: 186) |
| FBC_Oligo65 | CAGGTCTTCGCAAGGATCGTCGGACTGTAGAACTCTGAAC (SEQ ID NO: 187) |
| FBC_Oligo66 | CAGGTCTTGTGACGGATCGTCGGACTGTAGAACTCTGAAC (SEQ ID NO: 188) |
| FBC_Oligo67 | CAGGTCTGCATGACGATCGTCGGACTGTAGAACTCTGAAC (SEQ ID NO: 189) |
| FBC_Oligo68 | CAGGTCCAACGTGAGATCGTCGGACTGTAGAACTCTGAAC (SEQ ID NO: 190) |
| FBC_Oligo69 | CAGGTCTAGGCTTCGATCGTCGGACTGTAGAACTCTGAAC (SEQ ID NO: 191) |
| FBC_Oligo70 | CAGGTCTGGTAGGAGATCGTCGGACTGTAGAACTCTGAAC (SEQ ID NO: 192) |
| FBC_Oligo71 | CAGGTCTGCAGCTTGATCGTCGGACTGTAGAACTCTGAAC (SEQ ID NO: 193) |
| FBC_Oligo72 | CAGGTCCTGTACCTGATCGTCGGACTGTAGAACTCTGAAC (SEQ ID NO: 194) |
| FBC_Oligo73 | CAGGTCCGCAATGAGATCGTCGGACTGTAGAACTCTGAAC (SEQ ID NO: 195) |

TABLE 5-continued

| Oligonucleotide Name | Oligonucleotide Sequence |
|---|---|
| FBC_Oligo74 | CAGGTCGATCCAAGGATCGTCGGACTGTAGAACTCTGAAC (SEQ ID NO: 196) |
| FBC_Oligo75 | CAGGTCCACTTACGGATCGTCGGACTGTAGAACTCTGAAC (SEQ ID NO: 197) |
| FBC_Oligo76 | CAGGTCAACTAGGCGATCGTCGGACTGTAGAACTCTGAAC (SEQ ID NO: 198) |
| FBC_Oligo77 | CAGGTCACTAGCGTGATCGTCGGACTGTAGAACTCTGAAC (SEQ ID NO: 199) |
| FBC_Oligo78 | CAGGTCCGTTCGTTGATCGTCGGACTGTAGAACTCTGAAC (SEQ ID NO: 200) |
| FBC_Oligo79 | CAGGTCAGTCACGAGATCGTCGGACTGTAGAACTCTGAAC (SEQ ID NO: 201) |
| FBC_Oligo80 | CAGGTCCCTGTAACGATCGTCGGACTGTAGAACTCTGAAC (SEQ ID NO: 202) |
| FBC_Oligo81 | CAGGTCGTCCTCTTGATCGTCGGACTGTAGAACTCTGAAC (SEQ ID NO: 203) |
| FBC_Oligo82 | CAGGTCCAGCGAATGATCGTCGGACTGTAGAACTCTGAAC (SEQ ID NO: 204) |
| FBC_Oligo83 | CAGGTCATGGTTGGGATCGTCGGACTGTAGAACTCTGAAC (SEQ ID NO: 205) |
| FBC_Oligo84 | CAGGTCGAGGTTCTGATCGTCGGACTGTAGAACTCTGAAC (SEQ ID NO: 206) |
| FBC_Oligo85 | CAGGTCTACCTCGAGATCGTCGGACTGTAGAACTCTGAAC (SEQ ID NO: 207) |
| FBC_Oligo86 | CAGGTCTTCTGTGCGATCGTCGGACTGTAGAACTCTGAAC (SEQ ID NO: 208) |
| FBC_Oligo87 | CAGGTCGACAACTGGATCGTCGGACTGTAGAACTCTGAAC (SEQ ID NO: 209) |
| FBC_Oligo88 | CAGGTCCGACAACAGATCGTCGGACTGTAGAACTCTGAAC (SEQ ID NO: 210) |
| FBC_Oligo89 | CAGGTCTCGATACCGATCGTCGGACTGTAGAACTCTGAAC (SEQ ID NO: 211) |
| FBC_Oligo90 | CAGGTCCCATACTCGATCGTCGGACTGTAGAACTCTGAAC (SEQ ID NO: 212) |
| FBC_Oligo91 | CAGGTCATTCGCAGGATCGTCGGACTGTAGAACTCTGAAC (SEQ ID NO: 213) |
| FBC_Oligo92 | CAGGTCACCATAGGGATCGTCGGACTGTAGAACTCTGAAC (SEQ ID NO: 214) |
| FBC_Oligo93 | CAGGTCCGATCAAGGATCGTCGGACTGTAGAACTCTGAAC (SEQ ID NO: 215) |
| FBC_Oligo94 | CAGGTCACCTTGCTGATCGTCGGACTGTAGAACTCTGAAC (SEQ ID NO: 216) |
| FBC_Oligo95 | CAGGTCGACTCAGTGATCGTCGGACTGTAGAACTCTGAAC (SEQ ID NO: 217) |

TABLE 5-continued

| Oligonucleotide Name | Oligonucleotide Sequence |
|---|---|
| FBC_Oligo96 | CAGGTCGTCAATCCGATCGTCGGACTGTAGAACTCTGAAC (SEQ ID NO: 218) |

Table 6 provides for oligonucleotide sequences used to generate the second set of barcoded beads (SBC) for combinatorial synthesis in Experiment 2.

TABLE 6

| Oligonucleotide Name | Oligonucleotide Sequence |
|---|---|
| SBC_Oligo1 | AAAAAAAAAAAAAAAAAAAAAAAAGGTGATACAGGTCAAAAAAAAAGATCG TCGGACTGTAGAACTC (SEQ ID NO: 219) |
| SBC_Oligo2 | AAAAAAAAAAAAAAAAAAAAAAAATGAATGCCAGGTCAAAAAAAAAGATCG TCGGACTGTAGAACTC (SEQ ID NO: 220) |
| SBC_Oligo3 | AAAAAAAAAAAAAAAAAAAAAAAATGCCAAACAGGTCAAAAAAAAAGATCG TCGGACTGTAGAACTC (SEQ ID NO: 221) |
| SBC_Oligo4 | AAAAAAAAAAAAAAAAAAAAAAAACAGAAGCAGGTCAAAAAAAAAGATCG TCGGACTGTAGAACTC (SEQ ID NO: 222) |
| SBC_Oligo5 | AAAAAAAAAAAAAAAAAAAAAAAACACTGGACAGGTCAAAAAAAAAGATCG TCGGACTGTAGAACTC (SEQ ID NO: 223) |
| SBC_Oligo6 | AAAAAAAAAAAAAAAAAAAAAAAACGATGATCAGGTCAAAAAAAAAGATCG TCGGACTGTAGAACTC (SEQ ID NO: 224) |
| SBC_Oligo7 | AAAAAAAAAAAAAAAAAAAAAAAGTGTCCACAGGTCAAAAAAAAAGATCG TCGGACTGTAGAACTC (SEQ ID NO: 225) |
| SBC_Oligo8 | AAAAAAAAAAAAAAAAAAAAAAAATCCTCTTCAGGTCAAAAAAAAAGATCG TCGGACTGTAGAACTC (SEQ ID NO: 226) |
| SBC_Oligo9 | AAAAAAAAAAAAAAAAAAAAAAAGTGCAGTCAGGTCAAAAAAAAAGATCG TCGGACTGTAGAACTC (SEQ ID NO: 227) |
| SBC_Oligo10 | AAAAAAAAAAAAAAAAAAAAAAAAGGTAGACAGGTCAAAAAAAAAGATCG TCGGACTGTAGAACTC (SEQ ID NO: 228) |

Analysis of Single Cell RNA-Seq Data

Read 1 of the single cell RNA-Seq data contains a cell-identifying barcode sequence followed by poly(dT), and read 2 contains a 8-base UMI followed by a 6-base lane-identifying barcode and a transcript sequence. The reads are first demultiplex based on the lane-identifying barcode while recording the corresponding UMI using a custom Python script. We then map the remainder of read 2 to the human genome and transcriptome (hg19, Ensembl annotation from Illumina iGenomes) using the STAR aligner. Mapped reads for each lane are then demultiplexed based on the cell-identifying barcodes in read 1 and assigned to a gene using HTSeq. Both the lane- and cell-identifying barcodes were allowed to have a single-base mismatch during demultiplexing.

The set of reads that uniquely mapped to the transcriptome were collected and assigned an address comprised of its cell-identifying barcode, gene, UMI, and mapping position. In addition, the reads that mapped to both the genome and transcriptome were kept, but that mapped to only one position on the transcriptome and mapped to that position with the appropriate strand-specificity. The reads to identify unique molecules were filtered. Reads with identical addresses were collapsed to a single molecule. In addition, reads with identical cell-identifying barcodes, genes, mapping positions, and with UMIs having a Hamming distance less than or equal to two were collapsed to a single molecule. All reads considered identical molecules by the above definition (UMIs with a Hamming distance less than or equal to two and mapping position within six bases) were removed but that also occurred with different cell-identifying barcodes within the same lane. This approach likely underestimates of the true number of molecules associated with each cell and gene and results in some loss of gene detection. However, it also removes molecules that may become spuriously associated with the incorrect cell via PCR recombination, as observed and similarly filtered in previous studies that used very similar library construction protocols.

To identify barcodes that correspond to actual individual cells in our device in Experiment 1, the observed cell-identifying barcodes were filtered by progressively down-sampling the corresponding gene profiles to the same number of total reads and assessing the number of unique molecules detected from each cell-identifying barcode. After excluding cell-identifying barcodes having zero associated molecules, it was found that the distribution of associated unique molecules to be bimodal, with one small subpopulation having nearly as many unique molecules as reads at low read totals. It was found the size of this subpopulation to be in excellent agreement with our device imaging data. These 598 profiles were taken to represent the actual individual cells captured in the device with a barcoded bead. We used the same approach to assess the cell-identifying barcodes in Experiment 2.

The 396 single-cell profiles were kept with the highest coverage in the data set (all five lanes represented). The U87 and MCF10a single cell profiles were compared to bulk RNA-Seq profiles of U87 and MCF10a cells. Bulk RNA-Seq library from ~107 U87 cells were prepared using the TruSeq RNA-Seq library preparation kit (Illumina) and sequenced the library to a depth of ~30M, 100-base single-end reads on an Illumina HiSeq 2500. Publically available bulk RNA-Seq profile of MCF10a cells was obtained from the Gene Expression Omnibus (entry GSE45258). Reads were mapped to the transcriptome as described above and expression values (FPKM) were computed using Cufflinks. Pearson correlation coefficients between single cell and bulk profiles were computed between log-transformed single-cell expression profiles (unique molecules per million reads plus one) and log-transformed bulk values (FPKM plus one). Single cell median profiles were generated from different numbers of randomly selected single cell profiles and repeated this random sampling ten times without replacement for each data point in FIGS. 7A and 7B. For each Pearson correlation calculation, only genes with log-transformed single cell median or bulk values greater than 0.5 were included.

Differential expression analysis was conducted by comparing each detected gene in the two cell type-exclusive lanes using Wilcoxin's rank-sum test. Genes with $p<0.05$ were used for clustering analysis. Regardless of differential expression +/−(1-p) was used (which is positive for expression biased in one cell type and negative for expression biased towards a second cell type) for each gene as input to iPAGE, a mutual information-based algorithm that can associate gene ontologies with genes based on an assigned numerical value[35]. A matrix of pairwise Spearman correlation coefficients was generated based on unique molecules detected across 396 single cell profiles in Experiment 1 (247 profiles in Experiment 2) using only the differentially expressed genes. The data was then clustered with the MATLAB implementation t-SNE using the correlation matrix as input. The single cell profiles were color coated in the t-SNE clusters using a simple classifier score given by the log-ratio of the number of cell type-specific genes for each of the two cell types in a given cell with an above-average rank in expression level (FIG. 8C).

Table 7 describes estimated costs per reagents and associated costs in an aspect of the disclosure.

TABLE 7

| Table 7 describes estimated costs per reagents and associated costs in an aspect of the disclosure. | | | | |
| --- | --- | --- | --- | --- |
| Reagent | Volume | Stock Volume | Price of Stock | Price per Run |
| SUPERaseIN (Ambion) | 19 uL | 500 uL | $350.40 | $13.32 |
| dNTPs (NEB) | 10 uL | 800 uL | $44.80 | $0.56 |
| HiScribe IVT Kit (NEB) | 1 uL | 50 uL | $169.60 | $3.39 |
| MessageAamp II Kit (Ambion)* | 3 uL | 740 uL | $3,668.00 | $14.87 |
| PrimeScript RT (Clontech) | 5 uL | 200 uL | $501.63 | $12.54 |
| Phusion polymerase (NEB) | 0.5 uL | 250 uL | $336.00 | $0.67 |
| Lane Barcode RT primary (IDT) | 15 uL | 3155 uL | $542.25 | $0.86 |
| NHS beads (GE) | 3.5 uL | 25000 uL | $155.80 | $0.02 |
| Streptavidin (DEB) | 5 uL | 1000 uL | $188.80 | $0.94 |
| Dual-biotin anchor oligo (IDT) | 0.64 uL | 700 uL | $225.75 | $0.21 |
| Klenow fragment exo− (NEB) | 1.5 uL | 200 uL | $188.80 | $1.42 |
| dNTPs (NEB) | 3.5 uL | 800 uL | $44.80 | $0.20 |
| FBC primers (IDT) | 0.96 uL (all 96) | 240,000 uL (all 96) | $484.56 total | $0.00 |
| SBC primers (IDT) | 0.66 uL (all 10) | 4000 uL (all 10) | $340.00 total | $0.67 |
| Experiment Costs | | | | $46.21 |
| Bead Costs | | | | $3.46 |
| Total Cost per Run | | | | $49.67 |
| Cost per Cell | 250-500 cells | | | $0.10-$0.20 |

What is claimed is:

1. A method of visualizing mRNA capture beads in a device that comprises a plurality of chambers, microchambers, or microwells each containing at least one of at least 32 mRNA capture beads, comprising:

a) contacting each of said plurality of chambers, microchambers, or microwells with first optically labelled oligonucleotides, wherein each of said at least 32 mRNA capture beads is labelled with a primer sequence comprising a unique combination of the presence or absence of each member of a set of barcode sequences, wherein said members of said set of barcode sequences: i) comprise first, second, third, fourth, and fifth barcodes sequences, and ii) are unique with respect to each other; and wherein said first optically labeled oligonucleotides are from a set of optically labeled oligonucleotides comprising: said first optically labeled oligonucleotides and, second, third, fourth, and fifth optically labeled oligonucleotides, each of which hybridizes to one, and only one, of said correspondingly numbered members of said set of barcode sequences present on said primer sequences, b) washing said plurality of chambers, microchambers, or microwells containing mRNA capture beads with wash buffer to remove said first optically labeled oligonucleotides that are not hybridized to said primer sequences; and c) imaging said plurality of chambers, microchambers, or microwells containing mRNA capture beads to identify wells that have an mRNA capture bead that is labeled with said first optically labelled oligonucleotide via hybridization to said primer sequences, thereby generating initial imaging data indicating the presence of first barcode sequences.

2. The method of claim 1, further comprising:

d) contacting said plurality of chambers, microchambers, or microwells with a denaturing solution, thereby causing said first optically labelled oligonucleotides to dissociate from said primer sequences on said mRNA capture beads;

e) washing said plurality of chambers, microchambers, or microwells with wash buffer; and f) repeating steps a)-e) successively with said second, third, fourth, and fifth optically labelled oligonucleotides, thereby generating final imaging data identifying the unique combination of the presence or absence of each member of a set of barcode sequences for each of said at least 32 mRNA capture beads.

3. The method of claim 2, wherein one, and only one, cell is present in each of said plurality of chambers, microchambers, or microwells containing mRNA capture beads.

4. The method of claim 3, further comprising: lysing said cells to release mRNA, and sequencing said mRNA from said cells that is captured on said plurality of mRNA capture beads via said primer sequences to generate sequencing data.

5. The method of claim 4, further comprising linking said final imaging data with said sequencing data for at least some of said chambers, microchambers, or microwells.

6. The method of claim 3, wherein a drug is present in said plurality of chambers, microchambers, or microwells.

7. The method of claim 1, wherein one, and only one, mRNA capture bead is present in each of said plurality of chambers, microchambers, or microwells.

8. The method of claim 1, wherein each of said optically labeled oligonucleotides are each fluorescently labeled.

9. The method of claim 1, wherein each of said primer sequences further comprises an oligo(dT) sequence.

10. The method of claim 1, wherein each of said primer sequences further comprises a sequencing adapter.

11. The method of claim 1, wherein each of said primer sequences further comprises a T7 promoter sequence.

12. The method of claim 1, wherein each of said primer sequences: i) comprises said unique combination of the presence or absence of each member of a set of barcode sequences, and ii) further comprises: A) an oligo(dT) sequence, B) an adapter sequence, and C) a T7 promoter sequence.

* * * * *